(12) United States Patent
Murphy Kessabi et al.

(10) Patent No.: US 8,507,509 B2
(45) Date of Patent: Aug. 13, 2013

(54) SATURATED AND INSATURATED BI- OR TRICYCLIC ARYLOXYACETAMINE DERIVATIVES AND THEIR USE AS FUNGICIDES

(75) Inventors: Fiona Murphy Kessabi, Stein (CH); Hans-Georg Brunner, Lausen (CH); Renaud Beaudegnies, Stein (CH); Laura Quaranta, Stein (CH); Fredrik Cederbaum, Stein (CH); Jayant Umarye, Goa (IN)

(73) Assignee: Syngenta Crop Protection LLC, Greensboro, NC (US)

( * ) Notice: Subject to any disclaimer, the term of this patent is extended or adjusted under 35 U.S.C. 154(b) by 456 days.

(21) Appl. No.: 12/676,374

(22) PCT Filed: Sep. 3, 2008

(86) PCT No.: PCT/EP2008/007191
§ 371 (c)(1),
(2), (4) Date: Jun. 29, 2010

(87) PCT Pub. No.: WO2009/030467
PCT Pub. Date: Mar. 12, 2009

(65) Prior Publication Data
US 2010/0298356 A1    Nov. 25, 2010

(30) Foreign Application Priority Data

Sep. 5, 2007   (GB) .................................. 0717256.2

(51) Int. Cl.
| | | |
|---|---|---|
| A01N 43/54 | (2006.01) |
| A01N 43/42 | (2006.01) |
| A01N 43/12 | (2006.01) |
| A01N 37/18 | (2006.01) |
| A61K 31/517 | (2006.01) |
| A01P 3/00 | (2006.01) |
| C07C 235/32 | (2006.01) |
| C07C 255/38 | (2006.01) |
| C07D 215/48 | (2006.01) |
| C07D 239/72 | (2006.01) |
| C07D 277/68 | (2006.01) |

(52) U.S. Cl.
USPC ........ 514/266.1; 514/183; 514/314; 514/367; 546/175; 548/178

(58) Field of Classification Search
USPC .............. 514/266.1, 183, 314, 367; 546/175; 549/469, 51
See application file for complete search history.

(56) References Cited

FOREIGN PATENT DOCUMENTS

| | | | |
|---|---|---|---|
| EP | 0940392 | 9/1999 | |
| JP | 2001089453 | 4/2001 | |
| JP | 2007161701 | 6/2007 | |
| WO | 2004047538 | 6/2004 | |
| WO | WO 2006058700 | * | 6/2006 |

* cited by examiner

*Primary Examiner* — Sreeni Padmanabhan
*Assistant Examiner* — Uma Ramachandran
(74) *Attorney, Agent, or Firm* — R. Kody Jones

(57) ABSTRACT

Compounds of the general formula (I), wherein the substituents are as defined in claim 1, are useful as fungicides.

(I)

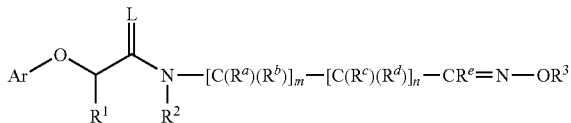

9 Claims, No Drawings

SATURATED AND INSATURATED BI- OR TRICYCLIC ARYLOXYACETAMINE DERIVATIVES AND THEIR USE AS FUNGICIDES

This application is a 371 of International Application No. PCT/EP2008/007191 filed Sep. 3, 2008, which claims priority to GB 0717256.2 filed Sep. 5, 2007, the contents of which are incorporated herein by reference.

This invention relates to novel acid amides, processes for preparing them, to compositions containing them and to methods of using them to combat fungi, especially fungal infections of plants.

Certain acid amide derivatives and their use as agricultural and horticultural bactericides are disclosed, for example, in WO 04/047538 and JP 2001-89453.

The present invention is concerned with the provision of particular substituted acid amides for use mainly as plant fungicides.

Thus, according to the present invention there is provided a compound of the general formula (1)

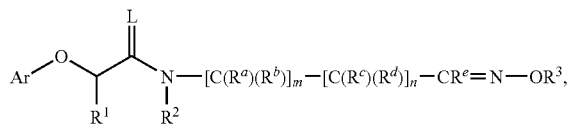

(1)

wherein
Ar is an optionally substituted 8- to 14 membered saturated or unsaturated bi- or tricyclic ring,
L is O or S;
$R^1$ is $C_{1-4}$ alkyl, halo$C_{1-4}$alkyl or $C_{3-4}$cycloalkyl, or $C_{1-4}$alkoxy, halo($C_{1-4}$)alkoxy or $C_{3-4}$cycloalkoxy, or $C_{1-4}$alkylthio, $C_{1-4}$alkylsulphinyl or $C_{1-4}$alkylsulphonyl, or halo($C_{1-4}$)alkylthio, halo($C_{1-4}$)alkylsulphinyl or halo($C_{1-4}$)alkylsulphonyl, or $C_{3-4}$cycloalkylthio, $C_{3-4}$cycloalkylsulphinyl or $C_{3-4}$cycloalkylsulphonyl;
$R^2$ is hydrogen, $C_{1-8}$alkyl, $C_{3-4}$cycloalkyl, $C_{2-8}$alkenyl, cyano($C_{1-4}$alkyl, $C_{1-4}$alkoxy($C_{1-4}$)-alkyl, $C_{1-4}$alkoxy($C_{1-4}$)alkoxy($C_{1-4}$)alkyl or benzyloxy($C_{1-4}$alkyl, in which the phenyl ring of the benzyl moiety is optionally substituted with $C_{1-4}$alkoxy;
$R^a$ and $R^b$, independently of each other, are hydrogen, $C_{1-4}$ alkyl, $C_{1-4}$ haloalkyl, $C_{1-4}$ alkoxy($C_{1-4}$)alkyl, $C_{3-5}$alkenyloxy($C_{1-4}$)alkyl, $C_{3-5}$alkynyloxy($C_{1-4}$)alkyl, $C_{1-4}$hydroxyalkyl, cyano, $C_{2-4}$alkynyl, $C_{2-4}$alkenyl or $C_{1-4}$alkoxycarbonyl, formyl, $C_{1-3}$alkoxy($C_{1-3}$)alkyl($C_{1-3}$)-alkynyl, $C_{1-3}$alkenyloxy($C_{1-3}$)alkyl($C_{1-3}$)alkynyl, $C_{1-3}$ alkynyloxy($C_{1-3}$)alkyl($C_{1-3}$)alkynyl or hydroxy($C_{1-3}$)alkyl($C_{1-3}$)alkynyl,
$R^c$ and $R^d$, independently of each other, are hydrogen, $C_{1-4}$ alkyl, halogen, cyano, hydroxy, $C_{1-4}$alkoxy or $C_{1-4}$alkoxycarbonyl, or
$R^a$ together with $R^b$, or $R^c$ together with $R^d$ may join to form together with the carbon atoms to which they are attached a 3 to 6 membered carbocyclic or heterocyclic ring containing a heteroatom selected from sulfur, oxygen, nitrogen and $NR^o$, wherein $R^o$ is hydrogen or optionally substituted $C_{1-4}$alkyl,
$R^e$ is hydrogen or $C_{1-4}$ alkyl, phenyl, benzyl, thienylmethyl or pyridylmethyl,
$R^3$ is hydrogen, optionally substituted $C_{1-6}$alkyl, optionally substituted $C_{3-6}$cycloalkyl which optionally contains a heteratom selected from oxygen, sulphur or nitrogen, optionally substituted $C_{2-4}$alkenyl, optionally substituted $C_{2-6}$alkynyl, $C_{1-4}$alkoxy($C_{1-4}$)alkyl, $C_{3-5}$ alkenyloxy($C_{1-4}$)alkyl, $C_{3-5}$ alkynyloxy($C_{1-4}$)alkyl, optionally substituted aryl or optionally substituted heteroaryl,
m is 1 or 2,
n is 0, 1 or 2, and
salts and N-oxides of the compounds of the formula (1), with the proviso that when Ar is a quinolin-6-yl group and $R^1$ is $C_{1-4}$alkylthio, $C_{1-4}$alkylsulphinyl or $C_{1-4}$alkylsulphonyl, or halo($C_{1-4}$)alkylthio, halo($C_{1-4}$)alkylsulphinyl or halo($C_{1-4}$)alkylsulphonyl, or $C_{3-4}$cycloalkylthio, $C_{3-4}$cyclo-alkylsulphinyl or $C_{3-4}$cycloalkylsulphonyl, then the position 7 of the quinolin-6-yl is unsubstituted.

The compounds of the invention contain at least one asymmetric carbon atom and may exist as enantiomers (or as pairs of diastereoisomers) or as mixtures of such. Further, when $R^1$ is $C_{1-4}$alkylsulphinyl the compounds of the invention are sulphoxides, which can exist in two enantiomeric forms, and the adjacent carbon can also exist in two enantiomeric forms.

Furthermore, isomerism around the C=N double bond of compounds of the invention can exist thereby leading to stereochemically isomeric forms of compounds of the general formula (1). In cases where the compounds of the invention exist as the E and Z isomers, the invention includes individual isomers as well as mixtures thereof.

Compounds of general formula (I) can therefore exist as racemates, diastereoisomers, or single enantiomers, and the invention includes all possible isomers or isomer mixtures in all proportions. It is to be expected that for any given compound, one isomer may be more fungicidally active than another. N-oxides of the compounds of the formula (1) preferably denote the N-oxides formed, for example, when Ar is a quinolinyl or quinazolinyl moiety.

The salts which the compounds of the formula I can form are preferably those formed by interaction of these compounds with acids. The term "acid" comprises mineral acids such as hydrogen halides, sulphuric acid, phosphoric acid etc. as well as organic acids, preferably the commonly used alkanoic acids, for example formic acid, acetic acid and propionic acid.

Except where otherwise stated, alkyl groups and alkyl moieties of alkoxy, alkylthio, etc., suitably contain from 1 to 8, typically from 1 to 4, carbon atoms in the form of straight or branched chains. Examples are methyl, ethyl, n- and iso-propyl and n-, sec-, iso- and tert-butyl. Where alkyl moieties contain 5 or 6 carbon atoms, examples are n-pentyl and n-hexyl. Examples of suitable optional substituents of alkyl groups and moieties include halo, hydroxy, $C_{1-4}$alkoxy and $C_{1-4}$alkoxy($C_{1-4}$)alkoxy, cyano, optionally substituted aryl and optionally substituted heteroaryl. Where the optional substituent is halo, the haloalkyl group or moiety is typically monochloromethyl, monofluoromethyl, monofluoroethyl, dichloromethyl, difluoromethyl, trichloromethyl or trifluoromethyl. Preferred substituents are halo, hydroxy, $C_{1-4}$alkoxy and $C_{1-4}$alkoxy($C_{1-4}$)alkoxy and cyano.

The cycloalkyl radicals suitably contain 3 or 6 carbon atoms and are cyclopropyl, cyclobutyl, cyclopentyl or cyclohexyl.

Except where otherwise stated, alkenyl and alkynyl moieties also suitably contain from 2 to 6, typically from 2 to 4, carbon atoms in the form of straight or branched chains. Examples are allyl, ethynyl and propargyl.

Optional substituents on cycloalkyl, alkenyl and alkynyl comprise halo, alkoxyalkyl, alkenylalkyl, alkynylalkyl, haloalkyl, cyanoalkyl, hydroxyalkyl, alkoxy, optionally substituted aryl and optionally substituted heteroaryl.

Preferred substituents are halo, $C_{1-4}$alkoxy$(C_{1-3})$alkyl, $C_{2-4}$alkenyl$(C_{1-3})$alkyl, $C_{2-4}$alkynyl$(C_{1-3})$alkyl, $C_{1-4}$haloalkyl, $C_{1-4}$cyanoalkyl, $C_{1-4}$hydroxyalkyl, $C_{1-4}$alkoxy, Halo includes fluoro, chloro, bromo and iodo.

Aryl is preferably phenyl but also includes bi- and tricyclic rings such as naphthyl, anthryl and phenanthryl, preferably naphthyl.

Heteroaryl is typically a 5- or 6-membered aromatic ring containing one or more sulphur, oxygen, nitrogen or $NR^o$ moieties as heteroatoms, which may be fused to one or more other aromatic or heteroaromatic rings, such as a benzene ring. Examples are thienyl, furyl, pyrrolyl, isoxazolyl, oxazolyl, thiazolyl, oxadiazolyl, pyrazolyl, imidazolyl, triazolyl, isothiazolyl, tetrazolyl, thiadiazolyl, pyridyl, pyrimidinyl, pyrazinyl, pyridazinyl, triazinyl, benzofuranyl, benzothienyl, dibenzofuranyl, dibenzothienyl, benzothiazolyl, benzoxazolyl, benzimidazolyl, indolyl, quinolyl, isoquinolyl, quinazolinyl and quinoxalinyl groups and, where appropriate, N-oxides and salts thereof. Any of the aryl or heteroaryl values are optionally substituted. Preferred rings are benzofuranyl, benzothienyl, quinolyl, and quinazolinyl.

The 8- to 14-membered rings Ar are bi- or tricyclic systems which can be saturated or unsaturated. They comprise carbocyclic as well as heterocyclic rings, aryl and heteroaryl, where the heterocycles and heteroaryls usually contain a sulphur, oxygen, nitrogen or $NR^o$ moiety, where $R^o$ is hydrogen o an alkyl group, which can be substituted.

Except where otherwise stated, substituents which may be present on the bi- and tricyclic rings as well as aryl and heteroaryl include, for example, one or more of the following: halo, hydroxy, mercapto, $C_{1-6}$alkyl (especially methyl and ethyl), $C_{2-6}$alkenyl (especially vinyl and allyl), $C_{2-6}$alkynyl (especially ethynyl propargyl), trialkylsilylethynyl (especially trimethylsilylethynyl), 3-hydroxy-3-$(C_{1-4})$alkyl$(C_{3-6})$alk-1-yn-1-yl (especially 3-hydroxy-3-methyl-but-1-yn-1-yl), $C_{1-6}$alkoxy (especially methoxy), $C_{2-6}$alkenyloxy (especially allyloxy), $C_{2-6}$alkynyloxy (especially propargyloxy), halo$(C_{1-6})$alkyl (especially trifluoromethyl), halo $(C_{1-6})$alkoxy (especially trifluoromethoxy), $-S(O)_u(C_{1-6})$alkyl wherein u is 0, 1 or 2 and the alkyl is optionally substituted with halo, hydroxy$(C_{1-6})$alkyl, $C_{1-4}$ alkoxy$(C_{1-4})$alkyl, $C_{1-4}$alkoxy$(C_{1-4})$alkoxy, $C_{3-6}$cycloalkyl, $C_{3-6}$cycloalkyl$(C_{1-4}$ alkyl, optionally substituted aryl (especially optionally substituted phenyl), optionally substituted heteroaryl (especially optionally substituted pyridyl, pyrimidinyl or thienyl), optionally substituted aryloxy (especially optionally substituted phenoxy), optionally substituted heteroaryloxy (especially optionally substituted pyridyloxy or pyrimidinyloxy), optionally substituted $-S(O)_p$aryl wherein mp is 0, 1 or 2 (especially optionally substituted phenylthio), optionally substituted $-S(O)_q$heteroaryl wherein q is 0, 1 or 2 (especially optionally substituted pyridylthio or pyrimidinylthio), optionally substituted aryl$(C_{1-4})$alkyl (especially optionally substituted benzyl, optionally substituted phenethyl and optionally substituted phenyl n-propyl) in which the alkyl moiety is optionally substituted with hydroxy, optionally substituted heteroaryl$(C_{1-4})$alkyl (especially optionally substituted pyridyl- or pyrimidinyl$(C_{1-4})$alkyl), optionally substituted aryl$(C_{2-4})$alkenyl (especially optionally substituted phenylethenyl), optionally substituted heteroaryl$(C_{2-4})$alkenyl (especially optionally substituted pyridylethenyl or pyrimidinylethenyl), optionally substituted aryl$(C_{1-4})$alkoxy (especially optionally substituted benzyloxy and phenethyloxy), optionally substituted heteroaryl$(C_{1-4})$alkoxy (especially optionally substituted pyridyl$(C_{1-4})$alkoxy or pyrimidinyl $(C_{1-4})$alkoxy), optionally substituted aryloxy-$(C_{1-4})$alkyl (especially phenoxymethyl), optionally substituted heteroaryloxy-$(C_{1-4})$alkyl (especially optionally substituted pyridyloxy or pyrimidinyloxy$(C_{1-4})$alkyl), optionally substituted $-S(O)_r(C_{1-4})$alkylaryl wherein r is 0, 1 or 2 (especially optionally substituted benzylthio and phenethylthio), optionally substituted $-S(O)_s(C_{1-4})$alkylheteroaryl wherein s is 0, 1 or 2 (especially optionally substituted pyridyl$(C_{1-4})$alkylthio or pyrimidinyl$(C_{1-4})$-alkylthio), optionally substituted $-(C_{1-4})$alkylS$(O)_y$, aryl wherein y is 0, 1 or 2 (especially phenylthiomethyl), optionally substituted $-(C_{1-4})$alkyl S$(O)_x$heteroaryl wherein x is 0, 1 or 2 (especially optionally substituted pyridylthio$(C_{1-4})$alkyl or pyrimidinylthio$(C_{1-4})$ alkyl), acyloxy, including $C_{1-4}$ alkanoyloxy (especially acetyloxy) and benzoyloxy, cyano, isocyano, thiocyanato, isothiocyanato, nitro, $NR^gR^h$, $-NHCOR^g$, $-NHCONR^gR^h$, $-CONR^gR^h$, $-CO_2R^g$, $-SO_2R^i$, $-OSO_2R^i$, $-COR^g$, $-CR^g=NR^h$ or $-N=CR^gR^h$ in which $R^i$ is $C_{1-4}$ alkyl, halo $(C_{1-4})$alkyl, $C_{1-4}$ alkoxy, halo$(C_{1-4})$alkoxy, $C_{1-4}$ alkylthio, $C_{3-6}$ cycloalkyl, $C_{3-6}$ cycloalkyl$(C_{1-4})$alkyl, phenyl or benzyl, the phenyl and benzyl groups being optionally substituted with halogen, $C_{1-4}$ alkyl or $C_{1-4}$ alkoxy and $R^g$ and $R^h$ are independently hydrogen, $C_{1-4}$alkyl, halo$(C_{1-4})$alkyl, $C_{1-4}$alkoxy, halo$(C_{1-4})$alkoxy, $C_{1-4}$alkylthio, $C_{3-6}$ cycloalkyl, $C_{3-6}$cycloalkyl$(C_{1-4})$alkyl, phenyl or benzyl, the phenyl and benzyl groups being optionally substituted with halogen, $C_{1-4}$alkyl or $C_{1-4}$alkoxy.

Preferred substituents are halo, $C_{1-6}$ alkyl, in particular methyl and ethyl, $C_{2-6}$alkenyl, in particular vinyl and allyl, $C_{2-6}$ alkynyl, in particular ethynyl and propargyl, trialkylsilylethynyl, in particular trimethylsilylethynyl, 3-hydroxy-3- $(C_{1-4}$alkyl$(C_{3-6})$alk-1-yn-1-yl, in particular 3-hydroxy-3-methyl-but-1-yn-1-yl, phenyl), pyridyl, pyrimidinyl and thienyl).

The rings which can be formed by $R^a$ together with $R^b$, or $R^c$ together with $R^d$ together with the carbon atoms to which they are attached are suitably saturated or unsaturated, 3 to 6 membered carbocyclic or heterocyclic rings containing a heteroatom selected from sulfur, oxygen, nitrogen and $NR^o$, wherein $R^o$ is hydrogen or optionally substituted $C_{1-4}$alkyl.

Preferably, in the compounds of the formula (1), $R^a$ and $R^b$, independently of each other, are hydrogen, $C_{1-4}$alkyl, $C_{1-4}$haloalkyl, $C_{1-4}$alkoxy$(C_{1-4})$alkyl, $C_{1-4}$hydroxyalkyl, cyano, $C_{2-4}$ alkynyl, $C_{2-4}$alkenyl or $C_{1-4}$alkoxycarbonyl.

Of particular interest are those compounds of the formula (I), wherein Ar is a radical of the formula

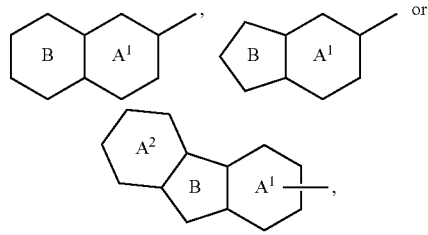

wherein
$A^1$ is optionally substituted phenyl,
$A^2$ is an optionally substituted 6-membered aromatic ring, and
B is a saturated, partially saturated or unsaturated, optionally substituted 5- or 6-membered ring, optionally containing a heteroatom selected from oxygen, sulphur, nitrogen or $NR^o$, wherein $R^o$ is hydrogen or optionally substituted $C_{1-4}$alkyl.

Another group of preferred compounds of the formula (I) are those, wherein B contains 1 or 2 nitrogen atoms or groups NH.

Another group of preferred compounds of the formula (I) are those, wherein Ar is a naphthyl, quinolyl or quinazolinyl ring; more preferably, Ar is a naphth-2-yl, quinol-6-yl or quinozalin-6-yl ring; and in particular Ar is a radical of the formula

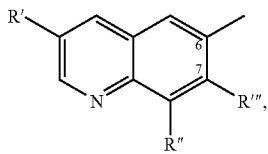

wherein

R' is hydrogen, halogen, $C_{1-4}$alkyl, $C_{2-4}$alkenyl, $C_{2-4}$alkynyl, trialkylsilylethynyl or 3-hydroxy-3-methyl-but-1-yn-1-yl, and R" and R'", independently of each other, are hydrogen, $C_{1-3}$alkyl (in particular methyl) or halogen, or Ar is a radical of the formula

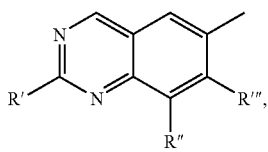

wherein

R' is hydrogen, halogen, $C_{1-4}$alkyl or $C_{2-4}$alkynyl, and

R" and R'", independently of each other, are hydrogen, methyl, ethyl or halogen.

Another group of preferred compounds of the formula (I) are those, wherein Ar is a tetralinyl, tetrahydroquinolyl, dihydrochromenyl, benzoxathiolyl, benzoxadiazolyl, benzisoxazolyl, indolyl, indazolyl, benzodioxolyl, indanyl, benzoxazolyl, benzthiazolyl, benzisothiazolyl, benzimidazolyl, isoindolyl, benztriazolyl, benzthiophenyl, benzofuranyl, isobenzofuranyl, benzodihydrofuranyl or isobenzodihydrofuranyl ring. Preferably, Ar is a benzoxazolyl, benzthiazolyl, benzthiophenyl, benzofuranyl, benzodihydrofuranyl or indanyl ring; and more preferably, Ar is a benzoxazol-6-yl, benzoxazol-5-yl, benzthiazol-6-yl, benzthiazol-5-yl, benzthiophen-6-yl, benzthiophen-5-yl, benzofuran-6-yl, benzofuran-5-yl, benzodihydrofuran-6-yl, benzodihydrofuran-5-yl or indan-5-yl ring; and in particular, Ar is a radical of the formula

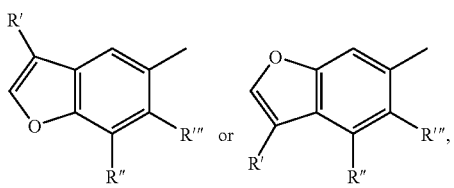

wherein

R' is hydrogen, halogen, $C_{1-4}$ alkyl, $C_{2-4}$alkenyl or $C_{2-4}$alkynyl, and R" and R'", independently of each other, are hydrogen, methyl, ethyl or halogen, or Ar is a radical of the formula

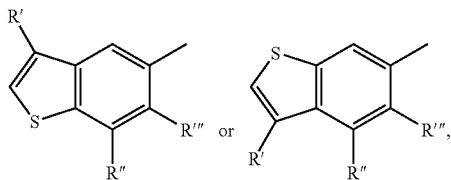

wherein

R' is hydrogen, halogen, $C_{1-4}$alkyl, $C_{2-4}$alkenyl or $C_{2-4}$alkynyl, and R" and R'", independently of each other, are hydrogen, methyl, ethyl or halogen, or Ar is radical of the formula

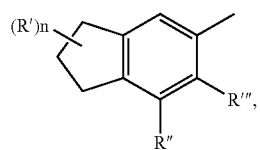

wherein

R' is hydrogen, halogen, $C_{1-4}$alkyl, $C_{2-4}$alkenyl or $C_{2-4}$alkynyl, and n is 0 to 6, and R" and R'", independently of each other, are hydrogen, methyl, ethyl or halogen, or Ar is a radical of the formula

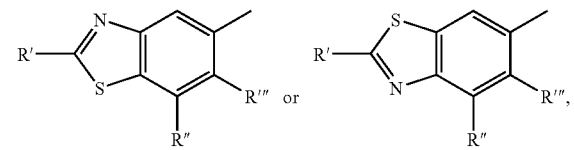

wherein

R' is hydrogen, halogen, $C_{1-4}$alkyl, $C_{2-4}$alkenyl or $C_{2-4}$alkynyl, and R" and R'", independently of each other, are hydrogen, methyl, ethyl or halogen, Preferably, R', R" and R'" are hydrogen.

It is also preferred that R' is hydrogen, R" is hydrogen and R'" is hydrogen, methyl, ethyl or halogen.

It is also preferred that R' is hydrogen, R" is hydrogen or methyl and R'" is methyl.

It should be noted that in the above-shown formulae of Ar the substituents R', R" and R'" can have the meanings assigned to them independently of each other.

Another group of preferred compounds of the formula (I) are those, wherein Ar is a dibenzofuranyl, dibenzothiophenyl, fluorenyl or carbazole ring; preferably, Ar is a dibenzofuran-3-yl, dibenzothiophen-3-yl, fluoren-3-yl or carbazol-3-yl ring.

Another group of preferred compounds of the formula (I) are those, wherein Ar is substituted by halo, cyano, nitro, azido, $C_{1-6}$alkyl, halo($C_{1-6}$)alkyl, $C_{3-6}$ cycloalkyl, $C_{3-6}$ cycloalkyl($C_{1-4}$)alkyl, $C_{2-6}$alkenyl, halo($C_{2-6}$)alkenyl, $C_{2-6}$alkynyl, trialkylsilylethynyl (especially trimethylsilylethynyl), 3-hydroxy-3-$C_{1-4}$alkyl-$C_{3-6}$alk-1-ynyl (especially 3-hydroxy-3-methyl-but-1-ynyl), halo($C_{2-6}$)alkynyl, $C_{1-6}$alkoxy, halo($C_{1-6}$)alkoxy, $C_{2-6}$ alkenyloxy, halo($C_{2-6}$) alkenyloxy, $C_{2-6}$alkynyloxy, halo($C_{2-6}$)alkynyloxy, aryl, aryloxy, aryl-($C_{1-6}$)alkyl, aryl($C_{1-6}$)alkoxy, heteroaryl, heteroaryloxy, heteroaryl($C_{1-6}$)alkyl, heteroaryl-($C_{1-6}$)alkoxy, —SF$_5$, —S(O)$_u$($C_{1-6}$)alkyl wherein u is 0, 1 or 2 and the alkyl group is optionally substituted with halo; —OSO$_2$($C_{1-4}$)alkyl where the alkyl group is optionally substituted with halo; —CONR$^u$R$^v$, —COR$^u$, —CO$_2$R$^u$, —R$^u$=NR$^v$, —NR$^u$R$^v$, —NR$^u$COR$^v$, —NR$^u$CO$_2$R$^v$, —SO$_2$NR$^u$R$^v$ or —NR$^u$SO$_2$R$^w$ where R$^w$ is $C_{1-6}$ alkyl optionally substituted with halogen and R$^u$ and R$^s$ are independently H or $C_{1-6}$ alkyl optionally substituted with halogen; or, in the case of —CONR$^u$R$^v$ or —SO$_2$NR$^u$R$^v$, may join to form a 5- or 6-membered ring containing a single nitrogen atom, a single sulphur atom, saturated carbon atoms and optionally a single oxygen atom; wherein any of the foregoing alkyl, cycloalkyl, alkenyl, alkynyl, aryl or heteroaryl groups or moieties are optionally substituted.

Another group of preferred compounds of the formula (I) are those, wherein A$^1$ is optionally substituted by $C_{1-4}$alkyl or halogen.

Another group of preferred compounds of the formula (I) are those, wherein A$^2$ is optionally substituted by $C_{1-4}$alkyl, in particular methyl or ethyl, or halogen.

Another group of preferred compounds of the formula (I) are those, wherein B is optionally substituted by $C_{1-4}$alkyl, $C_{2-4}$ alkenyl, $C_{2-4}$alkynyl or halogen.

Preferably, B is substituted by $C_{2-4}$alkyl, $C_{2-4}$alkynyl or halogen.

Another group of preferred compounds of the formula (I) are those, wherein R$^1$ is $C_{1-4}$ alkyl, halo($C_{1-4}$)alkyl, $C_{1-4}$alkoxy, halo($C_{1-4}$alkoxy, $C_{1-4}$alkylthio or halo($C_{1-4}$) alkylthio; preferably, R$^1$ is ethyl, methoxy, ethoxy or methylthio.

Another group of preferred compounds of the formula (I) are those, wherein R$^2$ is hydrogen, $C_{1-8}$alkyl, $C_{3-4}$cyclo-alkyl, $C_{2-8}$alkenyl, cyano($C_{1-4}$) alkyl, $C_{1-4}$alkoxy($C_{1-4}$) alkyl, $C_{1-4}$alkoxy($C_{1-4}$) alkoxy($C_{1-4}$) alkyl; preferably, R$^2$ is hydrogen.

Another group of preferred compounds of the formula (I) are those, wherein R$^3$ is hydrogen, optionally substituted $C_{1-4}$alkyl, optionally substituted $C_{3-6}$cycloalkyl which optionally contains an oxygen atom, optionally substituted $C_{2-4}$alkenyl, optionally substituted $C_{2-4}$alkynyl or $C_{1-3}$alkoxy ($C_{1-3}$)-alkylcarbonyl.

More preferably, R$^3$ is hydrogen, $C_{1-4}$alkyl, halo($C_{1-4}$) alkyl, cyano($C_{1-4}$)alkyl, benzyl, $C_{1-3}$alkoxy-($C_{1-3}$)alkylcarbonyl, $C_{3-4}$cycloalkyl, $C_{3-4}$alkenyl or $C_{3-4}$alkynyl.

Particularly preferred R$^3$ is hydrogen, methyl, cyanomethyl, fluoromethyl, ethyl, allyl, propargyl or but-2-yn-4-yl.

Another group of preferred compounds of the formula (I) are those, wherein n is 0.

Another group of preferred compounds of the formula (I) are those, wherein R$^e$ is hydrogen and n is 0.

Another group of preferred compounds of the formula (I) are those, wherein m is 1.

Another group of preferred compounds of the formula (I) are those, wherein R$^e$ is hydrogen and m is 1.

Another group of preferred compounds of the formula (I) are those, wherein m is 1, n is 1, and R$^c$ and R$^d$ are hydrogen.

Another group of preferred compounds of the formula (I) are those, wherein R$^e$ is hydrogen, m is 1, n is 1, and R$^c$ and R$^d$ are hydrogen.

Another group of preferred compounds of the formula (I) are those, wherein m is 1 and n is 0.

Another group of preferred compounds of the formula (I) are those, wherein R$^e$ is hydrogen, m is 1 and n is 0.

Another group of preferred compounds of the formula (I) are those, wherein R$^a$ is hydrogen or methyl, and R$^b$ is hydrogen, methyl, cyano, ethynyl, methoxymethyl, allyloxymethyl or propargyloxymethyl.

Another group of preferred compounds of the formula (I) are those, wherein R$^a$ is methyl, and R$^b$ is methyl, cyano, ethynyl, methoxymethyl, allyloxymethyl or propargyloxymethyl.

Preferably, R$^a$ is methyl, R$^b$ is methyl or cyano.

Or, preferably, R$^a$ is methyl, R$^b$ is methyl or ethynyl.

Or, preferably, R$^a$ is methyl, R$^b$ is methyl or methoxymethyl.

Or, preferably, R$^a$ is methyl, R$^b$ is methyl or propargyloxymethyl.

Or, preferably, R$^a$ is methyl, R$^b$ is methyl.

Another group of preferred compounds of the formula (I) are those, wherein R$^e$ is hydrogen, R$^a$ is hydrogen or methyl, and R$^b$ is hydrogen, methyl, cyano, ethynyl, methoxymethyl, allyloxymethyl or propargyloxymethyl.

Another group of preferred compounds of the formula (I) are those, wherein R$^e$ is methyl and n is 0.

Another group of preferred compounds of the formula (I) are those, wherein R$^e$ is methyl and m is 1.

Another group of preferred compounds of the formula (I) are those, wherein R$^e$ is methyl, m is 1, n is 1, and R$^c$ and R$^d$ are hydrogen.

Another group of preferred compounds of the formula (I) are those, wherein R$^e$ is methyl, m is 1, n is 0, and R$^c$ and R$^d$ are hydrogen.

Another group of preferred compounds of the formula (I) are those, wherein R$^e$ is methyl, R$^a$ is hydrogen or methyl, and R$^b$ is hydrogen, methyl, cyano or ethynyl.

Particularly preferred compounds of the formula (1) are those wherein Ar is a radical of the formula

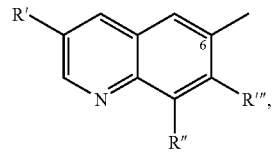

wherein

R' is bromo, iodo or ethynyl, R" is hydrogen, R'" is hydrogen or fluoro,

R$^1$ is ethyl, methoxy or methylthio, R$^2$ is hydrogen, m is 1, R$^a$ and R$^b$, independently of each other, are methyl, methoxymethyl, propargyloxymethyl, ethynyl, formyl or cyano, n is 0, R$^e$ is hydrogen and R$^3$ is hydrogen or methyl.

More preferably, in these compounds, R' is bromo, R" and R'" are hydrogen, R$^1$ is methoxy or methylthio, R$^a$ and R$^b$ methyl and R$^3$ is methyl.

More preferably, in these compounds, R' is iodo, R" and R'" are hydrogen, R$^1$ is methoxy or methylthio, R$^a$ and R$^b$ are methyl and R$^3$ is methyl.

More preferably, in these compounds, R' is ethynyl, R" and R'" are hydrogen, R$^1$ is methoxy or methylthio, R$^a$ and R$^b$ are methyl and R$^3$ is methyl.

Compounds that form part of the invention are illustrated in Tables 1 to 329 below. Melting points (mp) and/or diagnostic molecular ion (eg M$^+$, [M+1]$^+$) values and/or spectroscopic (1H NMR) data are provided in Examples 1, 2, 3 and 4 while biological activities are provided in Example 5.

Compounds of the formula 1a:

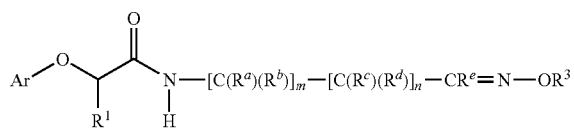
(1a)

TABLE A

Ar of formula 1a defined as Ar1 to Ar83

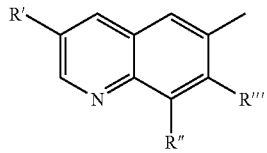

| | R' | R" | R''' |
|---|---|---|---|
| Ar1 | Cl | H | H |
| Ar2 | Cl | F | H |
| Ar3 | Cl | Cl | H |
| Ar4 | Cl | Br | H |
| Ar5 | Cl | I | H |
| Ar6 | Cl | methyl | H |
| Ar7 | Br | H | H |
| Ar8 | Br | F | H |
| Ar9 | Br | Cl | H |
| Ar10 | Br | Br | H |
| Ar11 | Br | I | H |
| Ar12 | Br | methyl | H |
| Ar13 | I | H | H |
| Ar14 | I | F | H |
| Ar15 | I | Cl | H |
| Ar16 | I | Br | H |
| Ar17 | I | I | H |
| Ar18 | I | methyl | H |
| Ar19 | ethynyl | H | H |
| Ar20 | ethynyl | F | H |
| Ar21 | ethynyl | Cl | H |
| Ar22 | ethynyl | Br | H |
| Ar23 | ethynyl | I | H |
| Ar24 | ethynyl | methyl | H |
| Ar25 | propyn-(1)yl | H | H |
| Ar26 | propyn-(1)yl | F | H |
| Ar27 | propyn-(1)yl | Cl | H |
| Ar28 | propyn-(1)yl | Br | H |
| Ar29 | propyn-(1)yl | I | H |
| Ar30 | propyn-(1)yl | methyl | H |
| Ar31 | Cl | H | F |
| Ar32 | Br | H | F |
| Ar33 | I | H | F |
| Ar34 | ethynyl | H | F |
| Ar35 | propyn-(1)-yl | H | F |

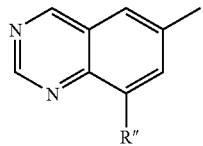

| | R" |
|---|---|
| A36 | H |
| A37 | methyl |

TABLE A-continued

Ar of formula 1a defined as Ar1 to Ar83

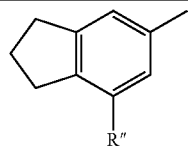

| | R" |
|---|---|
| Ar38 | H |
| Ar39 | methyl |

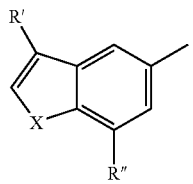

| | R' | R" | X |
|---|---|---|---|
| Ar40 | H | H | O |
| Ar41 | H | methyl | O |
| Ar42 | H | Br | O |
| Ar43 | H | Cl | O |
| Ar44 | Br | H | O |
| Ar45 | Br | methyl | O |
| Ar46 | Br | Cl | O |
| Ar47 | Br | Br | O |
| Ar48 | I | H | O |
| Ar49 | I | methyl | O |
| Ar50 | I | Cl | O |
| Ar51 | I | Br | O |
| Ar52 | ethynyl | H | O |
| Ar53 | ethynyl | methyl | O |
| Ar54 | ethynyl | Cl | O |
| Ar55 | ethynyl | Br | O |
| Ar56 | H | H | S |
| Ar57 | H | methyl | S |
| Ar58 | H | Br | S |
| Ar59 | H | Cl | S |
| Ar60 | Br | H | S |
| Ar61 | Br | methyl | S |
| Ar62 | Br | Cl | S |
| Ar63 | Br | Br | S |
| Ar64 | I | H | S |
| Ar65 | I | methyl | S |
| Ar66 | I | Cl | S |
| Ar67 | I | Br | S |
| Ar68 | ethynyl | H | S |
| Ar69 | ethynyl | methyl | S |
| Ar70 | ethynyl | Cl | S |
| Ar71 | ethynyl | Br | S |

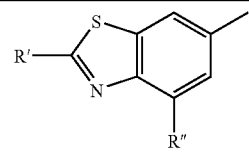

| | R' | R" |
|---|---|---|
| Ar72 | H | H |
| Ar73 | H | methyl |
| Ar74 | H | Cl |
| Ar75 | H | Br |
| Ar76 | methyl | H |
| Ar77 | methyl | methyl |
| Ar78 | methyl | Cl |
| Ar79 | methyl | Br |
| Ar80 | ethynyl | H |
| Ar81 | ethynyl | methyl |
| Ar82 | ethynyl | Cl |
| Ar83 | ethynyl | Br |

TABLE B

R1 of formula 1a defined as S1 to S4

| | |
|---|---|
| S1 | SCH3 |
| S2 | OCH3 |
| S3 | CH2CH3 |
| S4 | SCH2CH3 |

TABLE C $-[C(R^a)(R^b)]_m-[C(R^c)(R^d)]_n-CR^e=N-OR^3$ of formula 1b defined as A1 to A140

| | Ra | Rb | n | Rc | Rd | Re | R3 |
|---|---|---|---|---|---|---|---|
| A1 | methyl | methyl | 0 | — | — | H | methyl |
| A2 | methyl | methyl | 0 | — | — | H | ethyl |
| A3 | methyl | methyl | 0 | — | — | H | allyl |
| A4 | methyl | methyl | 0 | — | — | H | propargyl |
| A5 | methyl | methyl | 0 | — | — | H | H |
| A6 | methyl | methyl | 1 | H | H | H | methyl |
| A7 | methyl | methyl | 1 | H | H | H | ethyl |
| A8 | methyl | methyl | 1 | H | H | H | allyl |
| A9 | methyl | methyl | 1 | H | H | H | propargyl |
| A10 | methyl | methyl | 1 | H | H | H | H |
| A11 | methyl | methyl | 0 | — | — | methyl | methyl |
| A12 | methyl | methyl | 0 | — | — | methyl | ethyl |
| A13 | methyl | methyl | 0 | — | — | methyl | allyl |
| A14 | methyl | methyl | 0 | — | — | methyl | propargyl |
| A15 | methyl | methyl | 0 | — | — | methyl | H |
| A16 | methyl | methyl | 1 | H | H | methyl | methyl |
| A17 | methyl | methyl | 1 | H | H | methyl | ethyl |
| A18 | methyl | methyl | 1 | H | H | methyl | allyl |
| A19 | methyl | methyl | 1 | H | H | methyl | propargyl |
| A20 | methyl | methyl | 1 | H | H | methyl | H |
| A21 | methyl | ethynyl | 0 | — | — | H | methyl |
| A22 | methyl | ethynyl | 0 | — | — | H | ethyl |
| A23 | methyl | ethynyl | 0 | — | — | H | allyl |
| A24 | methyl | ethynyl | 0 | — | — | H | propargyl |
| A25 | methyl | ethynyl | 0 | — | — | H | H |
| A26 | methyl | ethynyl | 1 | H | H | H | methyl |
| A27 | methyl | ethynyl | 1 | H | H | H | ethyl |
| A28 | methyl | ethynyl | 1 | H | H | H | allyl |
| A29 | methyl | ethynyl | 1 | H | H | H | propargyl |
| A30 | methyl | ethynyl | 1 | H | H | H | H |
| A31 | methyl | ethynyl | 0 | — | — | methyl | methyl |
| A32 | methyl | ethynyl | 0 | — | — | methyl | ethyl |
| A33 | methyl | ethynyl | 0 | — | — | methyl | allyl |
| A34 | methyl | ethynyl | 0 | — | — | methyl | propargyl |
| A35 | methyl | ethynyl | 0 | — | — | methyl | H |
| A36 | methyl | ethynyl | 1 | H | H | methyl | methyl |
| A37 | methyl | ethynyl | 1 | H | H | methyl | ethyl |
| A38 | methyl | ethynyl | 1 | H | H | methyl | allyl |
| A39 | methyl | ethynyl | 1 | H | H | methyl | propargyl |
| A40 | methyl | ethynyl | 1 | H | H | methyl | H |
| A41 | methyl | CN | 0 | — | — | H | methyl |
| A42 | methyl | CN | 0 | — | — | H | ethyl |
| A43 | methyl | CN | 0 | — | — | H | allyl |
| A44 | methyl | CN | 0 | — | — | H | propargyl |
| A45 | methyl | CN | 0 | — | — | H | H |
| A46 | methyl | CN | 1 | H | H | H | methyl |
| A47 | methyl | CN | 1 | H | H | H | ethyl |
| A48 | methyl | CN | 1 | H | H | H | allyl |
| A49 | methyl | CN | 1 | H | H | H | propargyl |
| A50 | methyl | CN | 1 | H | H | H | H |
| A51 | methyl | CN | 0 | — | — | methyl | methyl |
| A52 | methyl | CN | 0 | — | — | methyl | ethyl |
| A53 | methyl | CN | 0 | — | — | methyl | allyl |
| A54 | methyl | CN | 0 | — | — | methyl | propargyl |
| A55 | methyl | CN | 0 | — | — | methyl | H |
| A56 | methyl | CN | 1 | H | H | methyl | methyl |
| A57 | methyl | CN | 1 | H | H | methyl | ethyl |
| A58 | methyl | CN | 1 | H | H | methyl | allyl |
| A59 | methyl | CN | 1 | H | H | methyl | propargyl |
| A60 | methyl | CN | 1 | H | H | methyl | H |
| A61 | methyl | CH2F | 0 | — | — | H | methyl |
| A62 | methyl | CH2F | 0 | — | — | H | ethyl |
| A63 | methyl | CH2F | 0 | — | — | H | allyl |
| A64 | methyl | CH2F | 0 | — | — | H | propargyl |
| A65 | methyl | CH2F | 0 | — | — | H | H |
| A66 | methyl | CH2F | 1 | H | H | H | methyl |
| A67 | methyl | CH2F | 1 | H | H | H | ethyl |
| A68 | methyl | CH2F | 1 | H | H | H | allyl |
| A69 | methyl | CH2F | 1 | H | H | H | propargyl |
| A70 | methyl | CH2F | 1 | H | H | H | H |
| A71 | methyl | CH2F | 0 | — | — | methyl | methyl |
| A72 | methyl | CH2F | 0 | — | — | methyl | ethyl |
| A73 | methyl | CH2F | 0 | — | — | methyl | allyl |
| A74 | methyl | CH2F | 0 | — | — | methyl | propargyl |
| A75 | methyl | CH2F | 0 | — | — | methyl | H |
| A76 | methyl | CH2F | 1 | H | H | methyl | methyl |
| A77 | methyl | CH2F | 1 | H | H | methyl | ethyl |
| A78 | methyl | CH2F | 1 | H | H | methyl | allyl |
| A79 | methyl | CH2F | 1 | H | H | methyl | propargyl |
| A80 | methyl | CH2F | 1 | H | H | methyl | H |
| A81 | methyl | CH2Omethyl | 0 | — | — | H | methyl |
| A82 | methyl | CH2Omethyl | 0 | — | — | H | ethyl |
| A83 | methyl | CH2Omethyl | 0 | — | — | H | allyl |
| A84 | methyl | CH2Omethyl | 0 | — | — | H | propargyl |
| A85 | methyl | CH2Omethyl | 0 | — | — | H | H |
| A86 | methyl | CH2Omethyl | 1 | H | H | H | methyl |
| A87 | methyl | CH2Omethyl | 1 | H | H | H | ethyl |
| A88 | methyl | CH2Omethyl | 1 | H | H | H | allyl |
| A89 | methyl | CH2Omethyl | 1 | H | H | H | propargyl |
| A90 | methyl | CH2Omethyl | 1 | H | H | H | H |
| A91 | methyl | CH2Omethyl | 0 | — | — | methyl | methyl |
| A92 | methyl | CH2Omethyl | 0 | — | — | methyl | ethyl |
| A93 | methyl | CH2Omethyl | 0 | — | — | methyl | allyl |
| A94 | methyl | CH2Omethyl | 0 | — | — | methyl | propargyl |
| A95 | methyl | CH2Omethyl | 0 | — | — | methyl | H |
| A96 | methyl | CH2Omethyl | 1 | H | H | methyl | methyl |
| A97 | methyl | CH2Omethyl | 1 | H | H | methyl | ethyl |
| A98 | methyl | CH2Omethyl | 1 | H | H | methyl | allyl |
| A99 | methyl | CH2Omethyl | 1 | H | H | methyl | propargyl |
| A100 | methyl | CH2Omethyl | 1 | H | H | methyl | H |
| A101 | —CH2CH2CH2— | | 0 | — | — | H | methyl |
| A102 | —CH2CH2CH2— | | 0 | — | — | H | ethyl |
| A103 | —CH2CH2CH2— | | 0 | — | — | H | allyl |
| A104 | —CH2CH2CH2— | | 0 | — | — | H | propargyl |
| A105 | —CH2CH2CH2— | | 0 | — | — | H | H |
| A106 | —CH2CH2CH2— | | 1 | H | H | H | methyl |
| A107 | —CH2CH2CH2— | | 1 | H | H | H | ethyl |
| A108 | —CH2CH2CH2— | | 1 | H | H | H | allyl |
| A109 | —CH2CH2CH2— | | 1 | H | H | H | propargyl |
| A110 | —CH2CH2CH2— | | 1 | H | H | H | H |
| A111 | —CH2CH2CH2— | | 0 | — | — | methyl | methyl |
| A112 | —CH2CH2CH2— | | 0 | — | — | methyl | ethyl |
| A113 | —CH2CH2CH2— | | 0 | — | — | methyl | allyl |
| A114 | —CH2CH2CH2— | | 0 | — | — | methyl | propargyl |
| A115 | —CH2CH2CH2— | | 0 | — | — | methyl | H |
| A116 | —CH2CH2CH2— | | 1 | H | H | methyl | methyl |
| A117 | —CH2CH2CH2— | | 1 | H | H | methyl | ethyl |
| A118 | —CH2CH2CH2— | | 1 | H | H | methyl | allyl |
| A119 | —CH2CH2CH2— | | 1 | H | H | methyl | propargyl |
| A120 | —CH2CH2CH2— | | 1 | H | H | methyl | H |
| A121 | —CH2CH2CH2CH2— | | 0 | — | — | H | methyl |
| A122 | —CH2CH2CH2CH2— | | 0 | — | — | H | ethyl |
| A123 | —CH2CH2CH2CH2— | | 0 | — | — | H | allyl |
| A124 | —CH2CH2CH2CH2— | | 0 | — | — | H | propargyl |
| A125 | —CH2CH2CH2CH2— | | 0 | — | — | H | H |
| A126 | —CH2CH2CH2CH2— | | 1 | H | H | H | methyl |
| A127 | —CH2CH2CH2CH2— | | 1 | H | H | H | ethyl |
| A128 | —CH2CH2CH2CH2— | | 1 | H | H | H | allyl |
| A129 | —CH2CH2CH2CH2— | | 1 | H | H | H | propargyl |
| A130 | —CH2CH2CH2CH2— | | 1 | H | H | H | H |
| A131 | —CH2CH2CH2CH2— | | 0 | — | — | methyl | methyl |
| A132 | —CH2CH2CH2CH2— | | 0 | — | — | methyl | ethyl |
| A133 | —CH2CH2CH2CH2— | | 0 | — | — | methyl | allyl |
| A134 | —CH2CH2CH2CH2— | | 0 | — | — | methyl | propargyl |
| A135 | —CH2CH2CH2CH2— | | 0 | — | — | methyl | H |
| A136 | —CH2CH2CH2CH2— | | 1 | H | H | methyl | methyl |
| A137 | —CH2CH2CH2CH2— | | 1 | H | H | methyl | ethyl |
| A138 | —CH2CH2CH2CH2— | | 1 | H | H | methyl | allyl |

TABLE C-continued

—[C(R$^a$)(R$^b$)]$_m$—[C(R$^c$)(R$^d$)]$_n$—CR$^e$=N—OR$^3$ of formula 1b defined as A1 to A140

| | Ra | Rb | n | Rc | Rd | Re | R3 |
|---|---|---|---|---|---|---|---|
| A139 | —CH2CH2CH2CH2— | | 1 | H | H | methyl | propargyl |
| A140 | —CH2CH2CH2CH2— | | 1 | H | H | methyl | H |

Table 1

Table 1 contains compounds of formula 1a with Ar is Ar1 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 2

Table 2 contains compounds of formula 1a with Ar is Ar1 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 3

Table 3 contains compounds of formula 1a with Ar is Ar1 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 4

Table 4 contains compounds of formula 1a with Ar is Ar1 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 5

Table 5 contains compounds of formula 1a with Ar is Ar2 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 6

Table 6 contains compounds of formula 1a with Ar is Ar2 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 7

Table 7 contains compounds of formula 1a with Ar is Ar2 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 8

Table 8 contains compounds of formula 1a with Ar is Ar2 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 9

Table 9 contains compounds of formula 1a with Ar is Ar3 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 10

Table 10 contains compounds of formula 1a with Ar is Ar3 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 11

Table 11 contains compounds of formula 1a with Ar is Ar3 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 12

Table 12 contains compounds of formula 1a with Ar is Ar3 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 13

Table 13 contains compounds of formula 1a with Ar is Ar4 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 14

Table 14 contains compounds of formula 1a with Ar is Ar4 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 15

Table 15 contains compounds of formula 1a with Ar is Ar4 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 16

Table 16 contains compounds of formula 1a with Ar is Ar4 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 17

Table 17 contains compounds of formula 1a with Ar is Ar5 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 18

Table 18 contains compounds of formula 1a with Ar is Ar5 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 19

Table 19 contains compounds of formula 1a with Ar is Ar5 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 20

Table 20 contains compounds of formula 1a with Ar is Ar5 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 21

Table 21 contains compounds of formula 1a with Ar is Ar6 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 22

Table 22 contains compounds of formula 1a with Ar is Ar6 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 23

Table 23 contains compounds of formula 1a with Ar is Ar6 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 24

Table 24 contains compounds of formula 1a with Ar is Ar6 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 25

Table 25 contains compounds of formula 1a with Ar is Ar7 of table A, R1 is S1 of table B and —[C(R$^a$)(R$^{13}$)]$_m$—[C(R$^c$)(R$^d$)]$_n$—CR$^e$=N—OR$^3$ is A1 to A140 of table C.

Table 26

Table 26 contains compounds of formula 1a with Ar is Ar7 of table A, R1 is S2 of table B and —[C($R^a$)($R^b$)]$_m$—[C($R^c$)($R^d$)]$_n$—C$R^e$=N—O$R^3$ is A1 to A140 of table C.

Table 27

Table 27 contains compounds of formula 1a with Ar is Ar7 of table A, R1 is S3 of table B and —[C($R^a$)($R^b$)]$_m$—[C($R^c$)($R^d$)]$_n$—C$R^e$=N—O$R^3$ is A1 to A140 of table C.

Table 28

Table 28 contains compounds of formula 1a with Ar is Ar7 of table A, R1 is S4 of table B and —[C($R^a$)($R^b$)]$_m$—[C($R^c$)($R^d$)]$_n$—C$R^e$=N—O$R^3$ is A1 to A140 of table C.

Table 29

Table 29 contains compounds of formula 1a with Ar is Ar8 of table A, R1 is S1 of table B and —[C($R^a$)($R^b$)]$_m$—[C($R^c$)($R^d$)]$_n$—C$R^e$=N—O$R^3$ is A1 to A140 of table C.

Table 30

Table 30 contains compounds of formula 1a with Ar is Ar8 of table A, R1 is S2 of table B and —[C($R^a$)($R^b$)]$_m$—[C($R^c$)($R^d$)]$_n$—C$R^e$=N—O$R^3$ is A1 to A140 of table C.

Table 31

Table 31 contains compounds of formula 1a with Ar is Ar8 of table A, R1 is S3 of table B and —[C($R^a$)($R^b$)]$_m$—[C($R^c$)($R^d$)]$_n$—C$R^e$=N—O$R^3$ is A1 to A140 of table C.

Table 32

Table 32 contains compounds of formula 1a with Ar is Ar8 of table A, R1 is S4 of table B and —[C($R^a$)($R^b$)]$_m$—[C($R^c$)($R^d$)]$_n$—C$R^e$=N—O$R^3$ is A1 to A140 of table C.

Table 33

Table 33 contains compounds of formula 1a with Ar is Ar9 of table A, R1 is S1 of table B and —[C($R^a$)($R^b$)]$_m$—[C($R^c$)($R^d$)]$_n$—C$R^e$=N—O$R^3$ is A1 to A140 of table C.

Table 34

Table 34 contains compounds of formula 1a with Ar is Ar9 of table A, R1 is S2 of table B and —[C($R^a$)($R^b$)]$_m$—[C($R^c$)($R^d$)]$_n$—C$R^e$=N—O$R^3$ is A1 to A140 of table C.

Table 35

Table 35 contains compounds of formula 1a with Ar is Ar9 of table A, R1 is S3 of table B and —[C($R^a$)($R^b$)]$_m$—[C($R^c$)($R^d$)]$_n$—C$R^e$=N—O$R^3$ is A1 to A140 of table C.

Table 36

Table 36 contains compounds of formula 1a with Ar is Ar9 of table A, R1 is S4 of table B and —[C($R^a$)($R^b$)]$_m$—[C($R^c$)($R^d$)]$_n$—C$R^e$=N—O$R^3$ is A1 to A140 of table C.

Table 37

Table 37 contains compounds of formula 1a with Ar is Ar10 of table A, R1 is S1 of table B and —[C($R^a$)($R^b$)]$_m$—[C($R^c$)($R^d$)]$_n$—C$R^e$=N—O$R^3$ is A1 to A140 of table C.

Table 38

Table 38 contains compounds of formula 1a with Ar is Ar10 of table A, R1 is S2 of table B and —[C($R^a$)($R^b$)]$_m$—[C($R^c$)($R^d$)]$_n$—C$R^a$=N—O$R^3$ is A1 to A140 of table C.

Table 39

Table 39 contains compounds of formula 1a with Ar is Ar10 of table A, R1 is S3 of table B and —[C($R^a$)($R^b$)]$_m$—[C($R^c$)($R^d$)]$_n$—C$R^e$=N—O$R^3$ is A1 to A140 of table C.

Table 40

Table 40 contains compounds of formula 1a with Ar is Ar10 of table A, R1 is S4 of table B and —[C($R^a$)($R^b$)]$_m$—[C($R^c$)($R^d$)]$_n$—C$R^e$=N—O$R^3$ is A1 to A140 of table C.

Table 41

Table 41 contains compounds of formula 1a with Ar is Ar11 of table A, R1 is S1 of table B and —[C($R^a$)($R^b$)]$_m$—[C($R^c$)($R^d$)]$_n$—C$R^e$=N—O$R^3$ is A1 to A140 of table C.

Table 42

Table 42 contains compounds of formula 1a with Ar is Ar11 of table A, R1 is S2 of table B and —[C($R^a$)($R^b$)]$_m$—[C($R^c$)($R^d$)]$_n$—C$R^e$=N—O$R^3$ is A1 to A140 of table C.

Table 43

Table 43 contains compounds of formula 1a with Ar is Ar11 of table A, R1 is S3 of table B and —[C($R^a$)($R^b$)]$_m$—[C($R^c$)($R^d$)]$_n$—C$R^e$=N—O$R^3$ is A1 to A140 of table C.

Table 44

Table 44 contains compounds of formula 1a with Ar is Ar11 of table A, R1 is S4 of table B and —[C($R^a$)($R^b$)]$_m$—[C($R^c$)($R^d$)]$_n$—C$R^e$=N—O$R^3$ is A1 to A140 of table C.

Table 45

Table 45 contains compounds of formula 1a with Ar is Ar12 of table A, R1 is S1 of table B and —[C($R^a$)($R^b$)]$_m$—[C($R^c$)($R^d$)]$_n$—C$R^e$=N—O$R^3$ is A1 to A140 of table C.

Table 46

Table 46 contains compounds of formula 1a with Ar is Ar12 of table A, R1 is S2 of table B and —[C($R^a$)($R^b$)]$_m$—[C($R^c$)($R^d$)]$_n$—C$R^e$=N—O$R^3$ is A1 to A140 of table C.

Table 47

Table 47 contains compounds of formula 1a with Ar is Ar12 of table A, R1 is S3 of table B and —[C($R^a$)($R^b$)]$_m$—[C($R^c$)($R^d$)]$_n$—C$R^e$=N—O$R^3$ is A1 to A140 of table C.

Table 48

Table 48 contains compounds of formula 1a with Ar is Ar12 of table A, R1 is S4 of table B and —[C($R^a$)($R^b$)]$_m$—[C($R^c$)($R^d$)]$_n$—C$R^e$=N—O$R^3$ is A1 to A140 of table C.

Table 49

Table 49 contains compounds of formula 1a with Ar is Ar13 of table A, R1 is S1 of table B and —[C($R^a$)($R^b$)]$_m$—[C($R^c$)($R^d$)]$_n$—C$R^e$=N—O$R^3$ is A1 to A140 of table C.

Table 50 contains compounds of formula 1a with Ar is Ar13 of table A, R1 is S2 of table B and —[C($R^a$)($R^b$)]$_m$—[C($R^c$)($R^d$)]$_n$—C$R^e$=N—O$R^3$ is A1 to A140 of table C.

Table 51

Table 51 contains compounds of formula 1a with Ar is Ar13 of table A, R1 is S3 of table B and —[C($R^a$)($R^b$)]$_m$—[C($R^c$)($R^d$)]$_n$—C$R^e$=N—O$R^3$ is A1 to A140 of table C.

Table 52

Table 52 contains compounds of formula 1a with Ar is Ar13 of table A, R1 is S4 of table B and —[C($R^a$)($R^b$)]$_m$—[C($R^c$)($R^d$)]$_n$—C$R^e$=N—O$R^3$ is A1 to A140 of table C.

Table 53

Table 53 contains compounds of formula 1a with Ar is Ar14 of table A, R1 is S1 of table B and —[C($R^a$)($R^b$)]$_m$—[C($R^c$)($R^d$)]$_n$—C$R^e$=N—O$R^3$ is A1 to A140 of table C.

Table 54

Table 54 contains compounds of formula 1a with Ar is Ar14 of table A, R1 is S2 of table B and —[C($R^a$)($R^b$)]$_m$—[C($R^c$)($R^d$)]$_n$—C$R^e$=N—O$R^3$ is A1 to A140 of table C.

Table 55

Table 55 contains compounds of formula 1a with Ar is Ar14 of table A, R1 is S3 of table B and —[C($R^a$)($R^b$)]$_m$—[C($R^c$)($R^d$)]$_n$—C$R^e$=N—O$R^3$ is A1 to A140 of table C.

Table 56

Table 56 contains compounds of formula 1a with Ar is Ar14 of table A, R1 is S4 of table B and —[C($R^a$)($R^b$)]$_m$—[C($R^c$)($R^d$)]$_n$—C$R^e$=N—O$R^3$ is A1 to A140 of table C.

Table 57
Table 57 contains compounds of formula 1a with Ar is Ar15 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 58
Table 58 contains compounds of formula 1a with Ar is Ar15 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 59
Table 59 contains compounds of formula 1a with Ar is Ar15 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 60
Table 60 contains compounds of formula 1a with Ar is Ar15 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 61
contains compounds of formula 1a with Ar is Ar16 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 62
Table 62 contains compounds of formula 1a with Ar is Ar16 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 63
Table 63 contains compounds of formula 1a with Ar is Ar16 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 64
Table 64 contains compounds of formula 1a with Ar is Ar16 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 65
contains compounds of formula 1a with Ar is Ar17 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 66
contains compounds of formula 1a with Ar is Ar17 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 67
contains compounds of formula 1a with Ar is Ar17 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 68
contains compounds of formula 1a with Ar is Ar17 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 69
contains compounds of formula 1a with Ar is Ar18 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 70
Table 70 contains compounds of formula 1a with Ar is Ar18 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 71
Table 71 contains compounds of formula 1a with Ar is Ar18 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 72
Table 72 contains compounds of formula 1a with Ar is Ar18 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 73
Table 73 contains compounds of formula 1a with Ar is Ar19 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 74
Table 74 contains compounds of formula 1a with Ar is Ar19 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 75
Table 75 contains compounds of formula 1a with Ar is Ar19 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 76
Table 76 contains compounds of formula 1a with Ar is Ar19 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 77
Table 77 contains compounds of formula 1a with Ar is Ar20 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 78
Table 78 contains compounds of formula 1a with Ar is Ar20 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 79
Table 79 contains compounds of formula 1a with Ar is Ar20 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 80
Table 80 contains compounds of formula 1a with Ar is Ar20 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 81
Table 81 contains compounds of formula 1a with Ar is Ar21 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 82
Table 82 contains compounds of formula 1a with Ar is Ar21 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 83
Table 83 contains compounds of formula 1a with Ar is Ar21 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 84
Table 84 contains compounds of formula 1a with Ar is Ar21 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 85
Table 85 contains compounds of formula 1a with Ar is Ar22 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 86
Table 86 contains compounds of formula 1a with Ar is Ar22 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 87
Table 87 contains compounds of formula 1a with Ar is Ar22 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 88
Table 88 contains compounds of formula 1a with Ar is Ar22 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 89
Table 89 contains compounds of formula 1a with Ar is Ar23 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 90
Table 90 contains compounds of formula 1a with Ar is Ar23 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 91
Table 91 contains compounds of formula 1a with Ar is Ar23 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 92
Table 92 contains compounds of formula 1a with Ar is Ar23 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 93
Table 93 contains compounds of formula 1a with Ar is Ar24 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 94
Table 94 contains compounds of formula 1a with Ar is Ar24 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 95
Table 95 contains compounds of formula 1a with Ar is Ar24 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 96
Table 96 contains compounds of formula 1a with Ar is Ar24 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 97
Table 97 contains compounds of formula 1a with Ar is Ar25 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 98
Table 98 contains compounds of formula 1a with Ar is Ar25 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 99
Table 99 contains compounds of formula 1a with Ar is Ar25 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 100
Table 100 contains compounds of formula 1a with Ar is Ar25 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 101
Table 101 contains compounds of formula 1a with Ar is Ar26 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 102
Table 102 contains compounds of formula 1a with Ar is Ar26 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 103
Table 103 contains compounds of formula 1a with Ar is Ar26 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 104
Table 104 contains compounds of formula 1a with Ar is Ar26 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 105
Table 105 contains compounds of formula 1a with Ar is Ar27 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 106
Table 106 contains compounds of formula 1a with Ar is Ar27 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 107
Table 107 contains compounds of formula 1a with Ar is Ar27 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 108
Table 108 contains compounds of formula 1a with Ar is Ar27 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 109
Table 109 contains compounds of formula 1a with Ar is Ar28 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 110
Table 110 contains compounds of formula 1a with Ar is Ar28 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 111
Table 111 contains compounds of formula 1a with Ar is Ar28 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 112
Table 112 contains compounds of formula 1a with Ar is Ar28 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 113
Table 113 contains compounds of formula 1a with Ar is Ar29 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 114
Table 114 contains compounds of formula 1a with Ar is Ar29 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 115
Table 115 contains compounds of formula 1a with Ar is Ar29 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 116
Table 116 contains compounds of formula 1a with Ar is Ar29 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 117
Table 117 contains compounds of formula 1a with Ar is Ar30 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 118
Table 118 contains compounds of formula 1a with Ar is Ar30 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 119
Table 119 contains compounds of formula 1a with Ar is Ar30 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 120
Table 120 contains compounds of formula 1a with Ar is Ar30 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 120
  Table 120 contains compounds of formula 1a with Ar is Ar31 of table A, R1 is S2 of table B and —[C(R$^a$)(R$^b$)]$_m$—[C(R$^c$)(R$^d$)]$_n$—CR$^e$═N—OR$^3$ is A1 to A140 of table C.
Table 123
  Table 123 contains compounds of formula 1a with Ar is Ar31 of table A, R1 is S3 of table B and —[C(R$^a$)(R$^b$)]$_m$—[C(R$^c$)(R$^d$)]$_n$—CR$^e$═N—OR$^3$ is A1 to A140 of table C.
Table 124
  Table 124 contains compounds of formula 1a with Ar is Ar32 of table A, R1 is S2 of table B and —[C(R$^a$)(R$^b$)]$_m$—[C(R$^c$)(R$^d$)]$_n$—CR$^e$═N—OR$^3$ is A1 to A140 of table C.
Table 125
  Table 125 contains compounds of formula 1a with Ar is Ar32 of table A, R1 is S3 of table B and —[C(R$^a$)(R$^b$)]$_m$—[C(R$^c$)(R$^d$)]$_n$—CR$^e$═N—OR$^3$ is A1 to A140 of table C.
Table 127
  Table 127 contains compounds of formula 1a with Ar is Ar33 of table A, R1 is S2 of table B and —[C(R$^a$)(R$^b$)]$_m$—[C(R$^c$)(R$^d$)]$_n$—CR$^e$═N—OR$^3$ is A1 to A140 of table C.
  Table 128 contains compounds of formula 1a with Ar is Ar33 of table A, R1 is S3 of table B and —[C(R$^a$)(R$^b$)]$_m$—[C(R$^c$)(R$^d$)]$_n$—CR$^e$═N—OR$^3$ is A1 to A140 of table C.
  Table 131 contains compounds of formula 1a with Ar is Ar34 of table A, R1 is S2 of table B and —[C(R$^a$)(R$^b$)]$_m$—[C(R$^c$)(R$^d$)]$_n$—CR$^e$═N—OR$^3$ is A1 to A140 of table C.
  Table 132 contains compounds of formula 1a with Ar is Ar34 of table A, R1 is S3 of table B and —[C(R$^a$)(R$^b$)]$_m$—[C(R$^c$)(R$^d$)]$_n$—CR$^e$═N—OR$^3$ is A1 to A140 of table C.
  Table 135 contains compounds of formula 1a with Ar is Ar35 of table A, R1 is S2 of table B and —[C(R$^a$)(R$^b$)]$_m$—[C(R$^c$)(R$^d$)]$_n$—CR$^e$═N—OR$^3$ is A1 to A140 of table C.
  Table 136 contains compounds of formula 1a with Ar is Ar35 of table A, R1 is S3 of table B and —[C(R$^a$)(R$^b$)]$_n$—[C(R$^c$)(R$^d$)]$_n$—CR$^e$═N—OR$^3$ is A1 to A140 of table C.
  Table 138 contains compounds of formula 1a with Ar is Ar36 of table A, R1 is S1 of table B and —[C(R$^a$)(R$^b$)]$_m$—[C(R$^c$)(R$^d$)]$_n$—CR$^e$═N—OR$^3$ is A1 to A140 of table C.
  Table 139 contains compounds of formula 1a with Ar is Ar36 of table A, R1 is S2 of table B and —[C(R$^a$)(R$^b$)]$_m$—[C(R$^c$)(R$^d$)]$_n$—CR$^e$═N—OR$^3$ is A1 to A140 of table C.
  Table 140 contains compounds of formula 1a with Ar is Ar36 of table A, R1 is S3 of table B and —[C(R$^a$)(R$^b$)]$_m$—[C(R$^c$)(R$^d$)]$_n$—CR$^e$═N—OR$^3$ is A1 to A140 of table C.
  Table 141 contains compounds of formula 1a with Ar is Ar36 of table A, R1 is S4 of table B and —[C(R$^a$)(R$^b$)]$_m$—[C(R$^c$)(R$^d$)]$_n$—CR$^e$═N—OR$^3$ is A1 to A140 of table C.
  Table 142 contains compounds of formula 1a with Ar is Ar37 of table A, R1 is S1 of table B and —[C(R$^a$)(R$^b$)]$_m$—[C(R$^c$)(R$^d$)]$_n$—CR$^e$═N—OR$^3$ is A1 to A140 of table C.
  Table 143 contains compounds of formula 1a with Ar is Ar37 of table A, R1 is S2 of table and —[C(R$^a$)(R$^b$)]$_m$—[C(R$^c$)(R$^d$)]$_n$—CR$^e$═N—OR$^3$ is A1 to A140 of table C.
  Table 144 contains compounds of formula 1a with Ar is Ar37 of table A, R1 is S3 of table B and —[C(R$^a$)(R$^b$)]$_m$—[C(R$^c$)(R$^d$)]$_n$—CR$^e$═N—OR$^3$ is A1 to A140 of table C.
  Table 145 contains compounds of formula 1a with Ar is Ar37 of table A, R1 is S4 of table B and —[C(R$^a$)(R$^b$)]$_m$—[C(R$^c$)(R$^d$)]$_n$—CR$^e$═N—OR$^3$ is A1 to A140 of table C.
  Table 146 contains compounds of formula 1a with Ar is Ar38 of table A, R1 is S1 of table B and —[C(R$^a$)(R$^b$)]$_m$—[C(R$^c$)(R$^d$)]$_n$—CR$^e$═N—OR$^3$ is A1 to A140 of table C.
  Table 147 contains compounds of formula 1a with Ar is Ar38 of table A, R1 is S2 of table B and —[C(R$^a$)(R$^b$)]$_m$—[C(R$^c$)(R$^d$)]$_n$—CR$^e$═N—OR$^3$ is A1 to A140 of table C.
  Table 148 contains compounds of formula 1a with Ar is Ar38 of table A, R1 is S3 of table B and —[C(R$^a$)(R$^b$)]$_m$—[C(R$^c$)(R$^d$)]$_n$—CR$^e$═N—OR$^3$ is A1 to A140 of table C.
  Table 149 contains compounds of formula 1a with Ar is Ar38 of table A, R1 is S4 of table B and —[C(R$^a$)(R$^b$)]$_m$—[C(R$^c$)(R$^d$)]$_n$—CR$^e$═N—OR$^3$ is A1 to A140 of table C.
  Table 150 contains compounds of formula 1a with Ar is Ar39 of table A, R1 is S1 of table B and —[C(R$^a$)(R$^b$)]$_m$—[C(R$^c$)(R$^d$)]$_n$—CR$^e$═N—OR$^3$ is A1 to A140 of table C.
  Table 151 contains compounds of formula 1a with Ar is Ar39 of table A, R1 is S2 of table B and —[C(R$^a$)(R$^b$)]$_m$—[C(R$^c$)(R$^d$)]$_b$—CR$^e$═N—OR$^3$ is A1 to A140 of table C.
  Table 152 contains compounds of formula 1a with Ar is Ar39 of table A, R1 is S3 of table B and —[C(R$^a$)(R$^b$)]$_m$—[C(R$^c$)(R$^d$)]$_n$—CR$^e$═N—OR$^3$ is A1 to A140 of table C.
  Table 153 contains compounds of formula 1a with Ar is Ar39 of table A, R1 is S4 of table B and —[C(R$^a$)(R$^b$)]$_m$—[C(R$^c$)(R$^d$)]$_n$—CR$^e$═N—OR$^3$ is A1 to A140 of table C.
  Table 154 contains compounds of formula 1a with Ar is Ar40 of table A, R1 is S1 of table B and —[C(R$^a$)(R$^b$)]$_m$—[C(R$^c$)(R$^d$)]$_n$—CR$^e$═N—OR$^3$ is A1 to A140 of table C.
  Table 155 contains compounds of formula 1a with Ar is Ar40 of table A, R1 is S2 of table B and —[C(R$^a$)(R$^b$)]$_m$—[C(R$^c$)(R$^d$)]$_n$—CR$^e$═N—OR$^3$ is A1 to A140 of table C.
  Table 156 contains compounds of formula 1a with Ar is Ar40 of table A, R1 is S3 of table B and —[C(R$^a$)(R$^b$)]$_m$—[C(R$^c$)(R$^d$)]$_n$—CR$^e$═N—OR$^3$ is A1 to A140 of table C.
  Table 157 contains compounds of formula 1a with Ar is Ar40 of table A, R1 is S4 of table B and —[C(R$^a$)(R$^b$)]$_m$—[C(R$^c$)(R$^d$)]$_n$—CR$^e$═N—OR$^3$ is A1 to A140 of table C.
  Table 158 contains compounds of formula 1a with Ar is Ar41 of table A, R1 is S1 of table B and —[C(R$^a$)(R$^b$)]$_m$—[C(R$^c$)(R$^d$)]$_n$—CR$^e$═N—OR$^3$ is A1 to A140 of table C.
  Table 159 contains compounds of formula 1a with Ar is Ar41 of table A, R1 is S2 of table B and —[C(R$^a$)(R$^b$)]$_m$—[C(R$^c$)(R$^d$)]$_n$—CR$^e$═N—OR$^3$ is A1 to A140 of table C.
  Table 160 contains compounds of formula 1a with Ar is Ar41 of table A, R1 is S3 of table B and —[C(R$^a$)(R$^b$)]$_m$—[C(R$^c$)(R$^d$)]$_n$—CR$^e$═N—OR$^3$ is A1 to A140 of table C.
  Table 161 contains compounds of formula 1a with Ar is Ar41 of table A, R1 is S4 of table B and —[C(R$^a$)(R$^b$)]$_m$—[C(R$^c$)(R$^d$)]$_n$—CR$^e$═N—OR$^3$ is A1 to A140 of table C.
  Table 162 contains compounds of formula 1a with Ar is Ar42 of table A, R1 is S1 of table B and —[C(R$^a$)(R$^b$)]$_m$—[C(R$^c$)(R$^d$)]$_n$—CR$^e$═N—OR$^3$ is A1 to A140 of table C.
  Table 163 contains compounds of formula 1a with Ar is Ar42 of table A, R1 is S2 of table B and —[C(R$^a$)(R$^b$)]$_m$—[C(R$^c$)(R$^d$)]$_n$—CR$^e$═N—OR$^3$ is A1 to A140 of table C.
  Table 164 contains compounds of formula 1a with Ar is Ar42 of table A, R1 is S3 of table B and —[C(R$^a$)(R$^b$)]$_m$—[C(R$^c$)(R$^d$)]$_n$—CR$^e$═N—OR$^3$ is A1 to A140 of table C.
  Table 165 contains compounds of formula 1a with Ar is Ar42 of table A, R1 is S4 of table B and —[C(R$^a$)(R$^b$)]$_m$—[C(R$^c$)(R$^d$)]$_n$—CR$^e$═N—OR$^3$ is A1 to A140 of table C.
  Table 166 contains compounds of formula 1a with Ar is Ar43 of table A, R1 is S1 of table B and —[C(R$^a$)(R$^b$)]$_m$—[C(R$^c$)(R$^d$)]$_n$—CR$^e$═N—OR$^3$ is A1 to A140 of table C.
  Table 167 contains compounds of formula 1a with Ar is Ar43 of table A, R1 is S2 of table B and —[C(R$^a$)(R$^b$)]$_m$—[C(R$^c$)(R$^d$)]$_n$—CR$^e$═N—OR$^3$ is A1 to A140 of table C.
  Table 168 contains compounds of formula 1a with Ar is Ar43 of table A, R1 is S3 of table B and —[C(R$^a$)(R$^b$)]$_m$—[C(R$^c$)(R$^d$)]$_n$—CR$^e$═N—OR$^3$ is A1 to A140 of table C.
  Table 169 contains compounds of formula 1a with Ar is Ar43 of table A, R1 is S4 of table B and —[C(R$^a$)(R$^b$)]$_m$—[C(R$^c$)(R$^d$)]$_n$—CR$^e$═N—OR$^3$ is A1 to A140 of table C.

Table 170 contains compounds of formula 1a with Ar is Ar44 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 171 contains compounds of formula 1a with Ar is Ar44 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 172 contains compounds of formula 1a with Ar is Ar44 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 173 contains compounds of formula 1a with Ar is Ar44 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 174 contains compounds of formula 1a with Ar is Ar45 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 175 contains compounds of formula 1a with Ar is Ar45 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 176 contains compounds of formula 1a with Ar is Ar45 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 177 contains compounds of formula 1a with Ar is Ar45 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 178 contains compounds of formula 1a with Ar is Ar46 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 179 contains compounds of formula 1a with Ar is Ar46 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 180 contains compounds of formula 1a with Ar is Ar46 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 181 contains compounds of formula 1a with Ar is Ar46 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 182 contains compounds of formula 1a with Ar is Ar47 of table A, R1 is S1 of table B and —[C(R$^a$)(R$^b$)]$_m$[C(R$^c$)(R$^d$)]$_n$—CR$^e$=N—OR$^3$ is A1 to A140 of table C.

Table 183 contains compounds of formula 1a with Ar is Ar47 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 184 contains compounds of formula 1a with Ar is Ar47 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 185 contains compounds of formula 1a with Ar is Ar47 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 186 contains compounds of formula 1a with Ar is Ar48 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 187 contains compounds of formula 1a with Ar is Ar48 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 188 contains compounds of formula 1a with Ar is Ar48 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 189 contains compounds of formula 1a with Ar is Ar48 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 190 contains compounds of formula 1a with Ar is Ar49 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 191 contains compounds of formula 1a with Ar is Ar49 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 192 contains compounds of formula 1a with Ar is Ar49 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 193 contains compounds of formula 1a with Ar is Ar49 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 194 contains compounds of formula 1a with Ar is Ar50 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 195 contains compounds of formula 1a with Ar is Ar50 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 196 contains compounds of formula 1a with Ar is Ar50 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 197 contains compounds of formula 1a with Ar is Ar50 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 198 contains compounds of formula 1a with Ar is Ar51 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 199 contains compounds of formula 1a with Ar is Ar51 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 200 contains compounds of formula 1a with Ar is Ar51 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 201 contains compounds of formula 1a with Ar is Ar51 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 202 contains compounds of formula 1a with Ar is Ar52 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 203 contains compounds of formula 1a with Ar is Ar52 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 204 contains compounds of formula 1a with Ar is Ar52 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 205 contains compounds of formula 1a with Ar is Ar52 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 206 contains compounds of formula 1a with Ar is Ar53 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 207 contains compounds of formula 1a with Ar is Ar53 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 208 contains compounds of formula 1a with Ar is Ar53 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 209 contains compounds of formula 1a with Ar is Ar53 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 210 contains compounds of formula 1a with Ar is Ar54 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 211 contains compounds of formula 1a with Ar is Ar54 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 212 contains compounds of formula 1a with Ar is Ar54 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 213 contains compounds of formula 1a with Ar is Ar54 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 214 contains compounds of formula 1a with Ar is Ar55 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 215 contains compounds of formula 1a with Ar is Ar55 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 216 contains compounds of formula 1a with Ar is Ar55 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 217 contains compounds of formula 1a with Ar is Ar55 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 218 contains compounds of formula 1a with Ar is Ar56 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 219 contains compounds of formula 1a with Ar is Ar56 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 220 contains compounds of formula 1a with Ar is Ar56 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 221 contains compounds of formula 1a with Ar is Ar56 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 222 contains compounds of formula 1a with Ar is Ar57 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 223 contains compounds of formula 1a with Ar is Ar57 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 224 contains compounds of formula 1a with Ar is Ar57 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 225 contains compounds of formula 1a with Ar is Ar57 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 226 contains compounds of formula 1a with Ar is Ar58 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 227 contains compounds of formula 1a with Ar is Ar58 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 228 contains compounds of formula 1a with Ar is Ar58 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 229 contains compounds of formula 1a with Ar is Ar58 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 230 contains compounds of formula 1a with Ar is Ar59 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 231 contains compounds of formula 1a with Ar is Ar59 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 232 contains compounds of formula 1a with Ar is Ar59 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 233 contains compounds of formula 1a with Ar is Ar59 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 234 contains compounds of formula 1a with Ar is Ar60 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 235 contains compounds of formula 1a with Ar is Ar60 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 236 contains compounds of formula 1a with Ar is Ar60 of table A, R1 is S3 of table B and —[C(R$^a$)(R$^b$)]$_m$—[C(R$^c$)(R$^d$)]$_n$—CR$^e$=-N—OR$^3$ is A1 to A140 of table C.

Table 237 contains compounds of formula 1a with Ar is Ar60 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 238 contains compounds of formula 1a with Ar is Ar61 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 239 contains compounds of formula 1a with Ar is Ar61 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 240 contains compounds of formula 1a with Ar is Ar61 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 241 contains compounds of formula 1a with Ar is Ar61 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 242 contains compounds of formula 1a with Ar is Ar62 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 243 contains compounds of formula 1a with Ar is Ar62 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 244 contains compounds of formula 1a with Ar is Ar62 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 245 contains compounds of formula 1a with Ar is Ar62 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 246 contains compounds of formula 1a with Ar is Ar63 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 247 contains compounds of formula 1a with Ar is Ar63 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 248 contains compounds of formula 1a with Ar is Ar63 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 249 contains compounds of formula 1a with Ar is Ar63 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 250 contains compounds of formula 1a with Ar is Ar64 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 251 contains compounds of formula 1a with Ar is Ar64 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 252 contains compounds of formula 1a with Ar is Ar64 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 253 contains compounds of formula 1a with Ar is Ar64 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 254 contains compounds of formula 1a with Ar is Ar65 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 255 contains compounds of formula 1a with Ar is Ar65 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 256 contains compounds of formula 1a with Ar is Ar65 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 257 contains compounds of formula 1a with Ar is Ar65 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 258 contains compounds of formula 1a with Ar is Ar66 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 259 contains compounds of formula 1a with Ar is Ar66 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 260 contains compounds of formula 1a with Ar is Ar66 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 261 contains compounds of formula 1a with Ar is Ar66 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 262 contains compounds of formula 1a with Ar is Ar67 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 263 contains compounds of formula 1a with Ar is Ar67 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 264 contains compounds of formula 1a with Ar is Ar67 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 265 contains compounds of formula 1a with Ar is Ar67 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 266 contains compounds of formula 1a with Ar is Ar68 of table A, R1 is S1 of table B and —[C(R$^a$)(R$^b$)]$_m$—[C(R')(R$^d$)]$_n$—CR$^e$=N—OR$^3$ is A1 to A140 of table C.

Table 267 contains compounds of formula 1a with Ar is Ar68 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 268 contains compounds of formula 1a with Ar is Ar68 of table A, R1 is S3 of table B and —[C(R$^a$)(R$^b$)]$_m$,—[C(R$^c$)(R$^d$)]$_n$—CR$^e$=N—OR$^3$ is A1 to A140 of table C.

Table 269 contains compounds of formula 1a with Ar is Ar68 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 270 contains compounds of formula 1a with Ar is Ar69 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 271 contains compounds of formula 1a with Ar is Ar69 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 272 contains compounds of formula 1a with Ar is Ar69 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 273 contains compounds of formula 1a with Ar is Ar69 of table A, R1 is S4 of table B and —[C(R$^e$)(R$^b$)]$_m$—[C(R$^c$)(R$^d$)]$_n$—CR$^e$=N—OR$^3$ is A1 to A140 of table C.

Table 274 contains compounds of formula 1a with Ar is Ar70 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 275 contains compounds of formula 1a with Ar is Ar70 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 276 contains compounds of formula 1a with Ar is Ar70 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 277 contains compounds of formula 1a with Ar is Ar70 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 278 contains compounds of formula 1a with Ar is Ar71 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 279 contains compounds of formula 1a with Ar is Ar71 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 280 contains compounds of formula 1a with Ar is Ar71 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 281 contains compounds of formula 1a with Ar is Ar71 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 282 contains compounds of formula 1a with Ar is Ar72 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 283 contains compounds of formula 1a with Ar is Ar72 of table A, R1 is S2 of table B and —[C(R$^a$)(R$^b$)]$_m$[—C(R$^c$)(R$^d$)]$_n$—CR$^e$=N—OR$^3$ is A1 to A140 of table C.

Table 284 contains compounds of formula 1a with Ar is Ar72 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 285 contains compounds of formula 1a with Ar is Ar72 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 286 contains compounds of formula 1a with Ar is Ar73 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 287 contains compounds of formula 1a with Ar is Ar73 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 288 contains compounds of formula 1a with Ar is Ar73 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 289 contains compounds of formula 1a with Ar is Ar73 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 290 contains compounds of formula 1a with Ar is Ar74 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 291 contains compounds of formula 1a with Ar is Ar74 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 292 contains compounds of formula 1a with Ar is Ar74 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 293 contains compounds of formula 1a with Ar is Ar74 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 294 contains compounds of formula 1a with Ar is Ar75 of table A, R1 is S1 of table B and —[C(R$^a$)(R$^b$)]$_m$[—C(R$^c$)(R$^d$)]$_n$—CR$^e$=N—OR$^3$ is A1 to A140 of table C.

Table 295 contains compounds of formula 1a with Ar is Ar75 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 296 contains compounds of formula 1a with Ar is Ar75 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 297 contains compounds of formula 1a with Ar is Ar75 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 298 contains compounds of formula 1a with Ar is Ar76 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 299 contains compounds of formula 1a with Ar is Ar76 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 300 contains compounds of formula 1a with Ar is Ar76 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 301 contains compounds of formula 1a with Ar is Ar76 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 302 contains compounds of formula 1a with Ar is Ar77 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 303 contains compounds of formula 1a with Ar is Ar77 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 304 contains compounds of formula 1a with Ar is Ar77 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 305 contains compounds of formula 1a with Ar is Ar77 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 306 contains compounds of formula 1a with Ar is Ar78 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 307 contains compounds of formula 1a with Ar is Ar78 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 308 contains compounds of formula 1a with Ar is Ar78 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 309 contains compounds of formula 1a with Ar is Ar78 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 310 contains compounds of formula 1a with Ar is Ar79 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 311 contains compounds of formula 1a with Ar is Ar79 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 312 contains compounds of formula 1a with Ar is Ar79 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 313 contains compounds of formula 1a with Ar is Ar79 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 314 contains compounds of formula 1a with Ar is Ar80 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 315 contains compounds of formula 1a with Ar is Ar80 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 316 contains compounds of formula 1a with Ar is Ar80 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 317 contains compounds of formula 1a with Ar is Ar80 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 318 contains compounds of formula 1a with Ar is Ar81 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 319 contains compounds of formula 1a with Ar is Ar81 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 320 contains compounds of formula 1a with Ar is Ar81 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 321 contains compounds of formula 1a with Ar is Ar81 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 322 contains compounds of formula 1a with Ar is Ar82 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 323 contains compounds of formula 1a with Ar is Ar82 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 324 contains compounds of formula 1a with Ar is Ar82 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 325 contains compounds of formula 1a with Ar is Ar82 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

Table 326 contains compounds of formula 1a with Ar is Ar83 of table A, R1 is S1 of table B and —[C(R$^a$)(R$^b$)]$_m$—[C(R$^c$)(R$^d$)]$_n$—CR$^e$=N—OR$^3$ is A1 to A140 of table C.

Table 327 contains compounds of formula 1a with Ar is Ar83 of table A, R1 is S2 of table B and —[C(R$^a$)(R$^b$)]$_m$—[C(R$^c$)(R$^d$)]$_n$—CR$^e$=N—OR$^3$ is A1 to A140 of table C.

Table 328 contains compounds of formula 1a with Ar is Ar83 of table A, R1 is S3 of table B and —[C(R$^a$)(R$^b$)]$_m$—[C(R$^c$)(R$^d$)]$_n$—CR$^e$=N—OR$^3$ is A1 to A140 of table C.

Table 329 contains compounds of formula 1a with Ar is Ar83 of table A, R1 is S4 of table B and —[C(R$^a$)(R$^b$)]$_m$—[C(R$^c$)(R$^d$)]$_n$—CR$^e$=N—OR$^3$ is A1 to A140 of table C.

The compounds of formula (1) may be prepared as outlined in Schemes 1 to 17 below in which Ar, R$^1$, R$^2$, R$^a$, R$^b$, R$^c$, R$^d$, R$^e$, R$^3$, m and n have the meanings given above and L is O unless otherwise indicated in the text. As shown in Scheme 1, the compounds of general formula (1) may be prepared by reacting a compound of the general formula (2) with a compound of the general formula (3) in the presence of a base in a suitable solvent. Typical solvents include N,N-dimethylformamide and N-methylpyrrolidin-2-one. Suitable bases include potassium carbonate, sodium hydride or diisopropylethylamine. Some of the intermediates and starting materials are known compounds and may be commercially available or may be prepared according to procedures known to those skilled in the art. It is noteworthy that the brief description on each of the arrows for each conversion is for illustration purposes only and should not be regarded as limiting with respect to the sequence or each individual step.

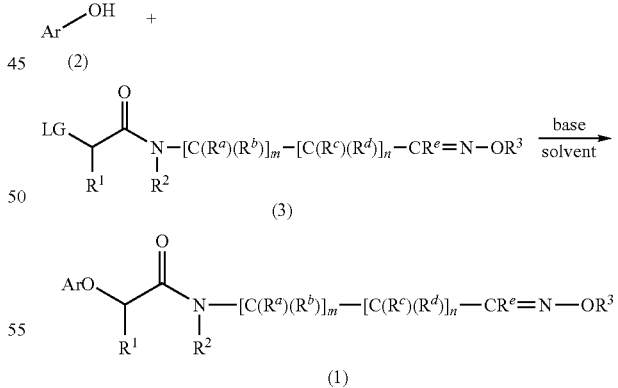

As shown in Scheme 2, compounds of the general formula (3) may be prepared by reacting an amine of the general formula (5) with an activated carboxylic acid such as an acid halide or the corresponding acid anhydride of the general formula (4), in the presence of a suitable inorganic or organic base, such as potassium carbonate or diisopropylethylamine, in a solvent such as dichloromethane, tetrahydrofuran or, N,N-dimethylformamide.

Scheme 2

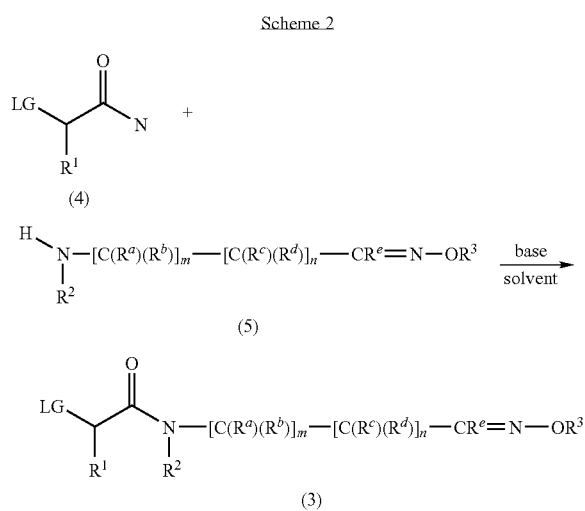

LG = leaving group

Alternatively, as shown in Scheme 3, compounds of the general formula (1) may be prepared by condensing a compound of the general formula (7a), wherein R is H with an amine of the general formula (5) using suitable activating reagents such as 1-hydroxy-benzotriazole (HOBt), (benzotriazol-1-yloxy)-tris-(dimethylamino)-phosphonium-hexafluorophosphate (BOP), 1-hydroxy-7-azabenzotriazole (HOAT) or, N-(3-dimethylamino-propyl)-N'-ethyl-carbodiimide hydrochloride (EDC).

Scheme 3

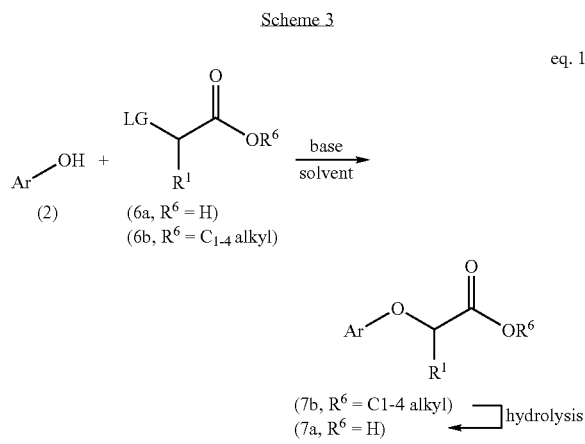

Alternatively, compounds of the general formula (1) may be prepared via the intermediacy of compounds of general formula (7b), wherein $R^6$ is $C_{1-4}$ alkyl as shown in Scheme 3. The esters of the general formula (7b), wherein $R^6$ is $C_{1-4}$ alkyl and also acids of the general formula (7a), wherein $R^6$ is H, may be prepared by reacting a compound of the general formula (2) with an ester or acid of the general formula (6a and 6b respectively) in the presence of a suitable base, such as potassium carbonate or sodium hydride, in a suitable solvent, such as N,N-dimethylformamide. The esters or acids of the general formula (6a or 6b) are either commercially available or may be prepared by standard literature methods from commercially available materials.

Alternatively, as shown in Scheme 4, compounds of the general formula (7b) may be prepared under Mitsunobu conditions by reacting a compound of the general formula (2) with a compound of the general formula (6b), wherein $R_d$ is $C_{1-4}$ alkyl, using a phosphine, such as triphenyl phosphine, and an azoester, such as diethyl azodicarboxylate.

Scheme 4

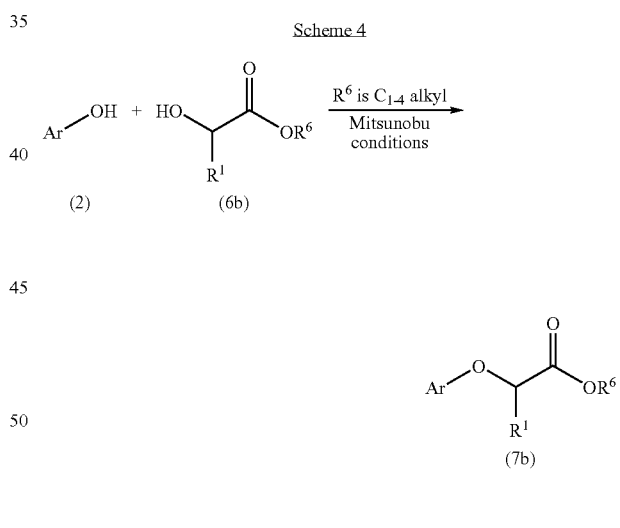

In another approach towards the preparation of compounds of the general formula (1) shown in Scheme 5, compound of general formula (6d) may be reacted with a compound of the general formula (2) under Mitsunobu conditions using a phosphine, such as triphenyl phosphine, and an azoester, such as diethyl azodicarboxylate. Compounds of general formula (6d) may be prepared from a compound of general formula (6c) and an amine of general formula (5) using suitable activating reagents such as 1-hydroxybenzotriazole and N-(3-dimethylaminopropyl)-M-ethyl-carbodiimide hydrochloride.

Scheme 5

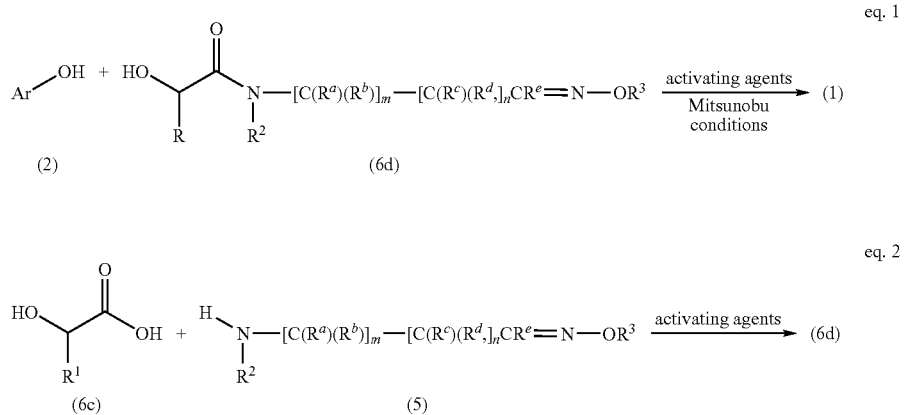

Compounds (6b) and (6c) are either known compounds or may be made from commercially available and/or known compounds by those skilled in the art. In addition, compounds of the general formula (1) wherein R1 is defined as in claim 1, may be prepared as shown in Scheme 6. Thus, esters of the formula (8) may be halogenated to give haloesters of the general formula (9), by treatment with a suitable halogenating agent, such as N-bromosuccinimide, in a suitable solvent such as carbon tetrachloride, at between ambient temperature and the reflux temperature of the solvent. The haloesters of the general formula (9) can be reacted with an alkali metal compound $M^+OR_1$ or $M^+SR_1$, where M is suitably sodium or potassium in, for example, an alcohol $R_1OH$ or thiol $R_1SH$ as solvent, at between 0° C. and 60° C., preferably at ambient temperature, to give compounds of the general formula (7b). The esters (7b) can be hydrolysed to acids of the general formula (7a), by treatment with an alkali metal hydroxide, such as sodium hydroxide, in an aqueous alcohol $R_1OH$, between ambient temperature and reflux. A carboxylic acid of the general formula (7a) can be condensed with an amine of the general formula (5) to give a compound of the general formula (1), where $R_1$ is as defined above, using suitable activating reagents such as 1-hydroxybenzotriazole and N-(3-dimethylaminopropyl)-N'-ethylcarbodiimide hydro-chloride.

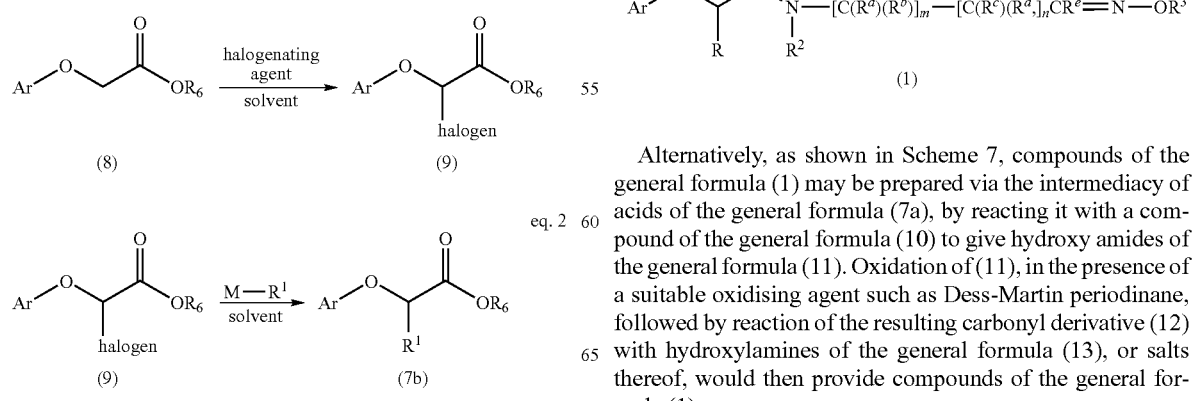

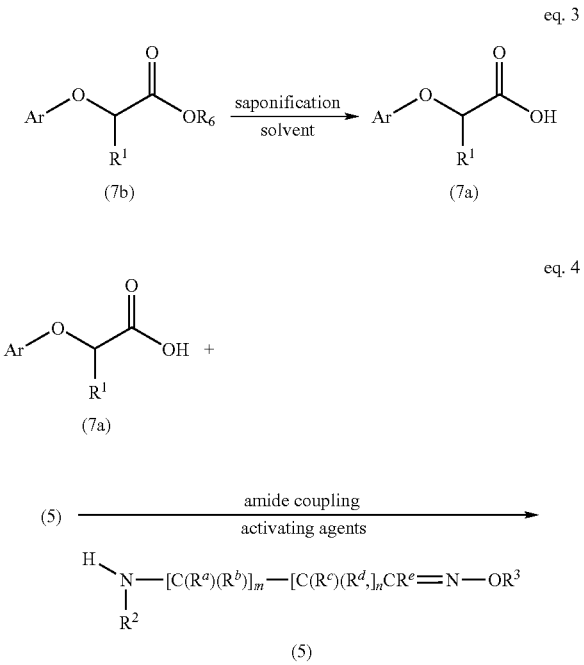

Alternatively, as shown in Scheme 7, compounds of the general formula (1) may be prepared via the intermediacy of acids of the general formula (7a), by reacting it with a compound of the general formula (10) to give hydroxy amides of the general formula (11). Oxidation of (11), in the presence of a suitable oxidising agent such as Dess-Martin periodinane, followed by reaction of the resulting carbonyl derivative (12) with hydroxylamines of the general formula (13), or salts thereof, would then provide compounds of the general formula (1).

35

Scheme 7

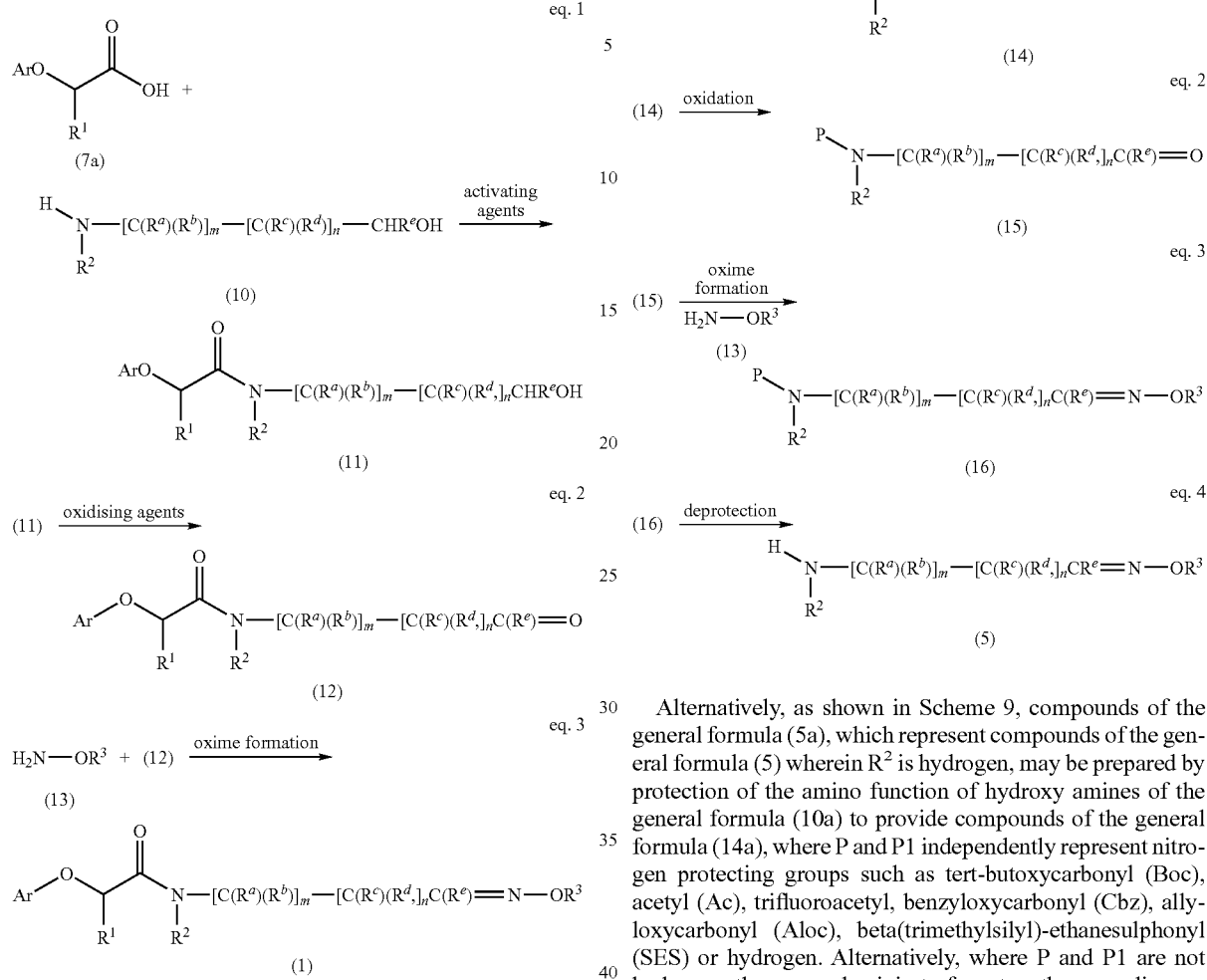

As shown in Scheme 8, amines of the general formula (5) may be prepared by protection of the amino function of hydroxy amines of the general formula (10) to provide compounds of the general formula (14) where P represents a nitrogen protecting group such as tert-butoxycarbonyl (Boc), acetyl (Ac), trifluoroacetyl, benzyloxycarbonyl (Cbz), followed by reaction with a suitable oxidising agent, for example, sulphur trioxide-pyridine complex in dimethyl sulphoxide, to form an oxidised compound of the general formula (15). This carbonyl derivative of general formula (15) can be reacted with hydroxylamines of the general formula (13), to provide the amino-protected hydroxyl amines of the general formula (16). Deprotection of the amino group of (16) provides amines of the general formula (5) which is meant to also include salts thereof.

Scheme 8

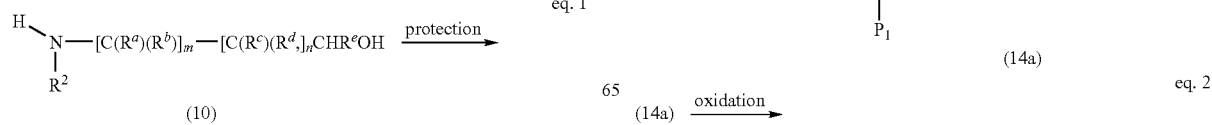

36

Alternatively, as shown in Scheme 9, compounds of the general formula (5a), which represent compounds of the general formula (5) wherein $R^2$ is hydrogen, may be prepared by protection of the amino function of hydroxy amines of the general formula (10a) to provide compounds of the general formula (14a), where P and P1 independently represent nitrogen protecting groups such as tert-butoxycarbonyl (Boc), acetyl (Ac), trifluoroacetyl, benzyloxycarbonyl (Cbz), allyloxycarbonyl (Aloc), beta(trimethylsilyl)-ethanesulphonyl (SES) or hydrogen. Alternatively, where P and P1 are not hydrogen, they may also join to form together a cyclic protecting group such as phthalimide (Pht). Reaction of (14a) with a suitable oxidising agent, for example, sulphur trioxide-pyridine complex in dimethyl sulphoxide, forms an oxidised compound of the general formula (15a). This carbonyl derivative of general formula (15a), can be reacted with hydroxylamines of the general formula (13), to provide the amino-protected oximes of the general formula (16a). Deprotection of the amino group of (16) provides amino-oximes of the general formula (5a) which is meant to also include salts thereof.

Scheme 9

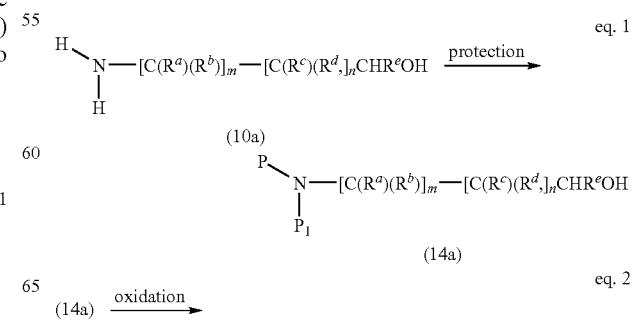

37

-continued

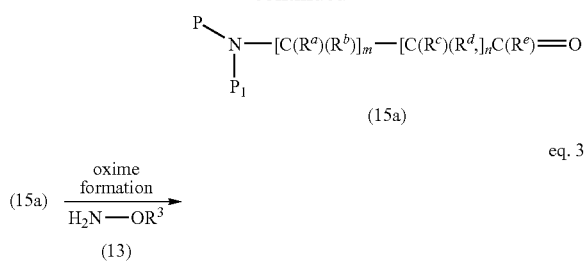

(15a)

(15a) →[oxime formation, $H_2N-OR^3$ (13)] eq. 3

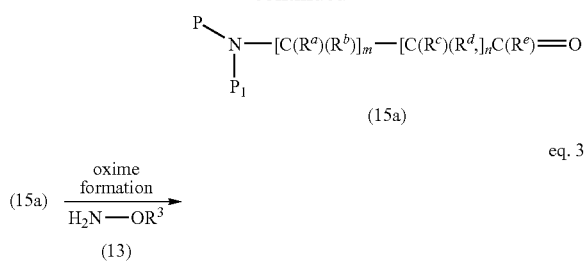

(16a)

(16a) →[deprotection] eq. 4

H-N(H)-[C(R^a)(R^b)]_m-[C(R^c)(R^d)]_nCR^e=N-OR^3

(5a)

As illustrated is Scheme 10, alkyloxy-, alkenyloxy- and alkynyloxy-alkylamines of the general formula (20), wherein $R^6$ is $C_{1-4}$ alkyl, $C_{3-5}$ alkenyl, $C_{3-5}$ alkynyl, useful for the preparation of oximino compounds of the general formula (1)—as shown in Scheme 11—may be prepared via a protection, alkylation and deprotection sequence.

Scheme 10

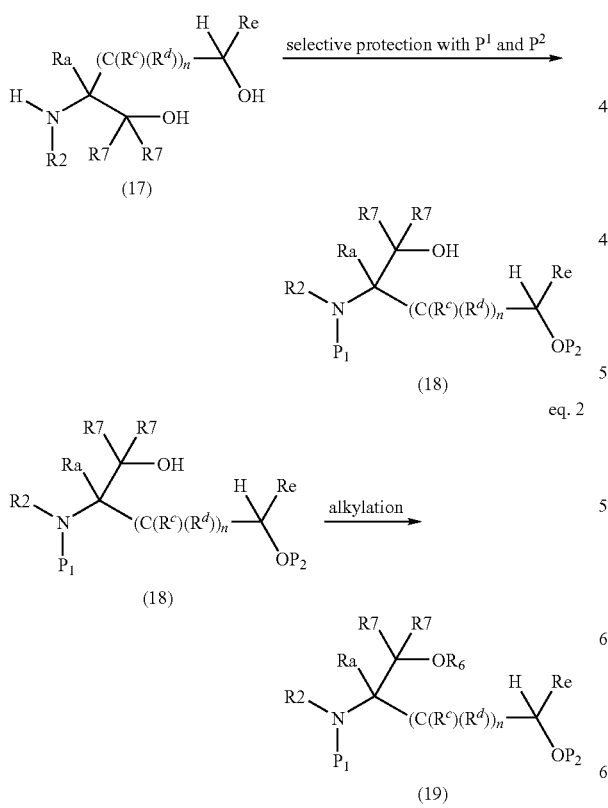

38

-continued eq. 3

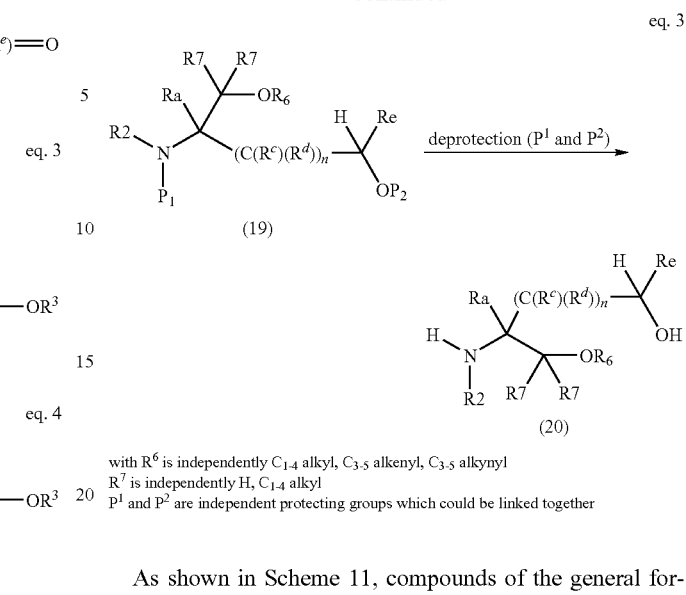

(19) →[deprotection ($P^1$ and $P^2$)]

(20)

with $R^6$ is independently $C_{1-4}$ alkyl, $C_{3-5}$ alkenyl, $C_{3-5}$ alkynyl
$R^7$ is independently H, $C_{1-4}$ alkyl
$P^1$ and $P^2$ are independent protecting groups which could be linked together As shown in Scheme 11, compounds of the general formula (1a) may be prepared via reaction of acids of the general formula (7a), by reacting it with a compound of the general formula (20) (Scheme 11, equation 1) to give hydroxy amides of the general formula (21). Oxidation of (21), followed by reaction of the carbonyl derivative (22) with compounds of the general formula (13), or salts thereof, then provides compounds of the formula (1a), which are examples of compounds of the general formula (1), wherein L is oxygen and $R^b$ is hydroxyl-$(C_{1-4})$-alkyl, $C_{1-4}$ alkoxy-$(C_{1-4})$-alkyl, $C_{3-5}$ alkenyloxy-$(C_{1-4}$-alkyl or $C_{3-5}$ alkynyloxy-$(C_{1-4}$-alkyl.

Scheme 11

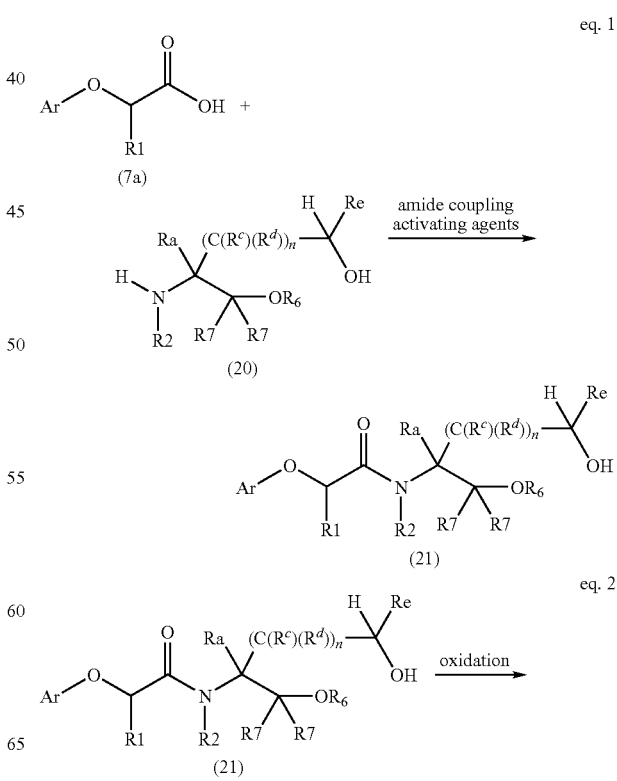

-continued

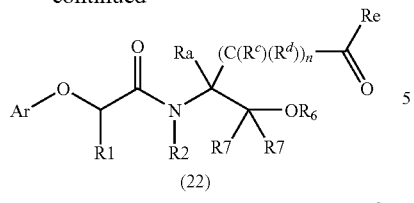

eq. 3

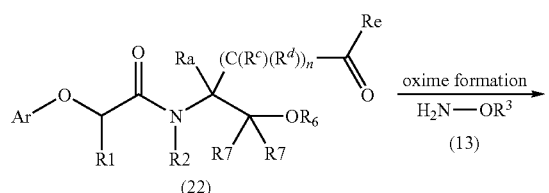

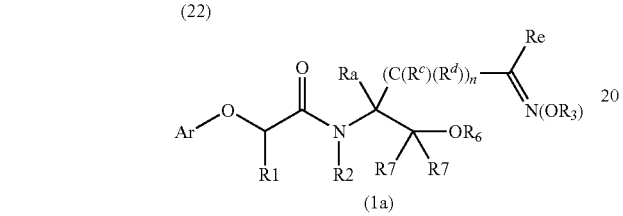

with R⁶ is independently H, C₁₋₄ alkyl, C₂₋₄ alkenyl, C₂₋₄ alkynyl
R⁷ is independently H, C₁₋₄ alkyl Alternatively, as illustrated in Scheme 12, equation 5, compounds (1b), of the general formula (1), wherein L is oxygen and $R^b$ is $C_{1-4}$ alkoxy-($C_{1-4}$)-alkyl, $C_{3-5}$ alkenyloxy-($C_{1-4}$)-alkyl or $C_{3-5}$ alkynyloxy-($C_{1-4}$), can be prepared directly by coupling a carboxylic acid of the general formula (7a) with an amine of the general formula (26). Amines (26), which are examples of amines of the general formula (5), wherein $R^b$ is $C_{1-4}$-alkoxy-($C_{1-4}$-alkyl, $C_{3-5}$ alkenyloxy-($C_{1-4}$)-alkyl or $C_{3-5}$ alkynyloxy-($C_{10}$), can be prepared as summarized in Scheme 12, equations 1-5.

Scheme 12 eq. 1

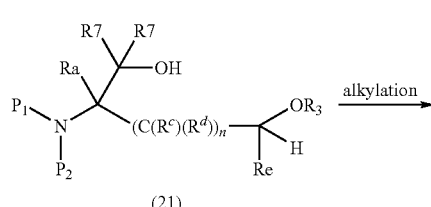

eq. 2

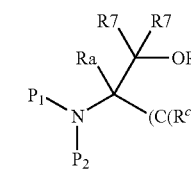

-continued

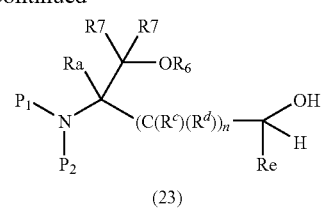

eq. 3

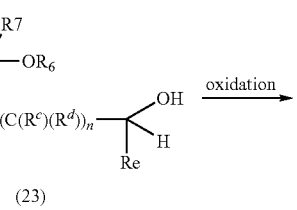

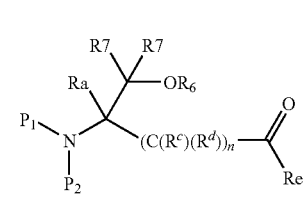

eq. 4

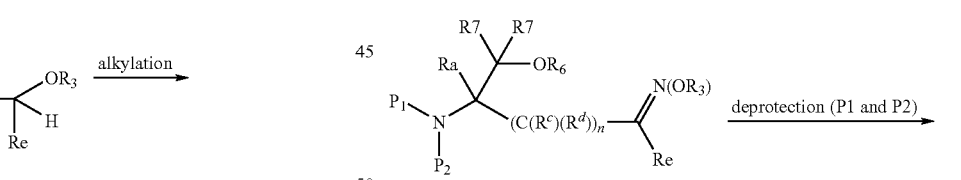

eq. 5

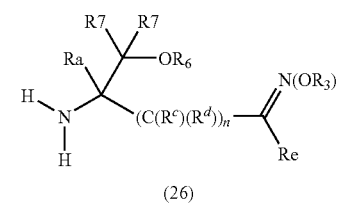

eq. 6

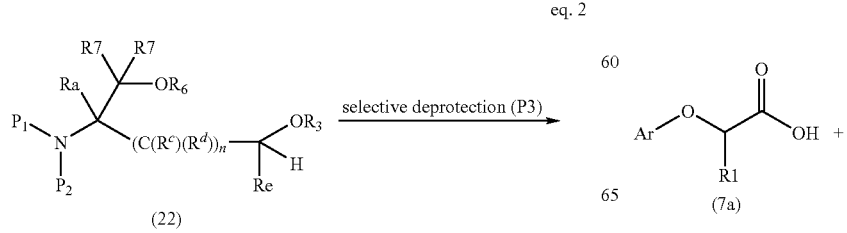

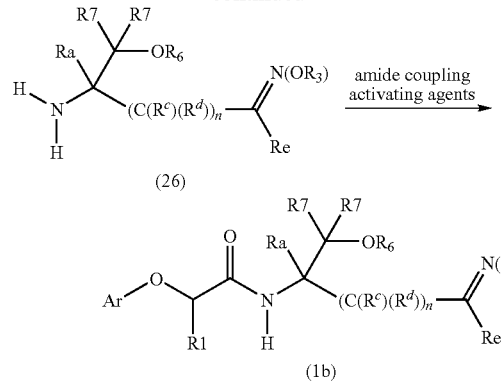

with P₁, P₃ are independent protecting groups
P₂ is R² or protecting group
R⁶ is independently $C_{1-4}$ alkyl, $C_{2-4}$ alkenyl, $C_{2-4}$ alkynyl
R⁷ is independently H, $C_{1-4}$ alkyl Compounds of the general formula (1c), which are examples of compounds of the general formula (1), wherein $R^b$ is ethynyl, may be prepared from acids of the general formula (7a) in six synthetic steps, well known to those skilled in the art, as illustrated in Scheme 13.

Scheme 13

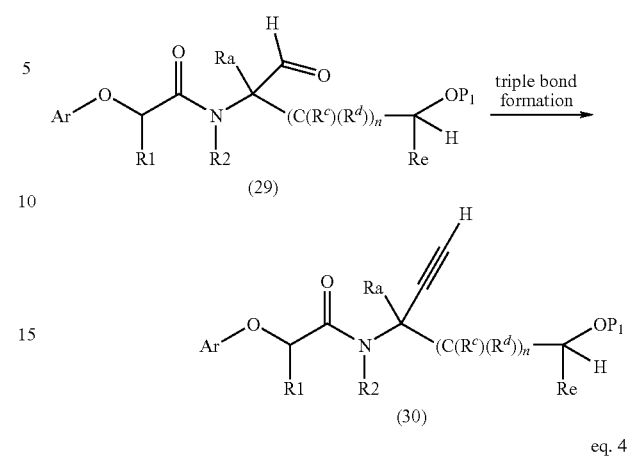

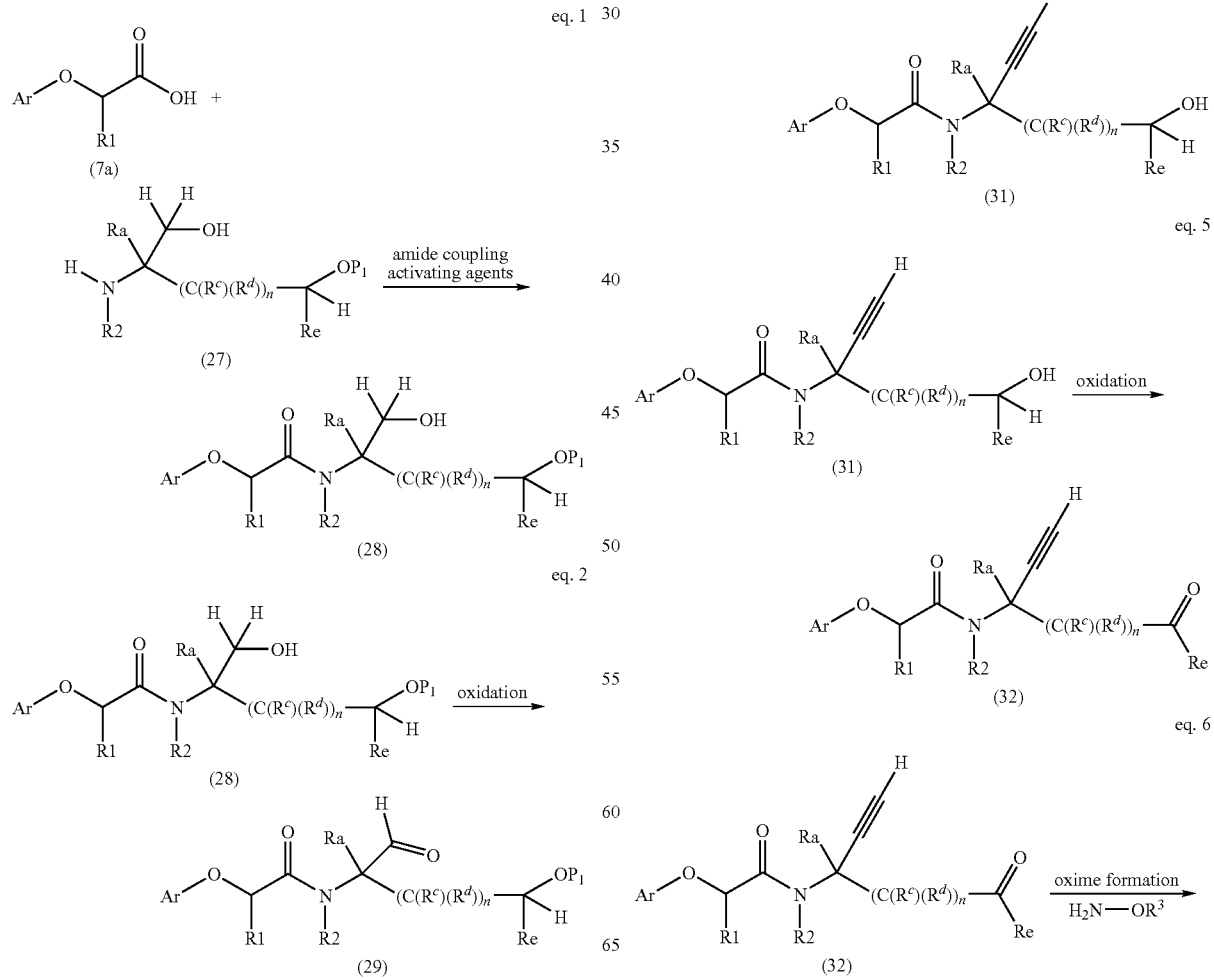

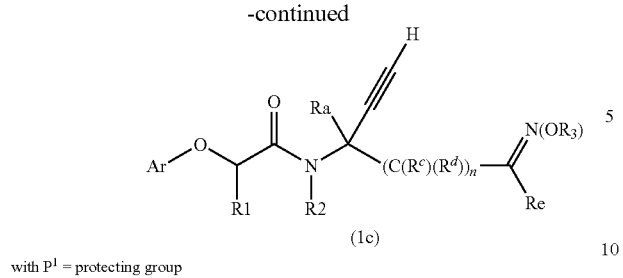

(1c)

with P¹ = protecting group

Alternatively, as illustrated in Scheme 14, equation 7, compounds of the general formula (1c) can be prepared directly by coupling a carboxylic acid of the general formula (7a) with an amine of the general formula (38). Amines (38), which are examples of amines of the general formula (5), wherein $R^b$ is ethynyl, can be prepared by those skilled in the art, as summarized in Scheme 14, equations 1-6.

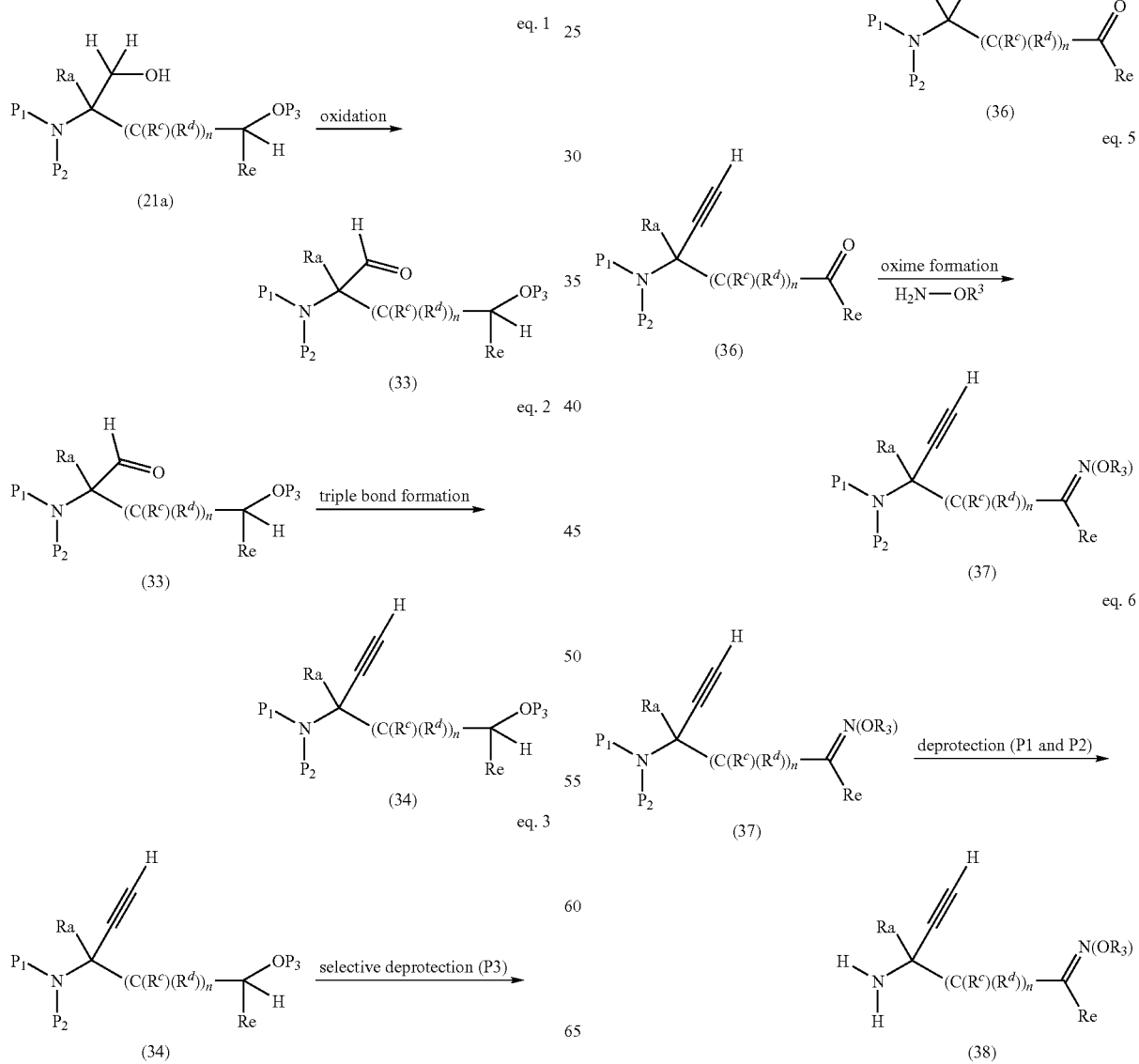

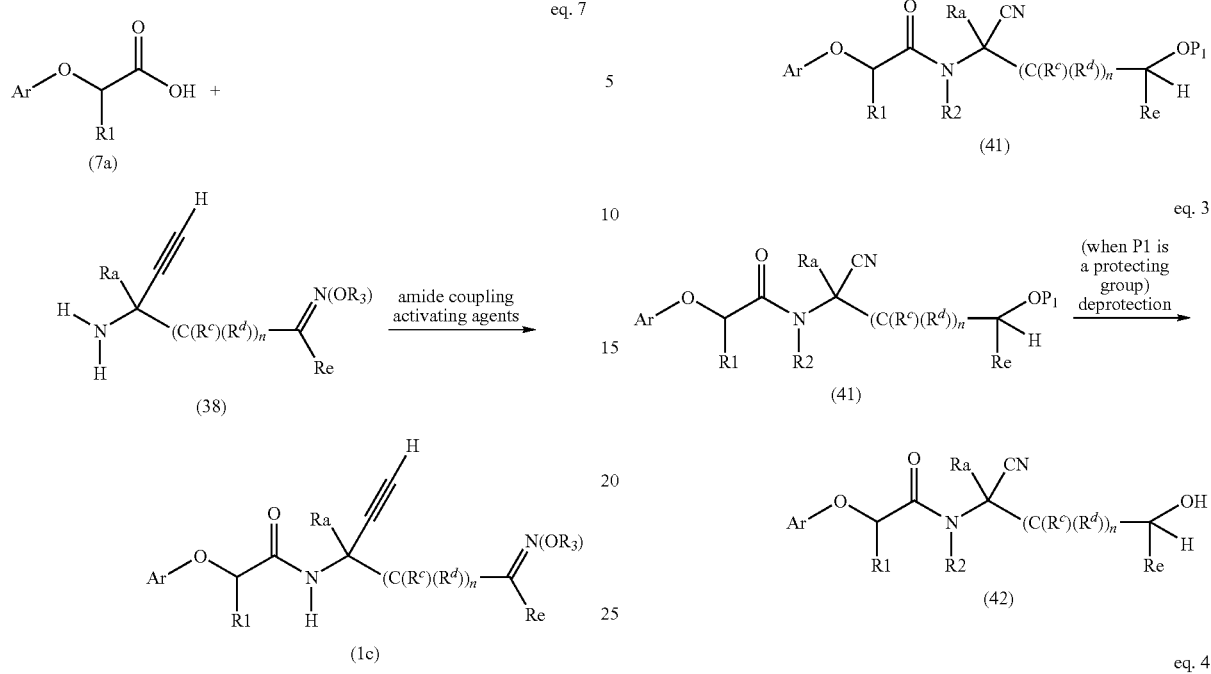

with P₁, P₃ are independent protecting groups
P₂ is R² or protecting group

As shown in Scheme 15, compounds of the general formula (1d), which are examples of compounds of the general formula (1), wherein $R^b$ is cyano, may be prepared from acids of the general formula (7a) in four synthetic steps well known to those skilled in the art.

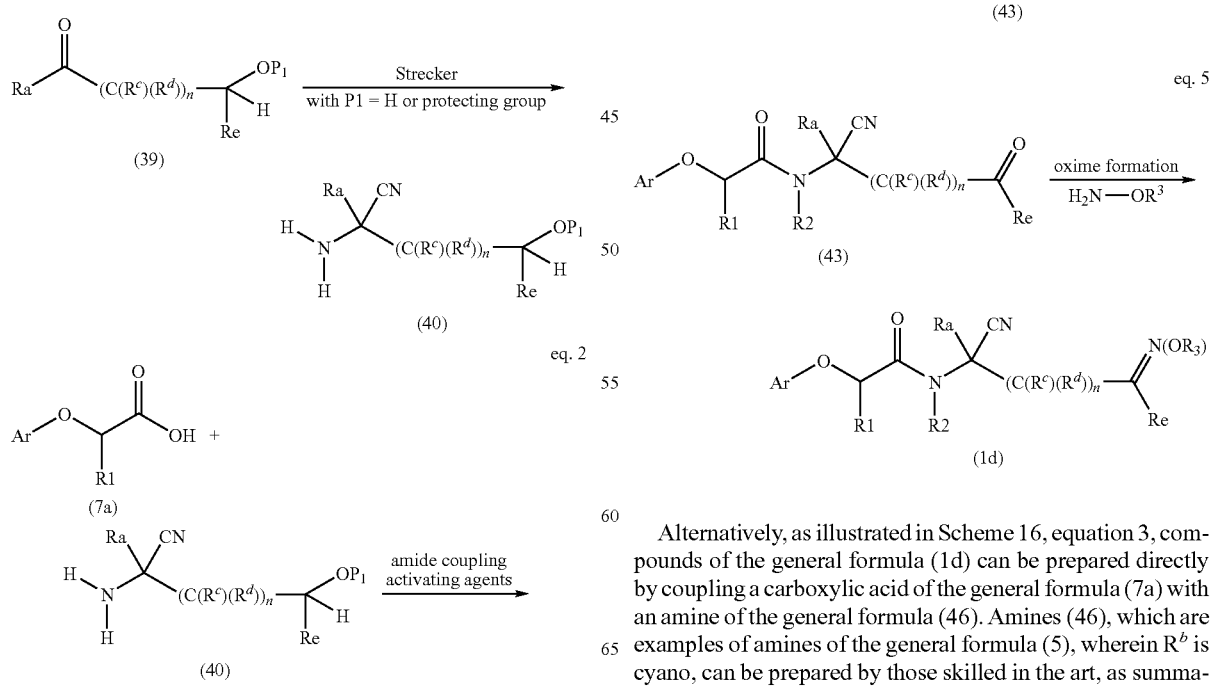

Alternatively, as illustrated in Scheme 16, equation 3, compounds of the general formula (1d) can be prepared directly by coupling a carboxylic acid of the general formula (7a) with an amine of the general formula (46). Amines (46), which are examples of amines of the general formula (5), wherein $R^b$ is cyano, can be prepared by those skilled in the art, as summarized in Scheme 16, equations 1-2.

Scheme 16
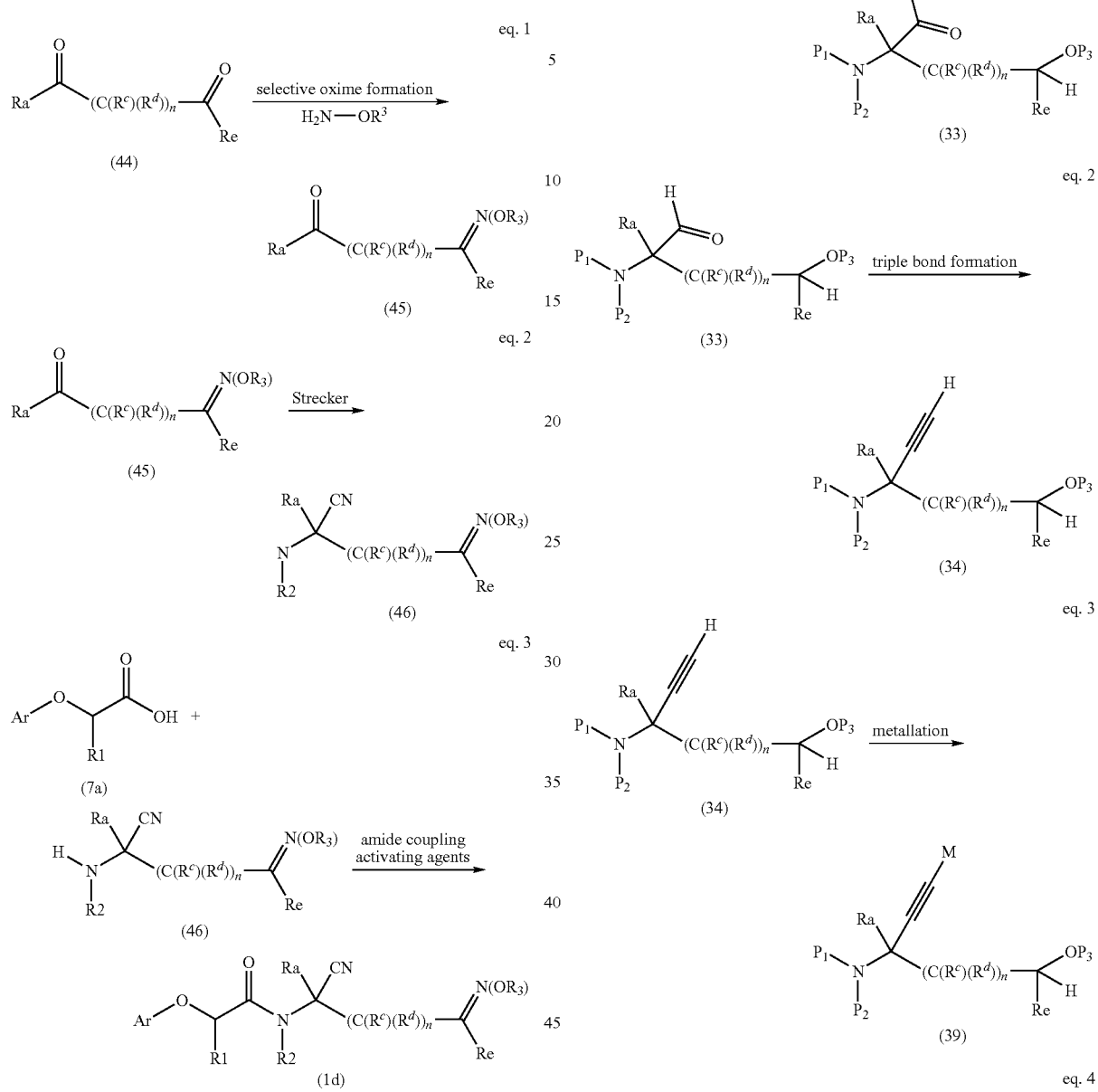
Compounds of the general formula (1e), wherein $R^b$ is $C_{1-3}$ alkoxy($C_{1-3}$)alkyl($C_{1-3}$)-alkynyl, $C_{1-3}$ alkenyloxy($C_{1-3}$)alkyl ($C_{1-3}$)-alkynyl, $C_{1-3}$ alkynyloxy($C_{1-3}$)alkyl($C_{1-3}$)-alkynyl, can be prepared by those skilled in the art, as summarized in Scheme x, equations 1-9.
Scheme 17

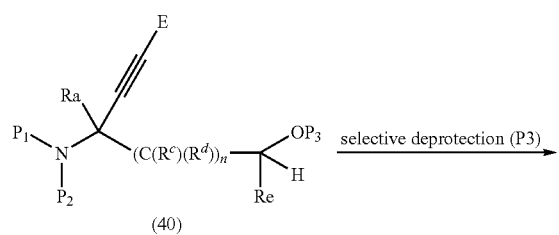

eq. 5

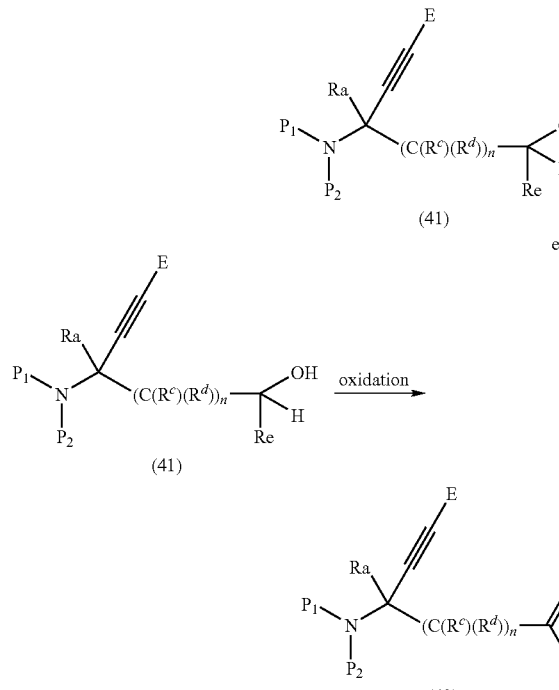

eq. 6 eq. 7

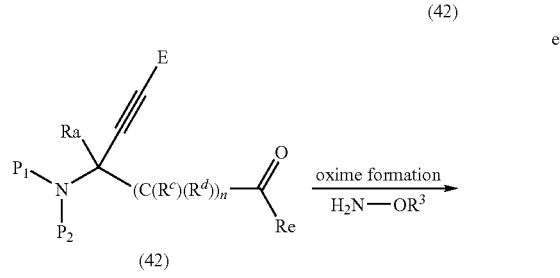

eq. 8

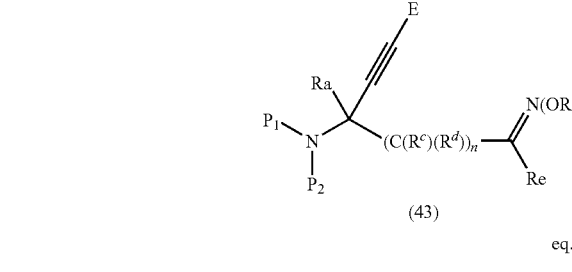

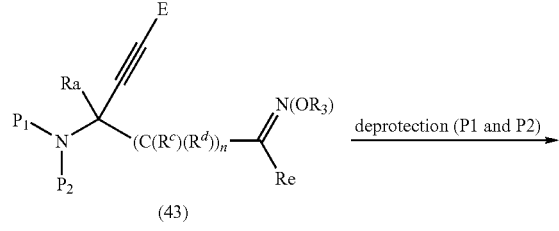

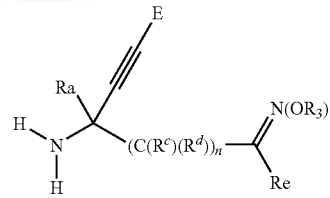

eq. 9 with $P_1$, $P_3$ are independent protecting groups; $P_2 = R2$ or protecting group; $E = C_{1-4}$ alkyl, $C_{1-4}$ alkoxy alkyl, $C_{1-4}$ hydroxy alkyl Other compounds of the invention may be prepared by transforming the substituents in the compounds of the general formula (1) using procedures known to those skilled in the art. Thus, compounds of the formula (1) may further be prepared by converting certain compounds of the formula (1) into each other according to known functional group transformations. For example, compounds of the general (1) wherein $R^3$ is hydrogen may be alkylated to give oximes of the general formula (1) wherein $R^3$ is $C_1$ alkyl by treatment with a suitable alkylating agent, such iodoethane, in a suitable solvent such as acetonitrile, at between ambient temperature and the reflux temperature of the solvent. Further, compounds of the general formula (1) wherein the aryl moiety (Ar) is substituted by halogen, such as bromine or iodine, may be transformed into further compounds of the general formula (1) wherein the halo substituent of the aryl moiety (Ar) is replaced by $C_{2-4}$-alkenyl (eg vinyl) or $C_{2-4}$alkynyl (eg ethynyl, propyn-1-yl) using transition metal (eg palladium (0)) catalyzed vinylation and alkynylation reactions (eg Heck, Stille, Sonogashira) well known to those skilled in the art. Furthermore, such compounds of the general formula (1) wherein the halo substituent of the aryl moiety (Ar) is replaced by $C_{2-4}$alkenyl (eg vinyl) or $C_{2-4}$alkynyl (eg ethynyl, propyn-1-yl) may be prepared indirectly from compounds of the general formula (7b, Scheme 3) using the forementioned transition metal-mediated alkenylation or alkynylation reactions followed by routine functional group manipulations known to those skilled in the art.

Hydroxy (hetero)aryls ArOH of the general formula (2) are either commercially available or may be prepared by standard literature methods known to those skilled in the art. (see, for example, *Ann. Chem., Justus Liebigs* (1966), 98-106 for the synthesis of 3-bromo-6-hydroxyquinoline used for the preparation of compounds that are listed in-part in Tables 25 to 28; Synthetic Communications (1991), 21(7), 959-64 for the synthesis of benzo[b]thiophen-5-ol used for the preparation of compounds in that are listed in-part in Tables 218 to 221: Synthetic Communications (2006), 36(14), 1983-1990 for the synthesis of benzofuran-5-ol used for the preparation of compounds in Table 154 to 157 and *European Journal of Organic Chemistry* (2000), (3), 491-497 for the synthesis of 7-bromo-naphthalen-2-ol and see Examples 12, 13, 14, 15, 16, 17 and 18 below for the preparation of additional representative hydroxy (hetero)aryls (ArOH).

Esters or acids of the general formula (6) are either commercially available or may be prepared by standard literature methods from commercially available materials. Oximes of the general formula (13) are either known compounds and may be commercially available or may be prepared according to procedures known to those skilled in the art.

The compounds of formula (I) are active fungicides and may be used to control one or more of the following pathogens: *Pyricularia oryzae* (*Magnaporthe grisea*) on rice and wheat and other *Pyricularia* spp. on other hosts; *Puccinia triticina* (or *recondita*), *Puccinia striiformis* and other rusts on wheat, *Puccinia hordei, Puccinia striiformis* and other rusts on barley, and rusts on other hosts (for example turf, rye, coffee, pears, apples, peanuts, sugar beet, vegetables and ornamental plants); *Phakopsora pachyrhizi* on soybean, *Erysiphe cichoracearum* on cucurbits (for example melon); *Blumeria* (or *Etysiphe*) *graminis* (powdery mildew) on barley, wheat, rye and turf and other powdery mildews on various hosts, such as *Sphaerotheca macularis* on hops, *Sphaerotheca fusca* (*Sphaerotheca fuliginea*) on cucurbits (for example cucumber), *Leveillula taurica* on tomatoes, aubergine and green pepper, *Podosphaera leucotricha* on apples and *Uncinula necator* on vines; *Cochliobolus* spp., *Helminthosporium* spp., *Drechslera* spp. (*Pyrenophora* spp.), *Rhynchosporium* spp., *Mycosphaerella graminicola* (*Septoria tritici*) and *Phaeosphaeria nodorum* (*Stagonospora nodorum* or *Septoria nodorum*), *Pseudocercosporella herpotrichoides* and *Gaeumannomyces graminis* on cereals (for example wheat, barley, rye), turf and other hosts; *Cercospora arachidicola* and *Cercosporidium personatum* on peanuts and other *Cercospora* spp. on other hosts, for example sugar beet, bananas, soya beans and rice; *Botrytis cinerea* (grey mould) on tomatoes, strawberries, vegetables, vines and other hosts and other *Botrytis* spp. on other hosts; *Alternaria* spp. on vegetables (for example carrots), oil-seed rape, apples, tomatoes, potatoes, cereals (for example wheat) and other hosts; *Venturia* spp. (including *Venturia inaequalis* (scab)) on apples, pears, stone fruit, tree nuts and other hosts; *Cladosporium* spp. on a range of hosts including cereals (for example wheat) and tomatoes; *Monilinia* spp. on stone fruit, tree nuts and other hosts; *Didymella* spp. on tomatoes, turf, wheat, cucurbits and other hosts; *Phoma* spp. on oil-seed rape, turf, rice, potatoes, wheat and other hosts; *Aspergillus* spp. and *Aureobasidium* spp. on wheat, lumber and other hosts; *Ascochyta* spp. on peas, wheat, barley and other hosts; *Stemphylium* spp. (*Pleospora* spp.) on apples, pears, onions and other hosts; summer diseases (for example bitter rot (*Glomerefia cingulata*), black rot or frogeye leaf spot (*Bottyosphaeria obtusa*), Brooks fruit spot (*Mycosphaerella pomi*), Cedar apple rust (*Gymnosporangium juniperi-virginianae*), sooty blotch (*Gloeodes pomigena*), flyspeck (*Schizothyrium pomi*) and white rot (*Botryosphaeria dothidea*)) on apples and pears; *Plasmopara viticola* on vines; *Plasmopara halstedii* on sunflower; other downy mildews, such as *Bremia lactucae* on lettuce, *Peronospora* spp. on soybeans, tobacco, onions and other hosts, *Pseudoperonospora humuli* on hops; *Peronosclerospora maydis, P. philippinensis* and *P. sorghi* on maize, sorghum and other hosts and *Pseudoperonospora cubensis* on cucurbits; *Pythium* spp. (including *Pythium ultimum*) on cotton, maize, soybean, sugarbeet, vegetables, turf and other hosts; *Phytophthora infestans* on potatoes and tomatoes and other *Phytophthora* spp. on vegetables, strawberries, avocado, pepper, ornamentals, tobacco, cocoa and other hosts; *Aphanomyces* spp. on sugarbeet and other hosts; *Thanatephorus cucumeris* on rice, wheat, cotton, soybean, maize, sugarbeet and turf and other hosts *Rhizoctonia* spp. on various hosts such as wheat and barley, peanuts, vegetables, cotton and turf; *Sclerotinia* spp. on turf, peanuts, potatoes, oil-seed rape and other hosts; *Sclerotium* spp. on turf, peanuts and other hosts; *Gibberella fujikuroi* on rice; *Colletotrichum* spp. on a range of hosts including turf, coffee and vegetables; *Laetisaria fuciformis* on turf; *Mycosphaerella* spp. on bananas, peanuts, citrus, pecans, papaya and other hosts; *Diaporthe* spp. on citrus, soybean, melon, pears, lupin and other hosts; *Elsinoe* spp. on citrus, vines, olives, pecans, roses and other hosts; *Verticillium* spp. on a range of hosts including hops, potatoes and tomatoes; *Pyrenopeziza* spp. on oil-seed rape and other hosts; *Oncobasidium theobromae* on cocoa causing vascular streak dieback; *Fusarium* spp. incl. *Fusarium culmorum, F. graminearum, F. langsethiae, F. moniliforme, F. proliferatum, F. subglutinans, F. solani* and *F. oxysporum* on wheat, barely, rye, oats, maize, cotton, soybean, sugarbeet and other hosts, *Typhula* spp., *Microdochium nivale, Ustilago* spp., *Urocystis* spp., *Tilletia* spp. and *Claviceps purpurea* on a variety of hosts but particularly wheat, barley, turf and maize; *Ramularia* spp. on sugar beet, barley and other hosts; *Thielaviopsis basicola* on cotton, vegetables and other hosts; *Verticillium* spp. on cotton, vegetables and other hosts; post-harvest diseases particularly of fruit (for example *Penicillium digitatum, Penicillium italicum* and *Trichoderma viride* on oranges, *Colletotrichum musae* and *Gloeosporium musarum* on bananas and *Botrytis cinerea* on grapes); other pathogens on vines, notably *Eutypa lata, Guignardia bidwellii, Phellinus igniarus, Phomopsis viticola, Pseudopeziza tracheiphila* and *Stereum hirsutum*; other pathogens on trees (for example *Lophodermium seditiosum*) or lumber, notably *Cephaloascus fragrans, Ceratocystis* spp., *Ophiostoma piceae, Penicillium* spp., *Trichoderma pseudokoningii, Trichoderma viride, Trichoderma harzianum, Aspergillus niger, Leptographium lindbergi* and *Aureobasidium pullulans*; and fungal vectors of viral diseases (for example *Polymyxa graminis* on cereals as the vector of barley yellow mosaic virus (BYMV) and *Polymyxa betae* on sugar beet as the vector of rhizomania).

Preferably, the following pathogens are controlled: *Pyricularia oryzae* (*Magnaporthe grisea*) on rice and wheat and other *Pyricularia* spp. on other hosts; *Erysiphe cichoracearum* on cucurbits (for example melon); *Blumeria* (or *Erysiphe*) *graminis* (powdery mildew) on barley, wheat, rye and turf and other powdery mildews on various hosts, such as *Sphaerotheca macularis* on hops, *Sphaerotheca fusca* (*Sphaerotheca fuliginea*) on cucurbits (for example cucumber), *Leveillula taurica* on tomatoes, aubergine and green pepper, *Podosphaera leucotricha* on apples and *Uncinula necator* on vines; *Helminthosporium* spp., *Drechslera* spp. (*Pyrenophora* spp.), *Rhynchosporium* spp. *Mycosphaerella graminicola* (*Septoria tritici*) and *Phaeosphaeria nodorum* (*Stagonospora nodorum* or *Septoria nodorum*), *Pseudocercosporella herpotrichoides* and *Gaeumannomyces graminis* on cereals (for example wheat, barley, rye), turf and other hosts; *Cercospora arachidicola* and *Cercosporidium personatum* on peanuts and other *Cercospora* spp. on other hosts, for example sugar beet, bananas, soya beans and rice; *Botrytis cinerea* (grey mould) on tomatoes, strawberries, vegetables, vines and other hosts and other *Botrytis* spp. on other hosts; *Alternaria* spp. on vegetables (for example carrots), oil-seed rape, apples, tomatoes, potatoes, cereals (for example wheat) and other hosts; *Venturia* spp. (including *Venturia inaequalis* (scab)) on apples, pears, stone fruit, tree nuts and other hosts; *Cladosporium* spp. on a range of hosts including cereals (for example wheat) and tomatoes; *Monilinia* spp. on stone fruit, tree nuts and other hosts; *Didymella* spp. on tomatoes, turf, wheat, cucurbits and other hosts; *Phoma* spp. on oil-seed rape, turf, rice, potatoes, wheat and other hosts; *Aspergillus* spp. and *Aureobasidium* spp. on wheat, lumber and other hosts; *Ascochyta* spp. on peas, wheat, barley and other hosts; *Stemphylium* spp. (*Pleospora* spp.) on apples, pears, onions and other hosts; summer diseases (for example bitter rot (*Glomerella cingulata*), black rot or frogeye leaf spot (*Botryosphaeria obtusa*), Brooks fruit spot (*Mycosphaerella pomi*), Cedar apple rust (*Gymnosporangium juniperi-virginianae*), sooty blotch (*Gloeodes pomigena*), flyspeck (*Schizothyrium pomi*) and white rot (*Botryosphaeria dothidea*)) on apples and pears; *Plasmopara viticola* on vines; *Plasmopara halstedii* on sunflower; other downy mildews, such as *Bremia lactucae* on lettuce, *Peronospora* spp. on soybeans, tobacco, onions and other hosts, *Pseudoperonospora humuli* on hops; *Peronosclerospora maydis, P. philippinensis* and *P. sorghi* on maize, sorghum and other hosts and *Pseudoperonospora cubensis* on cucurbits; *Pythium* spp. (including *Pythium ultimum*) on cotton, maize, soybean, sugarbeet, vegetables, turf and other hosts; *Phytophthora infestans* on potatoes and tomatoes and other *Phytophthora* spp. on vegetables, strawberries, avocado, pepper, ornamentals, tobacco, cocoa and other hosts; *Aphanomyces* spp. on sugarbeet and other hosts; *Thanatephorus cucumeris* on rice, wheat, cotton, soybean, maize, sugarbeet and turf and other hosts *Rhizoctonia* spp. on various hosts such as wheat and barley, peanuts, vegetables, cotton and turf; *Sclerotinia* spp. on turf, peanuts, potatoes, oil-seed rape and other hosts; *Sclerotium* spp. on turf, peanuts and other hosts; *Gibberella fujikuroi* on rice; *Colletotrichum* spp. on a range of hosts including turf, coffee and vegetables; *Laetisaria fuciformis* on turf; *Mycosphaerella* spp. on bananas, peanuts, citrus, pecans, papaya and other hosts; *Fusarium* spp. incl. *Fusarium culmorum, F. graminearum, F. langsethiae, F. moniliforme, F. proliferatum, F. subglutinans, F. solani* and *F. oxysporum* on wheat, barely, rye, oats, maize, cotton, soybean, sugarbeet and other hosts, *Microdochium nivale, Ustilago* spp., *Urocystis* spp., *Tifietia* spp. and *Claviceps purpurea* on a variety of hosts but particularly wheat, barley, turf and maize; *Ramularia* spp. on sugar beet, barley and other hosts; *Thielaviopsis basicola* on cotton, vegetables and other hosts; *Verticillium* spp. on cotton, vegetables and other hosts; post-harvest diseases particularly of fruit (for example *Penicillium digitatum, Penicillium italicum* and *Trichoderma viride* on oranges, *Colletotrichum musae* and *Gloeosporium musarum* on bananas and *Botrytis cinerea* on grapes); other pathogens on vines, notably *Eutypa lata, Guignardia bidwellii, Phellinus igniarus, Phomopsis viticola, Pseudopeziza tracheiphila* and *Stereum hirsutum*; other pathogens on trees (for example *Lophodermium seditiosum*) or lumber, notably *Cephaloascus fragrans, Ceratocystis* spp., *Ophiostoma piceae, Penicillium* spp., *Trichoderma pseudokoningfi, Trichoderma viride, Trichoderma harzianum, Aspergillus niger, Leptographium lindbergi* and *Aureobasidium pullulans*.

More preferably, the following pathogens are controlled: *Pyricularia oryzae* (*Magnaporthe grisea*) on rice and wheat and other *Pyricularia* spp. on other hosts; *Erysiphe cichoracearum* on cucurbits (for example melon); *Blumeria* (or *Erysiphe*) *graminis* (powdery mildew) on barley, wheat, rye and turf and other powdery mildews on various hosts, such as *Sphaerotheca macularis* on hops, *Sphaerotheca fusca* (*Sphaerotheca fuliginea*) on cucurbits (for example cucumber), *Leveillula taurica* on tomatoes, aubergine and green pepper, *Podosphaera leucotricha* on apples and *Uncinula necator* on vines; *Mycosphaerella graminicola* (*Septoria tritici*) and *Phaeosphaeria nodorum* (*Stagonospora nodorum* or *Septoria nodorum*), *Pseudocercosporella herpotrichoides* and *Gaeumannomyces graminis* on cereals (for example wheat, barley, rye), turf and other hosts; *Cercospora arachidicola* and *Cercosporidium personatum* on peanuts and other *Cercospora* spp. on other hosts, for example sugar beet, bananas, soya beans and rice; *Botrytis cinerea* (grey mould) on tomatoes, strawberries, vegetables, vines and other hosts and other *Botrytis* spp. on other hosts; *Alternaria* spp. on vegetables (for example carrots), oil-seed rape, apples, tomatoes, potatoes, cereals (for example wheat) and other hosts; *Venturia* spp. (including *Venturia inaequalis* (scab)) on apples, pears, stone fruit, tree nuts and other hosts; *Cladosporium* spp. on a range of hosts including cereals (for example wheat) and tomatoes; *Monilinia* spp. on stone fruit, tree nuts and other hosts; *Didymella* spp. on tomatoes, turf, wheat, cucurbits and other hosts; *Phoma* spp. on oil-seed rape, turf, rice, potatoes, wheat and other hosts; *Plasmopara viticola* on vines; *Plasmopara halstedii* on sunflower; other downy mildews, such as *Bremia lactucae* on lettuce, *Peronospora* spp. on soybeans, tobacco, onions and other hosts, *Pseudoperonospora humuli* on hops; *Peronosclerospora maedis, P. philippinensis* and *P. sorghi* on maize, sorghum and other hosts and *Pseudoperonospora cubensis* on cucurbits; *Pythium* spp. (including *Pythium ultimum*) on cotton, maize, soybean, sugarbeet, vegetables, turf and other hosts; *Phytophthora infestans* on potatoes and tomatoes and other *Phytophthora* spp. on vegetables, strawberries, avocado, pepper, ornamentals, tobacco, cocoa and other hosts; *Aphanomyces* spp. on sugarbeet and other hosts; *Thanatephorus cucumeris* on rice, wheat, cotton, soybean, maize, sugarbeet and turf and other hosts *Rhizoctonia* spp. on various hosts such as wheat and barley, peanuts, vegetables, cotton and turf; *Sclerotinia* spp. on turf, peanuts, potatoes, oil-seed rape and other hosts; *Sclerotium* spp. on turf, peanuts and other hosts; *Gibberella fujikuroi* on rice; *Colletotrichum* spp. on a range of hosts including turf, coffee and vegetables; *Laetisaria fuciformis* on turf; *Mycosphaerella* spp. on bananas, peanuts, citrus, pecans, papaya and other hosts; *Fusarium* spp. incl. *Fusarium culmorum, F. graminearum, F. langsethiae, F. moniliforme, F. proliferatum, F. subglutinans, F. solani* and *F. oxysporum* on wheat, barely, rye, oats, maize, cotton, soybean, sugarbeet and other hosts; and *Microdochium nivale*.

A compound of formula (I) may move acropetally, basipetally or locally in plant tissue to be active against one or more fungi. Moreover, a compound of formula (I) may be volatile enough to be active in the vapour phase against one or more fungi on the plant.

The invention therefore provides a method of combating or controlling phytopathogenic fungi which comprises applying a fungicidally effective amount of a compound of formula (I), or a composition containing a compound of formula (I), to a plant, to a seed of a plant, to the locus of the plant or seed or to soil or any other plant growth medium, e.g. nutrient solution.

The term "plant" as used herein includes seedlings, bushes and trees. Furthermore, the fungicidal method of the invention includes protectant, curative, systemic, eradicant and antisporulant treatments.

The compounds of formula (I) are preferably used for agricultural, horticultural and turfgrass purposes in the form of a composition.

In order to apply a compound of formula (I) to a plant, to a seed of a plant, to the locus of the plant or seed or to soil or any other growth medium, a compound of formula (I) is usually formulated into a composition which includes, in addition to the compound of formula (I), a suitable inert diluent or carrier and, optionally, a surface active agent (SFA). SFAs are chemicals that are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of fungi such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides a fungicidal composition comprising a fungicidally effective amount of a compound of formula (I) and a suitable carrier or diluent therefor.

In a still further aspect the invention provides a method of combating and controlling fungi at a locus, which comprises treating the fungi, or the locus of the fungi with a fungicidally effective amount of a composition comprising a compound of formula (I). The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone), alcohols (such as benzyl alcohol, furfuryl alcohol or butanol), N-alkylpyrrolidones (such as N-methylpyrrolidone or N-octyl-pyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at ambient temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents that have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurised, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier). Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts. Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefin sulphonates, taurates and lignosulphonates. Suitable SFAs of the amphoteric type include betaines, propionates and glycinates. Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying fungicidal compounds. For example, it may be applied, formulated or unformulated, to any part of the plant, including the foliage, stems, branches or roots, to the seed before it is planted or to other media in which plants are growing are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs, SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilisers (for example nitrogen-, potassium- or phosphorus-containing fertilisers). Suitable formulation types include granules of fertiliser. The mixtures suitably contain up to 25% by weight of the compound of formula (I).

The invention therefore also provides a fertiliser composition comprising a fertiliser and a compound of formula (I).

The compositions of this invention may contain other compounds having biological activity, for example micronutrients or compounds having similar or complementary fungicidal activity or which possess plant growth regulating, herbicidal, insecticidal, nematicidal or acaricidal activity.

By including another fungicide, the resulting composition may have a broader spectrum of activity or a greater level of intrinsic activity than the compound of formula (I) alone. Further the other fungicide may have a synergistic effect on the fungicidal activity of the compound of formula (I).

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergise the activity or complement the activity (for example by increasing the speed of effect or overcoming repellency) of the compound of formula (I); or help to overcome or prevent the development of resistance to individual components. The particular additional active ingredient will depend upon the intended utility of the composition.

Examples of further fungicidal compounds which may be included in the composition of the invention are AC 382042 (N-(1-cyano-1,2-dimethylpropyl)-2-(2,4-dichlorophenoxy) propionamide), acibenzolar-S-methyl, alanycarb, aldimorph, anilazine, azaconazole, azafenidin, azoxystrobin, benalaxyl, benomyl, benthiavalicarb, biloxazol, bitertanol, blasticidin S, boscalid (new name for nicobifen), bromuconazole, bupirimate, captafol, captan, carbendazim, carbendazim chlorhydrate, carboxin, carpropamid, carvone, CGA 41396, CGA 41397, chinomethionate, chlorbenzthiazone, chlorothalonil, chlorozolinate, clozylacon, copper containing compounds such as copper oxychloride, copper oxyquinolate, copper sulphate, copper tallate, and Bordeaux mixture, cyamidazosulfamid, cyazofamid (IKF-916), cyflufenamid, cymoxanil, cyproconazole, cyprodinil, debacarb, di-2-pyridyl disulphide 1,1'-dioxide, dichlofluanid, diclocymet, diclomezine, dichloran, diethofencarb, difenoconazole, difenzoquat, diflumetorim, O,O-di-iso-propyl-5-benzyl thiophosphate, dimefluazole, dimetconazole, dimethirimol, dimethomorph, dimoxystrobin, diniconazole, dinocap, dithianon, dodecyl dimethyl ammonium chloride, dodemorph, dodine, doguadine, edifenphos, epoxiconazole, ethaboxam, ethirimol, ethyl (Z)—N-benzyl-N([methyl(methyl-thioethylideneaminooxy-carbonyl)amino]thio)-β-alaninate, etridiazole, famoxadone, fenamidone, fenarimol, fenbuconazole, fenfuram, fenhexamid, fenoxanil (AC 382042), fenpiclonil, fenpropidin, fenpropimorph, fentin acetate, fentin hydroxide, ferbam, ferimzone, fluazinam, fludioxonil, flumetover, flumorph, fluoroimide, fluoxastrobin, fluquinconazole, flusilazole, flusulfamide, flutolanil, flutriafol, folpet, fosetyl-aluminium, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb, isopropanyl butyl carbamate, isoprothiolane, kasugamycin, kresoxim-methyl, LY186054, LY211795, LY 248908, mancozeb, maneb, mefenoxam, mepanipyrim, mepronil, metalaxyl, metalaxyl M, metconazole, metiram, metiram-zinc, metominostrobin, metrafenone, MON65500 (N-allyl-4,5-dimethyl-2-trimethylsilylthiophene-3-carboxamide), myclobutanil, NTN0301, neoasozin, nickel dimethyldithiocarbamate, nitrothale-isopropyl, nuarimol, ofurace, organomercury compounds, orysastrobin, oxadixyl, oxasulfuron, oxolinic acid, oxpoconazole, oxycarboxin, pefurazoate, penconazole, pencycuron, phenazin oxide, phosphorus acids, phthalide, picoxystrobin, polyoxin D, polyram, probenazole, prochloraz, procymidone, propamocarb, propamocarb hydrochloride, propiconazole, propineb, propionic acid, proquinazid, prothioconazole, pyraclostrobin, pyrazophos, pyrifenox, pyrimethanil, pyroquilon, pyroxyfur, pyrrolnitrin, quaternary ammonium compounds, quinomethionate, quinoxyfen, quintozene, silthiofam (MON 65500), S-imazalil, simeconazole, sipconazole, sodium pentachlorophenate, spiroxamine, streptomycin, sulphur, tebuconazole, tecloftalam, tecnazene, tetraconazole, thiabendazole, thifluzamide, 2-(thiocyano-methylthio)benzothiazole, thiophanate-methyl, thiram, tiadinil, timibenconazole, tolclofos-methyl, tolylfluanid, triadimefon, triadimenol, triazbutil, triazoxide, tricyclazole, tridemorph, trifloxystrobin, triflumizole, triforine, triticonazole, validamycin A, vapam, vinclozolin, XRD-563, zineb, ziram, zoxamide and the compounds of the formulae:

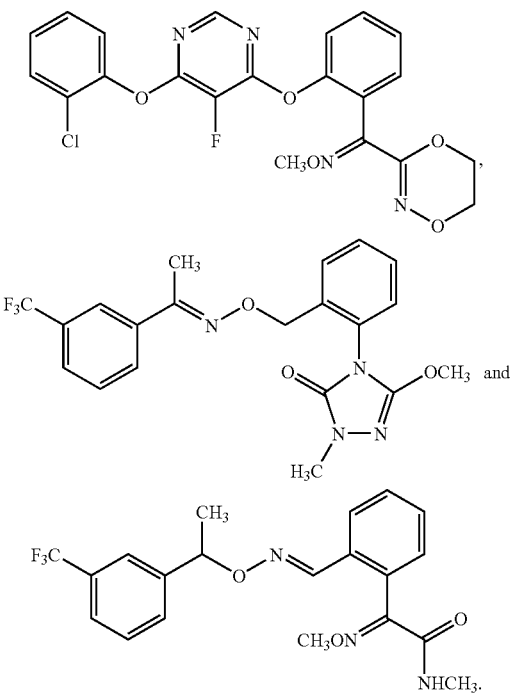

The compounds of formula (I) may be mixed with soil, peat or other rooting media for the protection of plants against seed-borne, soil-borne or foliar fungal diseases.

Some mixtures may comprise active ingredients, which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The invention is illustrated by the following Examples in which the following abbreviations are used:

| | |
|---|---|
| ml = milliliters | DMF = dimethylformamide |
| g = grammes | NMR = nuclear magnetic resonance |
| ppm = parts per million | HPLC = high performance |
| $M^+$ = mass ion | liquid chromatography |
| s = singlet | q = quartet |
| d = doublet | m = multiplet |
| br s = broad singlet | ppm = parts per million |
| t = triplet | |

EXAMPLE 1

This Example illustrates the preparation of 2-(3-bromo-quinolin-6-yloxy)-N-(2-butoxyimino-1,1-dimethyl-ethyl)-2-methylsulfanyl-acetamide Stage 1: Preparation of (3-Bromo-quinolin-6-yloxy)-methylsulfanyl-acetic acid according to the Scheme 3, eq. 1

Step 1: (3-Bromo-quinolin-6-yloxy)-methylsulfanyl-acetic acid methyl ester

3-Bromo-quinolin-6-ol (17.47 g) (preparation described in Liebigs Ann Chem., 1966, 98-106), was dissolved in dry DMF (150 ml). Chloro-methylsulfanyl-acetic acid methyl ester (18.07 g) and dry potassium carbonate (43.12 g) were added at room temperature (rt). The resulting suspension was stirred for 2 hours after which time the reaction mixture was diluted with ethyl acetate and poured onto sat. sodium hydrogen carbonate (200 ml). The two phases were separated and the aqueous layer was extracted three times with ethyl acetate (3×200 ml). The combined organic layers were dried over magnesium sulphate, filtered and evaporated. The residue was purified by column chromatography (heptane/ethyl acetate 7:3) to provide (3-bromo-quinolin-6-yloxy)-methyl-sulfanyl-acetic acid methyl ester as yellowish solid (24 g).

$^1$H NMR (CDCl$_3$) δ ppm: 8.81 (1H, d); 8.23 (1H, d); 8.02 (1H, d); 7.50 (1H, dd); 7.14 (1H, d); 5.72 (1H, s); 3.88 (3H, s); 2.24 (3H, s)

Step 2: Preparation of (3-Bromo-quinolin-6-yloxy)-methylsulfanyl-acetic acid

To a solution of (3-bromo-quinolin-6-yloxy)-methylsulfa-nyl-acetic acid methyl ester (20 g) from Step 1, Stage 1 above in ethanol (150 ml) at R.T. a 2 M solution of sodium hydroxide in water (35.06 ml) was added. The reaction mixture was stirred at R.T. for 2 hours. The reaction mixture was poured into ice-could water (200 ml) and acidified with a 2 M solution of hydrochloric acid in water (35.06 ml). The precipitate was filtered off and washed with water to give (3-Bromo-quinolin-6-yloxy)-methylsulfanyl-acetic acid as yellowish solid (18.79 g). $^1$H NMR (CDCl$_3$) δ ppm: 13.50 (1H, s br); 8.83 (1H, d); 8.59 (1H, d); 7.99 (1H, d); 7.57 (1H, dd); 7.50 (1H, d); 6.09 (1H, s); 2.17 (3H, s).

Stage 2: Preparation of 2-(3-bromo-quinolin-6-yloxy)-N-(2-butoxyimino-1,1-dimethyl-ethyl)-2-methylsulfanyl-acetamide according to Scheme 7

Step 1: Preparation of 2-(3-bromo-quinolin-6-yloxy)-N-(2-hydroxy-1,1-dimethyl-ethyl)-2-methyl-sulfanyl-acetamide (3-Bromo-quinolin-6-yloxy)-methylsulfanyl-acetic acid (23 g) from Example 1, Stage 1 above, 2-amino-2-methyl-1-propanol (8.06 ml), 1-hydroxy-7-azabenzotriazole (HOAT) (11.44 g), N-(3-dimethylaminopropyl)-N'-ethylcarbodiimide hydrochloride (EDC) (16.12 g) and triethylamine (14.63 ml) in dry DMF (175 ml) were stirred at rt for 16 hours. The reaction mixture was diluted with ethyl acetate and poured into 200 ml sat. NaHCO$_3$. The two phases were separated and the aqueous layer was extracted three times with ethyl acetate (3×200 ml). The organic layers were combined, dried over magnesium sulphate, filtered and evaporated. The residue was purified by column chromatography (heptane/ethyl acetate 7:13) to give 2-(3-bromo-quinolin-6-yloxy)-N-(2-hydroxy-1,1-dimethyl-ethyl)-2-methylsulfanyl-acetamide as a white solid (16.94 g). $^1$H NMR (DMSO) δ ppm: 8.82 (1H, d); 8.57 (1H, d); 7.99 (1H, d); 7.58 (1H, dd); 7.52 (1H, s); 7.44 (1H, d); 5.94 (1H, s); 4.99 (1H, t); 3.48-3.37 (2H, m); 2.15 (3H, s); 1.28 (3H, s); 1.26 (3H, s).

Step 2: Preparation of 2-(3-bromo-quinolin-6-yloxy)-N-(1,1-dimethyl-2-oxo-ethyl)-2-methylsulfa-nyl-acetamide 2-(3-Bromo-quinolin-6-yloxy)-N-(2-hydroxy-1,1-dim-ethyl-ethyl)-2-methylsulfanyl-acetamide (0.2 g) from Stage 2, Step 1 above in dichloromethane (15 ml) was treated with Dess-Martin periodinane (0.42 g). The reaction mixture was stirred at rt for 1 hour. The reaction mixture was quenched with sat. aqueous NaHCO$_3$ and sat. aqueous sodium thiosulphate. The reaction mixture was vigorously stirred at rt. for 30 minutes after which time the two phases were separated. The organic layer was washed with sat. aqueous. NaHCO$_3$. After separation the organic phase was dried over magnesium sulphate, filtered and evaporated. The residue was purified by column chromatography (heptane/ethyl acetate 1:1) to give 2-(3-bromo-quinolin-6-yloxy)-N-(1,1-dimethyl-2-oxo-ethyl)-2-methylsulfanyl-acetamide as white solid (0.188 g). $^1$H NMR (CDCl$_3$) δ ppm: 9.41 (1H, s); 8.83 (1H, d); 8.26 (1H, d); 8.08 (1H, d); 7.51 (1H, dd); 7.22 (1H, d); 5.69 (1H, s); 2.20 (3H, s); 1.53 (6H, s).

Step 3: Preparation of 2-(3-Bromo-quinolin-6-yloxy)-N-(2-butoxyimino-1,1-dimethyl-ethyl)-2-methylsulfanyl-acetamide 2-(3-Bromo-quinolin-6-yloxy)-N-(1,1-dimethyl-2-oxo-ethyl)-2-methylsulfanyl-acetamide (0.1 g) from Stage 2, Step 2 above, pyridine (0.022 ml) and O-n-butyl-hydroxylamine hydrochloride (0.035 g) in methanol (5 ml) were stirred at rt for 3 hours. The reaction mixture was diluted with ethyl acetate and poured onto sat. NaHCO$_3$ (30 ml). The two phases were separated and the aqueous layer was extracted with ethyl acetate (3×50 ml). The organic layers were combined, dried over magnesium sulphate, filtered and evaporated. The residue was purified by column chromatography (heptane/ethyl acetate 3:1) to give 2-(3-bromo-quinolin-6-yloxy)-N-(2-butoxyimino-1,1-dimethyl-ethyl)-2-methylsulfanyl-acetamide as white solid (0.115 g). $^1$H NMR (CDCl$_3$) δ ppm: 8.81 (1H, d); 8.24 (1H, d); 8.04 (1H, d); 7.71 (1H, s); 7.45 (1H, dd); 7.39

(1H, s); 7.17 (1H, d); 5.64 (1H, s); 4.08 (2H, t); 2.19 (3H, s); 1.68-1.58 (8H, m); 1.45-1.36 (2H, m), 0.94 (3H, t).

EXAMPLE 2

This Example illustrates the preparation of 2-amino-2-methyl-propionaldehyde O-methyl-oxime according to Scheme 9.

Step 1: Preparation of 2-(2-hydroxy-1,1-dimethyl-ethyl)-isoindole-1,3-dione 177.7 g of phtalic anhydride and 91.9 g of 2-amino-2-methyl-propan-(1)-ol were dissolved in 750 ml of DMF and after the addition of a catalytic amount of p-toluene sulfonic acid stirred the mixture was stirred for 3 hours at 145° C. The reaction mixture was then concentrated under reduced pressure and the residue was diluted with 1N aqueous HCl and extracted with ethyl acetate. The organic was washed with 1N NaOH and 2 times with $H_2O$. The organic layer was dried over magnesium sulfate and the solvent was evaporated under reduced pressure to give 144.1 g of an oil, which was used in the next step without further purification.

1H NMR (CDCl3) δ ppm: 1.6 (6H, s); 3.52 (1H, t); 3.93 (2H, d); 7.20-7.23 (2H, m); 7.28-7.83 (2H, m)

Step 2: Preparation of 2-(1,3-Dioxo-1,3-dihydro-isoindol-2-yl)-2-methyl propionaldehyde 11.9 g of sulfur trioxide pyridine complex dissolved in 75 ml DMSO was added over a period of 20 minutes at room temperature to a solution of 5.48 g of 2-(2-hydroxy-1,1-dimethyl-ethyl)-isoindole-1,3-dione from Step 1 and 7.59 g of triethylamine in 780 ml DMSO. The reaction mixture was stirred at room temperature for 30 minutes, poured onto ice/water and extracted 3 times with tert-butyl methyl ether. The organic was washed with 1N HCl and 2 times $H_2O$, dried over magnesium sulfate and the solvent was evaporated under reduced pressure to give 4.92 g crystals (mp 80-82° C.), which were used in the next step without further purification.

1H NMR (CDCl3) δ ppm: 1.66 (6H, s); 7.72-7.88 (4H, m); 9.6 (1H, s)

Step 3: Preparation of 2-(1,3-dioxo-1,3-dihydro-isoindol-2-yl)-2-methyl-propionaldehyde O-methyl-oxime 1.35 g of N-methyl hydroxylamine.HCl and 1.33 g of sodium acetate were added to a solution of 3.53 g 2-(1,3-dioxo-1,3-dihydro-isoindol-2-yl)-2-methyl-propionaldehyde from Step 2 in 35 ml of ethanol and 10 ml of chloroform and stirred for 12 h at room temperature. After removal of salts by filtration, the solvents were removed under reduced pressure. Purification of the crude residue by chromatography (silica gel; hexane:ethyl acetate 4:1) provided 1.73 g of the solid product, 2-(1,3-dioxo-1,3-dihydro-isoindol-2-yl)-2-methyl-propionaldehyde O-methyl-oxime.

1H NMR (CDCl3) δ ppm: 1.82 (6H, s); 3.88 (3H, s); 7.65-7.7.3 (5H, m)

Step 4: Preparation of 2-amino-2-methyl-propionaldehyde O-methyl-oxime

A mixture of 1.72 g of 2-(1,3-dioxo-1,3-dihydro-isoindol-2-yl)-2-methyl-propionaldehyde O-methyl-oxime from Step 3 above and hydrazine hydrate was refluxed for 2 hours. The reaction mixture was filtered to remove phtalic hydrazide and the resulting liquid was evaporated to give 240 mg oil, which was used in the next step (Example xx) without further purification.

EXAMPLE 3

This Example illustrates the preparation of 2-(3-bromo-quinolinyl-6-oxy)-2-methylthio-N-(2-methoxyimino-1,1-dimethyl-ethyl)acetamide according to the second step shown in Scheme 3.

328 mg of 2-(3-bromoquinolinyl-6-oxy)-2-methylthioacetic acid and 354 mg of triethyl amine were dissolved in 10 ml of acetonitrile, followed by the addition of 150 mg of HOBT and 353 mg of TBTU. The reaction mixture was stirred for 5 minutes, then 209 mg crude 2-methyl-propionaldehyde O-methyl-oxime from Step 4 above were added. After stirring the reaction mixture for 15 hours at room temperature, ethyl acetate was added. Water was added and the aqueous phase was extracted with ethyl acetate. The combined organic extracts were dried over magnesium sulphate, filtered and evaporated under reduced pressure. HPLC chromatography provided 2-(3-bromoquinolinyl-6-oxy)-2-methylthio-N-(2-methoxyimino-1,1-dimethyl-ethyl)acetamide.

$^1$H NMR (CDCl$_3$) δ ppm: 8.81 (1H, d); 8.25 (1H, d); 8.05 (1H, d); 7.59 (1H, s br); 7.46 (1H, dd); 7.40 (1H, d); 7.18 (1H, d); 5.64 (1H, s); 3.88 (3H, s); 2.20 (3H, s); 1.60 (3H, s); 1.60 (3H, s).

EXAMPLE 4

Example 4 provides characterising NMR data and/or melting points for compounds that are in part listed in the Tables cited above and have been prepared using procedures similar to those described in Examples 1-3 unless specified otherwise. Unless stated otherwise, the $^1$H NMR signals reported are those that characterize to the major diasteroisomer.

The following oxime of the general formula (1) was prepared using similar procedures to those described in Example 1, Stage 1 and 2 starting from benzothiazol-6-ol (prepared as described in WO 2004108663 A1) and chloro-methylsulfanyl-acetic acid methyl ester:

Compound No. 1: 2-(Benzothiazol-6-yloxy)-N-(2-methoxy-imino-1,1-dimethyl-ethyl)-2-methylsulfa-nyl-acetamide $^1$H NMR (CDCl$_3$) δ ppm: 8.82 (1H, sm); 8.09 (1H, sm); 7.62 (1H, sm); 7.55 (1H, s br); 7.39 (1H, s); 7.13 (1H, sm); 5.62 (1H, s); 3.39 (3H, s); 2.20 (3H, s); 1.60 (3H, s); 1.58 (3H, s); mp 158-161° C.

The following oximes of the general formula (1) were prepared using similar procedures to those described in Example 1, Stage 1 and 2 starting from 3-iodo-quinolin-6-ol (prepared as described in WO 2006058700 A1) and 2-chloro-butyric acid methyl ester:

Compound No. 2: 2-(3-Iodo-quinolin-6-yloxy)-N-(2-methoxy-imino-1,1-dimethyl-ethyl)-butyramide $^1$H NMR (CDCl$_3$) δ ppm: 8.91 (1H, d); 8.41 (1H, d); 8.00 (1H, d); 7.43 (1H, dd); 7.30 (1H, s); 7.17 (1H, s br); 6.97 (1H, d); 4.58 (1H, t); 3.76 (3H, s); 2.09-1.98 (2H, m); 1.49 (3H, s); 1.44 (3H, s); 1.08 (3H, t).

Compound No. 3: N-(2-Ethoxyimino-1,1-dimethyl-ethyl)-2-(3-iodo-quinolin-6-yloxy)-butyramide $^1$H NMR (CDCl$_3$) δ ppm: 8.91 (1H, d); 8.40 (1H, d); 7.99 (1H, d); 7.42 (1H, d); 7.28 (1H, s); 7.26 (1H, s br); 6.97 (1H, d); 4.57 (1H, t); 4.05-3.93 (2H, m); 2.10-1.98 (2H, m); 1.50 (3H, s); 1.44 (3H, s); 1.17 (3H, t); 1.08 (3H, t)

Compound No. 4: N-(2-Allyloxyimino-1,1-dimethyl-ethyl)-2-(3-iodo-quinolin-6-yloxy)-butyramide $^1$H NMR (CDCl$_3$) δ ppm: 8.91 (1H, d); 8.41 (1H, d); 7.98 (1H, d); 7.42 (1H, dd); 7.34 (1H, s); 7.20 (1H, s br); 6.97 (1H d); 5.93-5.84 (1H, m); 5.24 (1H, dd); 5.17 (1H, dd); 4.57 (1H, t); 4.44 (2H, d); 2.10-1.97 (2H, m); 1.50 (3H, s); 1.45 (3H, s); 1.07 (3H, t)

The following oximes of the general formula (1) were prepared using similar procedures to those described in Example 1, Stage 1 and 2 starting from 3-iodo-8-methylquinolin-6-ol (prepared as described in WO 2006058700 A1) and 2-chloro-butyric acid methyl ester:

Compound No. 5: 2-(3-Iodo-8-methyl-quinolin-6-yloxy)-N-(2-methoxyimino-1,1-dimethyl-ethyl)-butyramide $^1$H NMR (CDCl$_3$) δ ppm: 8.91 (1H, d); 8.36 (1H, d); 7.31 (1H, s); 7.29 (1H, d); 7.15 (1H, s br); 6.80 (1H, d); 4.56 (1H, t); 3.77 (3H, s); 2.74 (3H, s); 2.08-1.96 (2H, m); 1.49 (3H, s); 1.44 (3H, s); 1.07 (3H, t).

Compound No. 6: N-(2-Ethoxyimino-1,1-dimethyl-ethyl)-2-(3-iodo-8-methyl-quinolin-6-yloxy)-butyramide $^1$H NMR (CDCl$_3$) δ ppm: 8.91 (1H, d); 8.36 (1H, s); 7.29 (1H, d); 7.29 (1H, s); 7.24 (1H, s br); 6.80 (1H, d); 4.55 (1H, t); 4.04-3.96 (2H, m); 2.73 (3H, s); 2.09-196 (2H, m); 1.49 (3H, s); 1.44 (3H, s); 1.18 (3H, t); 1.07 (3H, t)

Compound No. 7: N-(2-allyloxyimino-1,1-dimethyl-ethyl)-2-(3-iodo-8-methyl-quinolin-6-yloxy)-butyramide $^1$H NMR (CDCl$_3$) δ ppm: 8.91 (1H, d); 8.36 (1H, d); 7.35 (1H, s); 7.28 (1H, d); 7.19 (1H, s br); 6.80 (1H, d); 5.94-5.84 (1H, m); 5.24 (1H, dd); 5.16 (1H, dd); 4.55 (1H, t); 4.44 (2H, d); 2.74 (3H, s); 2.09-1.96 (2H, m); 1.50 (3H, s); 1.44 (3H, s); 1.06 (3H, t)

The following oximes of the general formula (1) were prepared using similar procedures to those described in Example 1, Stage 1 and 2 starting from 3-bromo-quinolin-6-ol (preparation described in Liebigs Ann Chem., 1966, 98-106) and chloro-methylsulfanyl-acetic acid methyl ester:

Compound No. 8: 2-(3-Bromo-quinolin-6-yloxy)-N-(1,1-dimethyl-2-phenoxyimino-ethyl)-2-methylsulfanyl-acetamide $^1$H NMR (CDCl$_3$) δ ppm: 8.82 (1H, d); 8.20 (1H, d); 8.06 (1H, d); 7.84 (1H, s); 7.58 (1H, s, br); 7.47 (1H, dd); 7.33-7.04 (6H, m); 5.68 (1H, s); 2.21 (3H, s); 1.69 (6H, s).

Compound No. 9: 2-(3-Bromo-quinolin-6-yloxy)-N-[2-(4-chloro-benzyloxyimino)-1,1-dimethyl-ethyl]-2-methylsulfanyl-acetamide $^1$H NMR (CDCl$_3$) δ ppm: 8.83 (1H, d); 8.24 (1H, d); 8.04 (1H, d); 7.52 (1H, s br); 7.49 (1H, s); 7.36-7.26 (6H, m); 7.15 (1H, d); 5.61 (1H, s); 5.05 (2H, s); 2.15 (3H, s); 1.60 (3H, s); 1.57 (3H, s).

Compound No. 10: 2-(3-Bromo-quinolin-6-yloxy)-N-[1,1-dimethyl-2-(2,4,5-trichloro-benzyloxyimino)-ethyl]-2-methylsulfanyl-acetamide $^1$H NMR (CDCl$_3$) δ ppm: 8.82 (1H, d); 8.24 (1H, d); 8.02 (1H, d); 7.59 (1H, s); 7.49 (2H, d); 7.43 (1H, s br); 7.36 (1H, dd); 7.16 (1H, d); 5.62 (1H, s); 5.13 (2H, s); 2.16 (3H, s); 1.60 (3H, s); 1.58 (3H, s).

Compound No. 11: 2-[2-[2-(3-Bromo-quinolin-6-yloxy)-2-methylsulfanyl-acetylamino]-2-methyl-prop-(E or Z)-ylideneaminooxy]-2-methyl-propionic acid ethyl ester $^1$H NMR (CDCl$_3$) δ ppm: 8.82 (1H, d); 8.28 (1H, d); 8.06 (1H, d); 7.70 (1H, s br); 7.52 (1H, dd); 7.45 (1H, s); 7.22 (1H, d); 5.63 (1H, s); 4.22-4.13 (2H, m); 2.13 (3H, s); 1.61 (3H, s); 1.59 (3H, s); 1.55 (3H, s); 1.52 (3H, s), 1.21 (3H, t).

Compound No. 12: 2-(3-Bromo-quinolin-6-yloxy)-N-(2-tert-butoxyimino-1,1-dimethyl-ethyl)-2-methylsulfanyl-acetamide $^1$H NMR (CDCl$_3$) δ ppm: 8.82 (1H, d); 8.24 (1H, d); 8.04 (1H, d); 7.89 (1H, s br); 7.44 (1H, dd); 7.31 (1H, s); 7.18 (1H, d); 5.65 (1H, s); 2.19 (3H, s); 1.61 (3H, s); 1.53 (3H, s); 1.30 (9H, s)

Compound No. 13: N-(2-Allyloxyimino-1,1-dimethyl-ethyl)-2-(3-bromo-quinolin-6-yloxy)-2-methylsulfanyl-acetamide $^1$H NMR (CDCl$_3$) δ ppm: 8.82 (1H, d); 8.25 (1H, d); 8.04 (1H, d); 7.64 (1H, s br); 7.44 (1H, dd); 7.44 (1H, s); 7.18 (1H, d); 6.04-5.94 (1H, m); 5.64 (1H, s); 5.35-5.23 (2H, m); 4.57 (2H, m); 2.19 (3H, s); 1.61 (3H, s); 1.57 (3H, s).

Compound No. 14: 2-(3-Bromo-quinolin-6-yloxy)-N-(2-butoxyimino-1,1-dimethyl-ethyl)-2-methylsulfanyl-acetamide $^1$H NMR (CDCl$_3$) δ ppm: 8.81 (1H, d); 8.24 (1H, d); 8.04 (1H, d); 7.71 (1H, s br); 7.45 (1H, dd); 7.39 (1H, s); 7.17 (1H, d); 5.64 (1H, s); 4.08 (2H, t); 2.19 (3H, s); 1.68-1.58 (8H, m); 1.45-1.36 (2H, m), 0.94 (3H, t).

Compound No. 15: 2-(3-Bromo-quinolin-6-yloxy)-N-(2-methoxyimino-1,1-dimethyl-ethyl)-2-methylsulfanyl-acetamide $^1$H NMR (CDCl$_3$) δ ppm: 8.81 (1H, d); 8.25 (1H, d); 8.05 (1H, d); 7.59 (1H, s br); 7.46 (1H, dd); 7.40 (1H, d); 7.18 (1H, d); 5.64 (1H, s); 3.88 (3H, s); 2.20 (3H, s); 1.60 (3H, s); 1.60 (3H, s).

Compound No. 16: 2-(3-Bromo-quinolin-6-yloxy)-N-(2-ethoxyimino-1,1-dimethyl-ethyl)-2-methylsulfanyl-acetamide $^1$H NMR (CDCl$_3$) δ ppm: 8.82 (1H, d); 8.25 (1H, d); 8.05 (1H, d); 7.69 (1H, s br), 7.45 (1H, dd); 7.39 (1H, s); 7.18 (1H, d); 5.65 (1H, s); 4.10 (2H, q); 2.2 (3H, s); 1.61 (3H, s); 1.58 (3H, s); 1.28 (3H, t).

Compound No. 17: 2-(3-Bromo-quinolin-6-yloxy)-N-(1,1-dimethyl-2-prop-2-ynyloxyimino-ethyl)-2-methylsulfanyl-acetamide $^1$H NMR (CDCl$_3$) δ ppm: 8.82 (1H, d); 8.25 (1H, d); 8.04 (1H, d); 7.59 (1H, s br); 7.49 (1H, 7.48 (1H, dd); 7.20 (1H, d); 5.64 (1H, s); 4.66 (2H, s); 2.47 (1H, t); 2.19 (3H, s); 1.62 (3H, s); 1.60 (3H, s).

Compound No. 18: 2-(3-Bromo-quinolin-6-yloxy)-N-(2-iso-butoxyimino-1,1-dimethyl-ethyl)-2-methyl-sulfanyl-acetamide $^1$H NMR (CDCl$_3$) δ ppm: 8.82 (1H, d); 8.25 (1H, d); 8.04 (1H, d); 7.69 (1H, s br); 7.45 (1H, dd); 7.41 (1H, s); 7.18 (1H, d); 5.64 (1H, s); 3.83 (2H, d); 2.19 (3H, s); 2.05-1.93 (1H, m); 1.59 (3H, s); 1.58 (3H, s); 0.95 (6H, dd).

Compound No. 19: 2-(3-Bromo-quinolin-6-yloxy)-N-(2-hydroxyimino-1,1-dimethyl-ethyl)-2-methyl-sulfanyl-acetamide $^1$H NMR (CDCl$_3$) δ ppm: 8.81 (1H, d); 8.25 (1H, d); 8.04 (1H, d); 7.92 (1H, d); 7.55 (1H, s br); 7.52 (1H, s); 7.43 (1H, dd); 7.18 (1H, d); 5.62 (1H, s); 2.18 (3H, s); 1.63 (3H, s); 1.60 (3H, s).

The following oximes of the general formula (1) were prepared using similar procedures to those described in Example 1, Stage 1 and 2 starting from 3-bromo-8-methyl-quinolin-6-ol (prepared as described in WO 2006058700 A1) and chloro-methylsulfanyl-acetic acid methyl ester:

Compound No. 20: 2-(3-Bromo-8-methyl-quinolin-6-yloxy)-N-[1,1-dimethyl-2-(2,4,5-trichloro-benzyloxyimino)-ethyl]-2-methylsulfanyl-acetamide $^1$H NMR (CDCl$_3$) δ ppm: 8.82 (1H, d); 8.20 (1H, d); 7.61 (1H, s); 7.48 (2H, d); 7.38 (1H, s br); 7.27 (1H, d); 6.99 (1H, d); 5.61 (1H, s); 5.11 (2H, s); 2.76 (3H, s); 2.16 (3H, s); 1.60 (3H, s); 1.58 (3H, s).

Compound No. 21: 2-(3-Bromo-8-methyl-quinolin-6-yloxy)-N-[2-(4-chloro-benzyloxyimino)-1,1-dimethyl-ethyl]-2-methylsulfanyl-acetamide $^1$H NMR (CDCl$_3$) δ ppm: 8.82 (1H, d); 8.20 (1H, d); 7.49 (1H, s); 7.46 (1H, s br); 7.31-7.26 (6H, m); 7.00 (1H, d); 5.60 (1H, s); 5.04 (2H, s); 2.77 (3H, s); 2.16 (3H, s); 1.59 (3H, s); 1.57 (3H, s).

Compound No. 22: 2-(3-Bromo-8-methyl-quinolin-6-yloxy)-N-(2-tert-butoxyimino-1,1-dimethyl-ethyl)-2-methylsulfanyl-acetamide $^1$H NMR (CDCl$_3$) δ ppm: 8.82 (1H, d); 8.20 (1H, d); 7.93 (1H, s br); 7.33 (1H, d); 7.33 (1H, s); 7.00 (1H, d); 5.64 (1H, s); 2.75 (3H, s); 2.18 (3H, s); 1.61 (3H, s); 1.56 (3H, s); 1.31 (9H, s).

Compound No. 23: 2-(3-Bromo-8-methyl-quinolin-6-yloxy)-N-(1,1-dimethyl-2-phenoxyimino-ethyl)-2-methylsulfanyl-acetamide $^1$H NMR (CDCl$_3$) δ ppm: 8.81 (1H, d); 8.17 (1H, d); 7.84 (1H, s); 7.62 (1H, s br); 7.34-7.30 (3H, m); 7.17-7.01 (4H, m); 5.66 (1H, s); 2.75 (3H, s); 2.20 (3H, s); 1.69 (6H, s).

Compound No. 24: 2-[2-[2-(3-Bromo-8-methyl-quinolin-6-yloxy)-2-methylsulfanyl-acetylamino]-2-methyl-prop-(E)-ylideneaminooxy]-2-methyl-propionic acid ethyl ester $^1$H NMR (CDCl$_3$) δ ppm: 8.81 (1H, d); 8.23 (1H, d); 7.74 (1H, s br); 7.41 (1H, s); 7.40 (1H, d); 7.01 (1H, d); 5.63 (1H, s); 4.25-4.08 (2H, m); 2.80 (3H, s); 2.12 (3H, s); 1.62 (3H, s); 1.59 (3H, s); 1.55 (3H, s); 1.53 (3H, s) 1.21 (3H, t).

Compound No. 25: 2-(3-Bromo-8-methyl-quinolin-6-yloxy)-N-(2-isobutoxyimino-1,1-dimethyl-ethyl)-2-methylsulfanyl-acetamide $^1$H NMR (CDCl$_3$) δ ppm: 8.82 (1H, d); 8.21 (1H, d); 7.70 (1H, s br); 7.41 (1H, s); 7.30 (1H, d); 7.01 (1H, d); 5.63 (1H, s); 8.83 (2H, d); 2.74 (3H, s); 2.17 (3H, s); 2.05-1.95 (1H, m); 1.58 (3H, s); 1.57 (3H, s); 0.94 (6H, dd).

Compound No. 26: 2-(3-Bromo-8-methyl-quinolin-6-yloxy)-N-(2-methoxyimino-1,1-dimethyl-ethyl)-2-methylsulfanyl-acetamide $^1$H NMR (CDCl$_3$) δ ppm: 8.82 (1H, d); 8.21 (1H, d); 7.58 (1H, s br); 7.41 (1H, s); 7.02 (1H, d); 5.63 (1H, s); 3.88 (3H, s); 2.77 (3H, s); 2.20 (3H, s); 1.60 (3H, s); 1.58 (3H, s).

Compound No. 27: 2-(3-bromo-8-methyl-quinolin-6-yloxy)-N-(2-ethoxyimino-1,1-dimethyl-ethyl)-2-methylsulfanyl-acetamide $^1$H NMR (CDCl$_3$) δ ppm: 8.81 (1H, d); 8.21 (1H, d); 7.67 (1H, s br); 7.40 (1H, s); 7.31 (1H, d); 7.01 (1H, d); 5.63 (1H, s); 4.14 (2H, q); 2.74 (3H, s); 2.19 (3H, s); 1.61 (3H, s); 1.58 (3H, s); 1.26 (3H, t).

Compound No. 28: N-(2-Allyloxyimino-1,1-dimethyl-ethyl)-2-(3-bromo-8-methyl-quinolin-6-yloxy)-2-methylsulfanyl-acetamide $^1$H NMR (CDCl$_3$) δ ppm: 8.82 (1H, d); 8.21 (1H, d); 7.63 (1H, s br); 7.45 (1H, s); 7.31 (1H, d); 7.01 (1H, d); 6.05-5.95 (1H, m); 5.62 (1H, s); 5.35-5.23 (2H, m); 4.58-4.56 (2H, m); 2.77 (3H, s); 2.19 (3H, s); 1.60 (3H, s); 1.58 (3H, s).

Compound No. 29: 2-(3-Bromo-8-methyl-quinolin-6-yloxy)-N-(1,1-dimethyl-2-prop-2-ynyloxyimino-ethyl)-2-methylsulfanyl-acetamide $^1$H NMR (CDCl$_3$) δ ppm: 8.82 (1H, d); 8.21 (1H, d); 7.58 (1H, s br); 7.50 (1H, s); 7.36 (1H, d); 7.02 (1H, d); 5.62 (1H, s); 4.67 (2H, s); 2.77 (3H, s); 2.47 (1H, t); 2.20 (3H, s); 1.62 (3H, s); 1.60 (3H, s)

Compound No. 30: 2-(3-Bromo-8-methyl-quinolin-6-yloxy)-N-(2-butoxyimino-1,1-dimethyl-ethyl)-2-methylsulfanyl-acetamide $^1$H NMR (CDCl$_3$) δ ppm: 8.81 (1H, d); 8.21 (1H, d); 7.69 (1H, s br); 7.39 (1H, s); 7.31 (1H, d); 7.01 (1H, d); 5.63 (1H, s); 4.07 (2H, t); 2.72 (3H, s); 2.19 (3H, s); 1.70-1.55 (8H, m); 1.45 (2H, m); 0.96 (3H, t).

Compound No. 31: 2-(3-Bromo-8-methyl-quinolin-6-yloxy)-N-(2-hydroxyimino-1,1-dimethyl-ethyl)-2-methylsulfanyl-acetamide $^1$H NMR (CDCl$_3$) δ ppm: 8.81 (1H, d); 8.21 (1H, d); 7.65 (1H, s); 7.52 (1H, s); 7.51 (1H, s); 7.29 (1H, d); 7.02 (1H, d); 5.62 (1H, s); 2.75 (3H, s); 2.18 (3H, s); 1.62 (3H, s); 1.60 (3H, s).

Compound No. 32: 2-(3-Bromo-8-methyl-quinolin-6-yloxy)-N-{2-[(E)-methoxyimino]-1,1-dimethyl-propyl}-2-methylsulfanyl-acetamide $^1$H NMR (CDCl$_3$) δ ppm: 8.81 (1H, d); 8.33 (1H, s br); 8.20 (1H, d); 7.33 (1H, d); 7.01 (1H, d); 5.62 (1H, s); 3.92 (3H, s); 2.77 (3H, s); 2.20 (3H, s); 1.85 (3H, s); 1.62 (3H, s); 1.57 (3H, s).

The following oximes of the general formula (1) were prepared using similar procedures to those described in Example 1, Stage 1 and 2 starting from 3,8-dibromo-quinolin-6-ol (prepared as described in WO 2004047538 A1) and chloro-methylsulfanyl-acetic acid methyl ester:

Compound No. 33: 2-(3,8-Dibromo-quinolin-6-yloxy)-N-(2-ethoxyimino-1,1-dimethyl-ethyl)-2-methylsulfanyl-acetamide $^1$H NMR (CDCl$_3$) δ ppm: 8.92 (1H, d); 8.28 (1H, d); 7.83 (1H, d); 7.68 (1H, s br); 7.39 (1Hs); 7.17 (1H, d); 5.63 (1H, s); 4.15 (2H, q); 2.19 (3H, s); 1.59 (3H, s); 1.56 (3H, s); 1.30 (3H, t)

Compound No. 34: 2-(3,8-Dibromo-quinolin-6-yloxy)-N-(2-methoxyimino-1,1-dimethyl-ethyl)-2-methylsulfanyl-acetamide $^1$H NMR (CDCl$_3$) δ ppm: 8.92 (1H, d); 8.28 (1H, d); 7.85 (1H, d); 7.59 (1H, s br); 7.40 (1H, s); 7.17 (1H, d); 5.63 (1H, s); 3.90 (3H, s); 2.20 (3H, s); 1.58 (6H, s)

The following oximes of the general formula (1) were prepared using similar procedures to those described in Example 1, Stage 1 and 2 starting from 3-bromo-8-chloro-quinolin-6-01 (prepared as described in WO 2004108663 A1) and chloro-methylsulfanyl-acetic acid methyl ester:

Compound No. 35: 2-(3-Bromo-8-chloro-quinolin-6-yloxy)-N-(2-methoxyimino-1,1-dimethyl-ethyl)-2-methylsulfanyl-acetamide $^1$H NMR (CDCl$_3$) δ ppm: 8.92 (1H, d); 8.28 (1H, d); 8.63 (1H, d); 8.59 (1H, s br); 7.40 (1H, s); 7.13 (1H, d); 5.63 (1H, s); 3.90 (3H, s); 2.20 (3H, s); 1.58 (3H, s); 1.57 (3H, s)

Compound No. 36: 2-(3-Bromo-8-chloro-quinolin-6-yloxy)-N-(2-ethoxyimino-1,1-dimethyl-ethyl)-2-methylsulfanyl-acetamide $^1$H NMR (CDCl$_3$) δ ppm: 8.92 (1H, d); 8.27 (1H, d); 7.68 (1H, s br); 7.56 (1H, d); 7.39 (1H, s); 7.17 (1H, d); 5.63 (1H, s); 4.17 (2H, q); 2.20 (3H, s); 1.61 (3H, s); 1.58 (3H, s); 1.30 (3H, t)

The following quinolin-6-ol derived oximes of the general formula (1) were prepared starting from 3-bromo-quinolin-6-ol, 3-iodo-quinolin-6-ol or 3-ethynyl quinolin-6-ol and chloro-methylsulfanyl-acetic acid methyl ester or directly from 2-(3-bromo or iodo-quinolin-6-yloxy)-N-(2-methoxy-imino-1,1-dimethyl-ethyl)-2-methylsulfanyl-acetamide as illustrated below in Examples 5:

EXAMPLE 5

This Example illustrates the preparation of 2-(3-ethynyl-quinolin-6-yloxy)-N-(2-methoxyimino-1,1-dimethyl-ethyl)-2-methylsulfanyl-acetamide starting from (3-bromo-quinolin-6-yloxy)-methylsulfanyl-acetic acid methyl ester.

Step 1: Methylsulfanyl-(3-trimethylsilanylethynyl-quinolin-6-yloxy)-acetic acid methyl ester (3-Bromo-quinolin-6-yloxy)-methylsulfanyl-acetic acid methyl ester (9.5 g), bis(palladium(II)triphenylphosphine) dichloride (877 mg), copper iodine (200 mg) and diisoproylamine (17.5 ml) were dissolved in THF (150 ml) and deoxygenated with nitrogen. Trimethylsilylacetylene (7.1 ml) was added dropwise during 10 min. The reaction mixture was heated up to 45° C. and was stirred at that temperature for 36 hrs. The reaction mixture was diluted with ethyl acetate and was washed with 2×200 ml sat. aq. NaCl. The aqueous layer was extracted with 2×500 ml ethyl acetate. All organic phases were combined, dried over sodium sulfate, filtered and evaporated. The residue was purified by column chromatography (heptane/ethyl acetate 4:1) to provide methylsulfanyl-(3-trimethylsilanylethynyl-quinolin-6-yloxy)-acetic acid methyl ester (7.6 g) as yellowish oil.

1H NMR (CDCl3) δ ppm: 8.81 (1H, d); 8.16 (1H, d); 8.03 (1H, d); 7.48 (1H, dd); 7.17 (1H, d); 5.73 (1H, s); 3.88 (3H, s); 2.24 (3H, s); 0.29 (9H, s)

Step 2: (3-Ethynyl-quinolin-6-yloxy)-methylsulfanyl-acetic acid

To a solution of methylsulfanyl-(3-trimethylsilanylethynyl-quinolin-6-yloxy)-acetic acid methyl ester (5 g) from Step 1, in ethanol (50 ml), a 2M solution of sodium hydroxide in water (9.74 ml) was added. The reaction mixture was stirred at room temperature for 1 hour. The reaction mixture was poured into ice-cold water (200 ml) and acidified with a 2 M solution of hydrochloric acid in water (9.74 ml). The precipitate was filtered off and washed with water to give (3-ethynyl-quinolin-6-yloxy)-methylsulfanyl-acetic acid as yellowish solid (3.53 g).

1H NMR (DMSO) d ppm: 13.45 (1H, s); 8.73 (1H, d); 8.37 (1H, d); 7.93 (1H, d); 7.51 (1H, dd); 7.47 (1H, d); 6.03 (1H, s); 4.45 (1H, s); 2.11 (3H, s)

Step 3: Amidation of 2-(3-ethynyl-quinolin-6-yloxy)-N-(2-methoxyimino-1,1-dimethyl-ethyl)-2-methylsulfanyl-acetamide from Step 2 Above with 2-methyl-propionaldehyde O-methyl-oxime from Example 2, Step 4 Using a Procedure Similar to that Described in Example 3 Provided Compound No. 38: 2-(3-Ethynyl-quinolin-6-yloxy)-N-(2-methoxyimino-1,1-dimethyl-ethyl)-2-methyl-sulfanyl-acetamide $^1$H NMR (CDCl$_3$) δ ppm: 8.86 (1H, d); 8.21 (1H, d); 8.06 (1H, d); 7.59 (1H, s br); 7.47 (1H, dd); 7.41 (1H, s); 7.23 (1H, d); 5.65 (1H, s); 3.88 (3H, s); 3.29 (1H, s); 2.20 (3H, s); 1.60 (3H, s); 1.58 (3H, s)

Alternatively, compound No. 38 (2-(3-ethynyl-quinolin-6-yloxy)-N-(2-methoxyimino-1,1-dimethyl-ethyl)-2-methylsulfanyl-acetamide) can be prepared via desilylation of Compound No. 37, N-(2-methoxyimino-1,1-dimethyl-ethyl)-2-methylsulfanyl-2-(3-trimethylsilanylethynyl-quinolin-6-yloxy)-acetamide: $^1$H NMR (CDCl$_3$) δ ppm: 8.82 (1H, d); 8.17 (1H, d); 8.04 (1H, d); 7.60 (1H, s br); 7.45 (1H, dd); 7.41 (1H, s); 7.21 (1H, d); 5.64 (1H, s); 3.88 (3H, s); 2.20 (3H, s); 1.60 (3H, s); 1.58 (3H, s); 0.30 (9H, s) upon treatment with K$_2$CO$_3$ in methanol for 1 h. Dilution of the reaction mixture with ethyl acetate, washing with sat. aq. sodium hydrogen carbonate, extraction of the aqueous layer thrice with ethyl acetate, combining the organic layers, drying over sodium sulfate, filtration and evaporation in vacuo and purification by column chromatography providing Compound No. 38. Compound 37 can be prepared directly from 2-(3-bromoquinolinyl-6-oxy)-2-methylthio-N-(2-methoxyimino-1,1-dimethyl-ethyl)acetamide from Example 3, as described in Example 5, Step 1.

In addition, compound No. 38 (2-(3-ethynyl-quinolin-6-yloxy)-N-(2-methoxyimino-1,1-dimethyl-ethyl)-2-methylsulfanyl-acetamide) may be prepared starting from 3-trimethylsilanylethynyl-quinolin-6-ol [C$_{14}$H$_{15}$NOSi, m/z 241] (prepared from 3-bromo-quinolin-6-ol and trimethylsilylacetylene as described in Example 5, Step 1) and chloromethylsulfanyl-acetic acid methyl ester using similar procedures to those described in Example 1, Stage 1 and 2.

Alternatively, compound No. 38 (2-(3-ethynyl-quinolin-6-yloxy)-N-(2-methoxyimino-1,1-dimethyl-ethyl)-2-methylsulfanyl-acetamide) may be prepared starting from 3-ethynylquinolin-6-ol [C$_{11}$H$_7$NO, m/z 169] (prepared from 3-bromo-quinolin-6-ol and trimethylsilylacetylene as described in Example 5, Steps 1 and 2) and chloro-methyl-sulfanyl-acetic acid methyl ester using similar procedures to those described in Example 1, Stage 1 and 2.

EXAMPLE 6

Example 6 provides characterising NMR data and/or melting points for additional compounds that are in part listed in the Tables cited above and have been prepared using procedures similar to those described in Examples 1-3 unless specified otherwise. Unless stated otherwise, the $^1$H NMR signals reported are those that characterize to the major diastereoisomer.

The following oximes of the general formula (1) were prepared using similar procedures to those described in Example 1, Stage 1 and 2 starting from 3-iodo-8-methyl-quinolin-6-ol and chloro-methylsulfanyl-acetic acid methyl ester:

Compound No. 39: N-(3-Butoxyimino-1,1-dimethyl-propyl)-2-(3-iodo-8-methyl-quinolin-6-yloxy)-2-methylsulfanylacetamide $^1$H NMR (CDCl$_3$) δ ppm: 8.95 (1H, s); 8.44 (1H, s); 7.40 (1H, t, isomer A); 7.32 (1H, s); 6.98 (1H, s); 6.75 (1H, s, isomer B)(—NH); 6.72 (1H, t, isomer B); 6.65 (1H, s, isomer A)(—NH); 5.59 (1H, s, isomer A); 5.55 (1H, s, isomer B); 4.11 (2H, t, isomer B); 4.02 (2H, t, isomer A); 2.83 (2H, t, isomer B); 2.78 (3H, s); 2.65 (2H, d, isomer A); 2.21 (3H, s, isomer B); 2.19 (3H, s, isomer A); 1.73-1.56 (2H, m); 1.47 (6H, s); 1.51-1.30 (2H, m); 0.98-0.85 (3H, m).

Compound No. 40: N-(3-Allyloxyimino-1,1-dimethyl-propyl)-2-(3-iodo-8-methyl-quinolin-6-yloxy)-2-methylsulfanyl-acetamide $^1$H NMR (CDCl$_3$) δ ppm: 8.94 (1H, s); 8.40 (1H, s); 7.42 (1H, t, isomer A); 7.29 (1H, s); 6.76 (1H, t, isomer B); 6.72 (1H, s, isomer B)(—NH); 6.60 (1H, s, isomer A); 6.04-5.88 (1H, m); 5.58 (1H, s, isomer A); 5.54 (1H, s, isomer B); 5.32-5.17 (2H, m); 4.60 (2H, sd, isomer B); 4.50 (2H, s, isomer A); 2.91-2.78 (2H, m); 2.76 (3H, s); 2.67 (2H, d, isomer A); 2.20 (3H, s); 1.47 (3H, s, isomer B); 1.45 (3H, s, isomer A).

Compound No. 41: N-(3-Hydroxyimino-1,1-dimethyl-propyl)-2-(3-iodo-8-methyl-quinolin-6-yloxy)-2-methylsulfanylacetamide $^1$H NMR (CDCl$_3$) δ ppm: 8.99 (1H, s); 8.47 (1H, s); 7.45 (1H, t, isomer A); 7.35 (1H, s); 6.99 (1H, s); 6.96 (1H, s, isomer B)(—NH); 6.84 (1H, t, isomer B); 6.59 (1H, s, isomer A)(—NH); 5.59 (1H, s, isomer A); 5.57 (1H, s, isomer B); 2.87 (2H, t, isomer B); 2.80 (3H, s); 2.70 (2H, d, isomer A); 2.20 (3H, s); 1.53 (6H, s, isomer A); 1.51 (6H, s, isomer B).

Compound No. 42: N-(2-Ethoxyimino-1,1-dimethyl-ethyl)-2-(3-iodo-8-methyl-quinolin-6-yloxy)-2-methylsulfanyl-acetamide $^1$H NMR (CDCl$_3$) δ ppm: 8.94 (1H, d); 8.42 (1H, d); 7.64 (1H, s br); 7.40 (1H, s); 7.31 (1H, d); 6.97 (1H, d); 5.61 (1H, s); 4.13 (2H, q); 2.75 (3H, s); 2.17 (3H, s); 1.60 (3H, s); 1.57 (3H, s); 1.28 (3H, t)

Compound No. 43: N-(3-tert-Butoxyimino-1,1-dimethyl-propyl)-2-(3-iodo-8-methyl-quinolin-6-yloxy)-2-methylsulfanyl-acetamide $^1$H NMR (CDCl$_3$) δ ppm: 8.95 (1H, s); 8.41 (1H, s); 7.38 (1H, t, isomer A); 7.30 (1H, s); 6.97 (1H, s); 6.70 (1H, t, isomer B); 6.59 (1H, s)(—NH); 5.57 (1H, s, isomer A); 5.52 (1H, s, isomer B); 2.88-2.79 (2H, m, isomer B); 2.77 (3H, s); 2.70-2.59 (2H, m, isomer A); 2.21 (3H, s, isomer B); 2.17 (3H, s, isomer A); 1.47 (6H, s); 1.29 (9H, s, isomer B); 1.25 (9H, s, isomer A). mp=130-131° C.

Compound No. 44: 2-(3-Iodo-8-methyl-quinolin-6-yloxy)-N-(2-methoxyimino-1,1-dimethyl-ethyl)-2-methylsulfanyl-acetamide $^1$H NMR (CDCl$_3$) δ ppm: 8.94 (1H, d); 8.42 (1H, d); 7.55 (1H, s br); 7.41 (1H, s); 7.32 (1H, d); 6.98 (1H, d); 5.61 (1H, s); 3.88 (3H, s); 2.76 (3H, s); 2.18 (3H, s); 1.60 (3H, s); 1.57 (3H, s).

Compound No. 45: N-(2-Allyloxyimino-1,1-dimethyl-ethyl)-2-(3-iodo-8-methyl-quinolin-6-yloxy)-2-methylsulfanyl-acetamide $^1$H NMR (CDCl$_3$) δ ppm: 8.95 (1H, d); 8.42 (1H, d); 7.60 (1H, s br); 7.46 (1H, s); 7.31 (1H, d); 6.97 (1H, d); 6.04-5.94 (1H, m); 5.61 (1H, s); 5.33 (1H, dd); 5.23 (1H, dd); 4.57 (2H, d); 2.76 (3H, s); 2.17 (3H, s); 1.62 (3H, s); 1.58 (3H, s).

The following oximes of the general formula (1) were prepared using similar procedures to those described in Example 1, Stage 1 and 2 starting from 3-iodo-quinolin-6-ol and chloro-methylsulfanyl-acetic acid methyl ester:

Compound No. 46: 2-(3-Iodo-quinolin-6-yloxy)-N-(3-methoxyimino-1,1-dimethyl-propyl)-2-methylsulfanyl-acetamide $^1$H NMR (CDCl$_3$) δ ppm: 8.95 (1H, s); 8.47 (1H, s); 8.02 (1H, d); 7.45 (1H, dd); 7.37 (1H, t, isomer A); 7.15 (1H, s);

6.83 (1H, s, isomer)(—NH); 6.74 (1H, t, isomer); 6.60 (1H, s, isomer A)(—NH); 5.58 (1H, s, isomer); 5.54 (1H, s, isomer B); 3.89 (3H, s, isomer B); 3.80 (3H, s, isomer); 2.85-2.68 (2H, m, isomer B); 2.65 (2H, d, isomer A); 2.20 (3H, s, isomer); 2.19 (3H, s, isomer A); 1.43 (6H, s). mp=117-118° C.

Compound No. 47: N-(3-Benzyloxyimino-1,1-dimethyl-propyl)-2-(3-iodo-8-methyl-quinolin-6-yloxy)-2-methylsulfanyl-acetamide $^1$H NMR (CDCl$_3$) d ppm: 8.96 (1H, s); 8.41 (1H, dd); 7.48 (1H, t, isomer A); 7.40-7.26 (6H, m); 6.96 (1H, dd); 6.68 (1H, t, isomer B); 6.70 (1H, s, isomer B)(—NH); 6.60 (1H, s, isomer A)(—NH); 5.57 (1H, s, isomer A); 5.52 (1H, s, isomer B); 5.15 (2H, s, isomer B); 5.08 (2H, s, isomer A); 2.97-2.81 (2H, m, isomer B); 2.75 (3H, s); 2.68 (2H, d, isomer A); 2.19 (3H, s); 1.47 (3H, s, isomer B); 1.44 (3H, s, isomer A).

Compound No. 48: 2-(3-Iodo-quinolin-6-yloxy)-N-(3-methoxyimino-1-methyl-propyl)-2-methylsulfanyl-acetamide $^1$H NMR (CDCl$_3$) δ ppm: 8.95 (1H, s); 8.43 (1H, s); 7.40 (1H, t, isomer B); 7.31 (1H, s); 6.95 (1H, s); 6.75 (1H, t)(—NH); 6.68 (1H, t, isomer A); 5.66 (1H, s, isomer B); 5.62 (1H, s, isomer A); 4.36-4.24 (1H, m); 3.84 (3H, d, isomer B); 3.76 (3H, d, isomer A); 2.76 (3H, s); 2.51-2.34 (2H, m); 2.18 (3H, s, isomer A); 2.2.15 (3H, s, isomer B); 1.31 (3H, s, isomer A); 1.26 (3H, s, isomer B).

Compound No. 49: 2-(3-iodo-quinolin-6-yloxy)-N-{3-[(E & Z)-methoxy-imino]-1,1-dimethyl-butyl}-2-methylsulfanyl-acetamide $^1$H NMR (CDCl$_3$) d ppm: 8.80 (1H, s); 8.24 (1H, s); 8.03 (1H, d); 7.77 (1H, s, isomer B)(—NH); 7.48 (1H, dd); 7.35 (1H, s, isomer A)(—NH); 7.18 (1H, sd); 5.58 (1H, s, isomer A); 5.49 (1H, s, isomer B); 3.87 (3H, s, isomer B); 3.82 (3H, s, isomer A); 2.52-2.42 (2H, m); 2.21 (3H, s, isomer B); 2.18 (3H, s, isomer A); 1.94 (3H, s, isomer B); 1.88 (3H, s, isomer A); 1.49 (6H, s, isomer B); 1.47 (6H, s, isomer A).

Compound No. 50: 2-(3-Iodo-quinolin-6-yloxy)-N-(2-methoxy-imino-1,1-dimethyl-ethyl)-2-methylsulfanyl-acetamide $^1$H NMR (CDCl$_3$) δ ppm: 8.95 (1H, d); 8.47 (1H, d); 8.03 (1H, d); 7.59 (1H, s br); 7.46 (1H, dd); 7.40 (1H, s); 7.15 (1H, d); 5.64 (1H, s); 3.88 (3H, s); 2.20 (3H, s); 1.60 (3H, s); 1.58 (3H, s).

Compound No. 51: N-(2-Ethoxyimino-1,1-dimethyl-ethyl)-2-(3-iodo-quinolin-6-yloxy)-2-methylsulfanyl-acetamide $^1$H NMR (CDCl$_3$) δ ppm: 8.94 (1H, d); 8.46 (1H, d); 8.03 (1H, d); 7.66 (1H, s br); 7.44 (1H, dd); 7.39 (1H, s); 7.14 (1H, d); 5.63 (1H, s); 4.12 (2H, q); 2.19 (3H, s); 1.61 (3H, s); 1.58 (3H, s); 1.28 (3H, t)

Compound No. 52: N-(2-Allyloxyimino-1,1-dimethyl-ethyl)-2-(3-iodo-quinolin-6-yloxy)-2-methyl-sulfanyl-acetamide $^1$H NMR (CDCl$_3$) δ ppm: 8.95 (1H, d); 8.47 (1H, d); 8.02 (1H, d); 7.61 (1H, d); 7.45 (1H, s); 7.45 (1H, dd); 7.14 (1H, d); 6.03-5.94 (1H, m); 5.63 (1H, s); 5.32 (1H, dd); 5.24 (1H, dd); 4.57 (2H, d); 2.19 (3H, s); 1.61 (3H, s); 1.58 (3H, s)

EXAMPLE 7

This Example illustrates the preparation of 2-(3-bromo-quinolin-6-yloxy)-N-(1-cyano-2-methoxyimino-1-methyl-ethyl)-2-methylsulfanyl acetamide (Compound No. 53) according to scheme 15.

Stage 1: Preparation of 2-(3-bromo-quinolin-6-yloxy)-N-(1-cyano-2-hydroxy-1-methyl-ethyl)-2-methylsulfanyl acetamide according to the second step shown in scheme 15

0.86 ml of Triethylamine, 0.672 g of 1-hydroxy-7-azabenzotriazole and 0.946 g of N-(3-dimethylaminopropyl)-N'-ethylcarbodiimide.HCl were added at R.T. to a suspension of 1.35 g of (3-bromo-quinolin-6-yloxy)-methylsulfanyl-acetic acid in 11 ml of dry DMF. To this suspension, 0.494 g of 2-amino-3-hydroxy-2-methyl-propionitrile dissolved in 2 ml of dry DMF were added dropwise. The reaction mixture was stirred 16 hrs at R.T and then poured onto a mixture of ethyl acetate and brine. The two layers were separated and the aqueous layer was extracted thrice with ethyl acetate. The organic layers were combined, washed once with brine and then dried over sodium sulphate. After filtration and concentration under reduced pressure 1.886 g of a crude mixture were isolated as a dark orange oil. The crude mixture was purified by flash chromatography on silica gel (hexane/ethyl acetate) to give 1.103 g of 2-(3-bromo-quinolin-6-yloxy)-N-(1-cyano-2-hydroxy-1-methyl-ethyl)-2-methylsulfanyl acetamide in mixture with 3-(3-bromo-quinolin-6-yl)-2-methylsulfanyl-propionic acid 2-[2-(3-bromo-quinolin-6-yloxy)-2-methylsulfanyl-acetylamino]-2-cyano-2-methyl-ethyl ester resulting from the homo coupling process.

This mixture was dissolved in 19 ml of THF and treated with 2 ml of a solution of NaOH (1N) at 0° C. for 1 hr. The crude mixture was extracted (pH=11) thrice with ethyl acetate. The organic layers were combined, washed once with brine and then, dried over sodium sulphate. After filtration and concentration under reduced pressure the residue was purified by flash chromatography on silica gel (hexane/ethyl acetate) to give 0.669 g of 2-(3-bromo-quinolin-6-yloxy)-N-(1-cyano-2-hydroxy-1-methyl-ethyl)-2-methylsulfanyl acetamide as a yellowish amorphous solid.

$^1$H NMR (CDCl$_3$) δ ppm: 8.82 (1H, m); 8.24 (1H, d); 8.03 (1H, dd); 7.46 (1H, dm); [{7.22 (s br), 7.17 (s br) 1H}, isomer A and isomer B]; 7.22 (1H, m); [{5.74 (s), 5.71 (s) 1H}, isomer A and isomer B]; 4.08-3.82 (2H, m); 3.40 (1H, s br); 2.21 (3H, s); [{1.80 (s), 1.78 (s) 3H}, isomer A and isomer B].

Stage 2: Preparation of 2-(3-bromo-quinolin-6-yloxy)-N-(1-cyano-1-methyl-2-oxo-ethyl)-2-methyl-sulfanyl-acetamide according to the fourth step shown in Scheme 15

2-(3-Bromo-quinolin-6-yloxy)-N-(1-cyano-2-hydroxy-1-methyl-ethyl)-2-methylsulfanyl acetamide (0.660 g) from Stage 1 above in dichloromethane (25 ml) was treated with Dess-Martin periodinane (0.819 g). The reaction mixture was stirred at R.T. for 2 h 30. The reaction mixture was quenched with sat. aqueous NaHCO$_3$ and sat. aqueous sodium thiosulphate. The reaction mixture was vigorously stirred at rt. for 30 minutes after which time the two phases were separated. The organic layer was washed with sat. aqueous. NaHCO$_3$. After separation the organic phase was dried over sodium sulphate, filtered and evaporated to yield 0.397 g of 2-(3-Bromo-quinolin-6-yloxy)-N-(1-cyano-1-methyl-2-oxo-ethyl)-2-methylsulfanyl-acetamide as a crude product which was used in the next step without any further purification.

$^1$H NMR (CDCl$_3$) δ ppm: [{9.51 (s), 9.49 (s) 1H}, isomer A and isomer B]; 8.87 (1H, d); 8.28 (1H, d); 8.07 (1H, d); 7.48 (1H, dd); [{7.44 (s br), 7.39 (s br) 1H}, isomer A and isomer B]; 7.21 (1H, d); 5.81 (1H, s); 2.21 (3H, s); [{1.89 (s), 1.87 (s) 3H}, isomer A and isomer B].

Stage 3: Preparation of 2-(3-bromo-quinolin-6-yloxy)-N-(1-cyano-2-methoxyimino-1-methyl-ethyl)-2-methylsulfanyl acetamide (Compound No. 53) according to the fifth step shown in Scheme 15

2-(3-Bromo-quinolin-6-yloxy)-N-(1-cyano-1-methyl-2-oxo-ethyl)-2-methylsulfanyl-acetamide (0.430 g) obtained as described in Stage 2 above, pyridine (0.178 ml) and O-methyl-hydroxylamine hydrochloride (0.185 g) in dry methanol (10 ml) were stirred at R.T. for 16 hrs. The reaction mixture was diluted with ethyl acetate and poured onto saturated NaHCO$_3$ (50 ml). The two phases were separated and the aqueous layer was extracted thrice with ethyl acetate. The organic layers were combined, dried over sodium sulphate, filtered and evaporated. The residue was co-evaporated with toluene and then, purified by column chromatography (hexane/ethyl acetate 1:1 to 1:2) to give 0.245 g of 2-(3-bromo-quinolin-6-yloxy)-N-(1-cyano-2-methoxyimino-1-methyl-ethyl)-2-methylsulfanyl acetamide (Compound No. 53) as a white solid (m.p.: 138-145° C.).

The following oximes of the general formula (1) were prepared using similar procedures to those described in Example 7, Stages 1 to 3 starting from the corresponding substituted quinolin-6-yloxy)-methylsulfanyl-acetic acids and 2-amino-3-hydroxy-2-methyl-propionitrile.

Compound No. 54: 2-(3-Bromo-8-methyl-quinolin-6-yloxy)-N-(1-cyano-2-methoxyimino-1-methyl-ethyl)-2-methylsulfanyl-acetamide: mp: 156-159° C.

Compound No. 55: N-(1-Cyano-2-methoxyimino-1-methyl-ethyl)-2-(3-iodo-8-methyl-quinolin-6-yloxy)-2-methylsulfanyl-acetamide: mp: 166-168° C.

Compound No. 56: N-(1-Cyano-2-methoxyimino-1-methyl-ethyl)-2-(3-ethynyl-8-methyl-quinolin-6-yloxy)-2-methylsulfanyl-acetamide: mp: 172-174° C.

Compound No. 57: N-(1-Cyano-2-methoxyimino-1-methyl-ethyl)-2-(3-iodo-quinolin-6-yloxy)-2-methyl-sulfanyl-acetamide: mp: 59-64° C.

Compound No. 58: N-(1-Cyano-2-methoxyimino-1-methyl-ethyl)-2-methylsulfanyl-2-(3-trimethylsilanylethynyl-quinolin-6-yloxy)-acetamide: mp: 69-75° C.

Compound No. 59: N-(1-Cyano-2-methoxyimino-1-methyl-ethyl)-2-(3-ethynyl-quinolin-6-yloxy)-2-methylsulfanyl-acetamide: mp: 58-65° C.

The following oximes of the general formula (1) were prepared using similar procedures to those described in Example 7, Stages 1 to 3 starting from the corresponding substituted quinolin-6-yloxy butyric acids and 2-amino-3-hydroxy-2-methyl-propionitrile.

Compound No. 60: 2-(3-Bromo-quinolin-6-yloxy)-N-(1-cyano-2-methoxyimino-1-methyl-ethyl)-butyramide; mp: 152-155° C.

Compound No. 61: N-(1-Cyano-2-methoxyimino-1-methyl-ethyl)-2-(3-ethynyl-quinolin-6-yloxy)-butyramide: mp: 146-148° C.

EXAMPLE 8

This Example illustrates the preparation of 2-(3-Ethynyl-quinolin-6-yloxy)-N-(2-methoxyimino-1-methyl-1-prop-2-ynyloxymethyl-ethyl)-2-methylsulfanyl-acetamide (Compound No. 62) according to Schemes 10 and 11.

Stage 1: Preparation of 3-Methyl-3-prop-2-ynyloxymethyl-1-oxa-4-aza-spiro[4.5]decane Sodium hydride (55% in dispersion in oil) (0.636 g) was added portion wise to a solution of (3-methyl-1-oxa-4-aza-spiro[4.5]dec-3-yl)-methanol (2.0 g) in dry THF (30 ml) at 0° C. The reaction mixture was stirred at R.T. for 50'. Propargyl bromide (0.972 ml) was added dropwise at 0° C. and the resulting mixture was stirred at R.T. for 2 h 30. Additional sodium hydride (55% in dispersion in oil) (0.047 g) and propargyl bromide (0.081 ml) were added at 0° C. followed by the heating of the reaction mixture at 40-45° C. for 1 hr allowed to reach reaction completion. The reaction mixture was treated with abs. Ethanol (4 ml) and diluted with diethyl ether. The resulting insoluble residue was filtered off and the filtrate was concentrated in vacuo to give 2.89 g of crude residue which was purified by column chromatography (hexane/ethyl acetate 1:1) to yield 2.33 g of 3-Methyl-3prop-2-ynyloxymethyl-1-oxa-4-aza-spiro[4.5]decane as an orange liquid.

$^1$H NMR (CDCl$_3$) δ ppm: 4.18 (2H, d); 3.82 (1H, d); 3.53 (1H, d); 3.43 (1H, d); 3.38 (1H, d); 2.42 (1H, t); 1.7-1.2 (10H, m); 1.25 (1H, s).

Stage 2: Preparation of 2-amino-2-methyl-3-prop-2-ynyloxy-propan-1-ol hydrochloric salt 3-Methyl-3prop-2-ynyloxymethyl-1-oxa-4-aza-spiro[4.5]decane (1.83 g) in an aqueous solution of HCl (6N) (2.73 ml) were refluxed for 1 hr. The reaction mixture was cooled down to room temperature, diluted with water and extracted thrice with ethyl ether. The two layers were separated. The aqueous layer was concentrated under reduced pressure and further co-evaporated with toluene to yield 2-amino-2-methyl-3-prop-2-ynyloxy-propan-1-ol hydrochloric salt (1.205 g) as a white beige solid which was used in the next step without any further purification.

$^1$H NMR (DMSO) δ ppm: 8.02 (3H, s br); 5.47 (1H, s br); 4.21 (2H, s); 3.54-3.49 (5H, m); 1.15 (3H, s).

Stage 3: Preparation of 2-(3-ethynyl-quinolin-6-yloxy)-N-(2-hydroxy-1-methyl-1-prop-2-ynyloxymethyl-ethyl)-2-methylsulfanyl-acetamide 1-hydroxy-7-azabenzotriazole (0.717 g), O-(1H benzotriazol-1-yl)-N,N,N',N'-tetramethyluronium tetrafluoroborate (1.692 g) and 2-amino-2-methyl-3-prop-2-ynyloxy-propan-1-ol hydrochloric salt (0.947 g) were added at room temperature to a solution of triethylamine (2.14 ml) and (3-ethynyl-quinolin-6-yloxy)-methylsulfanyl-acetic acid (1.20 g) in 43 ml of dry DMF. The reaction mixture was stirred 16 hrs at R.T and then poured onto a mixture of ethyl acetate and brine. The two layers were separated and the aqueous layer was extracted thrice with ethyl acetate. The organic layers were combined, washed with sat. sodium hydrogeno carbonate (1×), with water (1×), with brine(1×) and then dried over sodium sulphate. After filtration and concentration under reduced pressure 2.01 g of a crude mixture were isolated as a dark orange oil. The crude mixture was purified by flash chromatography on silica gel (hexane/ethyl acetate) to give 1.22 g of 2-(3-ethynyl-quinolin-6-yloxy)-N-(2-hydroxy-1-methyl-1-prop-2-ynyloxymethyl-ethyl)-2-methylsulfanylacetamide in mixture with (3-ethynyl-quinolin-6-yloxy)-methylsulfanyl-acetic acid 2-[2-(3-ethynyl-quinolin-6-yloxy)-2-methylsulfanyl-acetylamino]-2-methyl-3-prop-2-ynyloxy-propyl ester resulting from the homo coupling process. This residue was dissolved in 24 ml of THF/H$_2$O (1/1) and treated with 42 mg of LiOH monohydrate at room temperature for 1 h 45. The crude mixture was extracted pH=11) thrice with ethyl acetate. The organic layers were combined, washed with water (1×) and with brine (1×) and then, dried over sodium sulphate. After filtration and concentration under reduced pressure, crude 2-(3-Ethynyl-quinolin-6-yloxy)-N-(2-hydroxy-1-methyl-1-prop-2-ynyloxymethyl-ethyl)-2-methylsulfanyl-acetamide (0.944 g) was obtained as a yellow oil and used in the next step without any further purification.

$^1$H NMR (CDCl$_3$) δ ppm: 8.88 (1H, d); 8.22 (1H, d); 8.07 (1H, d); 7.49 (1H, dd); 7.39 (1H, br); 7.22 (1H, m); 5.68 (1H, s); 4.22-4.16 (2H, m); 3.90 (1H, s br); 3.81-3.60 (4H, m); 3.30 (1H, s); 2.45 (1H, dt); [{2.22 (s), 2.20 (s) 3H}, isomer A and isomer B]; [{1.40 (s), 1.34 (s) 3H}, isomer A and isomer B].

Stage 4: Preparation of 2-(3-Ethynyl-quinolin-6-yloxy)-N-(1-methyl-2-oxo-1-prop-2-ynyloxymethyl-ethyl)-2-methylsulfanyl-acetamide 2-(3-Ethynyl-quinolin-6-yloxy)-N-(2-hydroxy-1-methyl-1-prop-2-ynyloxymethyl-ethyl)-2-methylsulfanyl-acetamide (1.0 g) from Stage 3 above in dichloromethane (40 ml) was treated with Dess-Martin periodinane (1.277 g). The reaction mixture was stirred at R.T. for 2 h 30 and then, quenched with sat. aqueous NaHCO$_3$ and sat. aqueous sodium thiosulphate. The reaction mixture was vigorously stirred at rt. for 30 minutes after which time the two phases were separated. The organic layer was washed with sat. aqueous. NaHCO$_3$. After separation, the organic phase was dried over sodium sulphate, filtered and evaporated to yield 1.10 g of 2-(3-ethynyl-quinolin-6-yloxy)-N-(1-methyl-2-oxo-1-prop-2-ynyloxymethyl-ethyl)-2-methylsulfanyl acetamide as a crude product (along with minor impurities. The crude mixture was used in the next step without any further purification.

$^1$H NMR (CDCl$_3$) δ ppm: [{9.51 (s), 9.49 (s) 1H}, isomer A and isomer B]; 8.86 (1H, d); 8.22 (1H, d); 8.07 (1H, d); 7.53-7.50 (1H, m); [{7.58 (s br), 7.48 (s br) 1H}, isomer A and isomer B]; 7.26 (1H, m); 5.72 (1H, s); 4.16-3.87 (4H, m); 3.28 (1H, s); 2.48 (1H, m); [{2.22 (s), 2.20 (s) 3H}, isomer A and isomer B]; 1.52 (3H, s).

Stage 5: Preparation of 2-(3-Ethynyl-quinolin-6-yloxy)-N-(2-methoxyimino-1-methyl-1-prop-2-ynyloxymethyl-ethyl)-2-methylsulfanyl acetamide Crude 2-(3-ethynyl-quinolin-6-yloxy)-N-(1-methyl-2-oxo-1-prop-2-ynyloxymethyl-ethyl)-2-methylsulfanyl acetamide (0.995 g) obtained as described in Stage 4 above, pyridine (0.40 ml) and O-methyl-hydroxylamine hydrochloride (0.419 g) in dry methanol (60 ml) were stirred at R.T. for 18 hrs. The reaction mixture was diluted with ethyl acetate and poured onto saturated NaHCO$_3$ (60 ml). The two phases were separated and the aqueous layer was extracted thrice with ethyl acetate. The organic layers were combined, dried over sodium sulphate, filtered and evaporated. The residue was co-evaporated with toluene and then, purified by flash chromatography (hexane/ethyl acetate 3:2 to 1:1) to give 0.81 g of 2-(3-ethynyl-quinolin-6-yloxy)-N-(2-methoxyimino-1-methyl-1-prop-2-ynyloxymethyl-ethyl)-2-methylsulfanyl acetamide as a colorless oil.

Compound No. 62: $^1$H NMR (CDCl$_3$) δ ppm: 8.86 (1H, d); 8.21 (1H, d); 8.05 (1H, d); [{7.68 (s br), 7.59 (s br) 1H}, isomer A and isomer B]; 7.44-7.49 (2H, m); 7.21 (1H, d); 5.65 (1H, s); 4.12-4.19 (2H, m); 3.73-4.0 (2H, m); [{3.90 (s), 3.88 (s), 3H}, isomer A and isomer B]; 3.29 (1H, s); 2.43 (1H, s); 2.20 (3H, s); [{1.55 (s), 1.53 (s), 3H}, isomer A and isomer B]

The following oximes of the general formula (1) were prepared using similar procedures to those described in Example 8, Stages 3 to 5 starting from (3-bromo-8-methyl-quinolin-6-yloxy)-methylsulfanyl-acetic acid and 2-amino-3-methoxy-2-methyl-propan-1-ol hydrochloride:

Compound No. 63: 2-(3-Bromo-8-methyl-quinolin-6-yloxy)-N-(2-methoxyimino-1-methoxymethyl-1-methyl-ethyl)-2-methylsulfanyl-acetamide $^1$H NMR (CDCl$_3$) δ ppm: 8.82 (1H, d); 8.21 (1H, d); [{7.68 (s, br), 7.58 (s, br) 1H}, isomer A and isomer B]; [{7.50 (s), 7.45 (s) 1H}, isomer A and isomer B]; 7.33 (1H, d); 7.03 (1H, d); 5.66 (1H, s); 3.90 (3H, s); 3.60-3.90 (2H, m); [{3.38 (s), 3.36 (s) 3H}, isomer A and isomer B]; 2.78 (3H, s); 2.22 (3H, s); [{1.59 (s), 1.58 (s) 3H}, isomer A and isomer B]. MP 102-103° C.

The following oxime of the general formula (1) were prepared using similar procedures to those described in Example 7, Stages 3 to 5 starting from (3-bromo-quinolin-6-yloxy)-methylsulfanyl-acetic acid and 2-amino-3-methoxy-2-methyl-propan-1-ol hydrochloride:

Compound No. 64: 2-(3-Bromo-quinolin-6-yloxy)-N-[2-methoxy-1-(methoxyimino-methyl)-1-methyl-ethyl]-2-methylsulfanyl-acetamide 1H NMR (CDCl3) d ppm: 8.74 (1H, d); 8.17 (1H, d); 7.98 (1H, d); [{7.61 (s, br), 7.52 (s, br) 1H}, isomer A and isomer B]; [{7.36 (s), 7.40 (s) 1H}, isomer A and isomer B]; 7.38 (1H, m); 7.12 (1H, s, br); 5.58 (1H, s), [{3.81 (s), 3.81 (s) 3H}, isomer A and isomer B]; 3.50-3.81 (2H, m); [{3.29 (s), 3.27 (s) 3H}, isomer A and isomer B]; 2.13 (3H, s); [{1.50 (s), 1.49 (s) 3H}, isomer A and isomer B].

The following oxime of the general formula (1) were prepared using similar procedures to those described in Example 7, Stages 3 to 5 starting from (3-ethynyl-quinolin-6-yloxy)-methylsulfanyl-acetic acid and 2-amino-3-methoxy-2-methyl-propan-1-ol hydrochloride:

Compound No. 65: 2-(3-Ethynyl-quinolin-6-yloxy)-N-(2-methoxyimino-1-methoxymethyl-1-methyl-ethyl)-2-methylsulfanyl-acetamide $^1$H NMR (CDCl$_3$) δ ppm: 8.86 (1H, d); 8.22 (1H, d); 8.06 (1H, d); [{7.70 (s, br), 7.61 (s, br) 1H}, isomer A and isomer B]; [{7.45 (s), 7.49 (s) 1H}, isomer A and isomer B]; 7.48 (1H, m); 7.24 (1H, s, br); 5.68 (1H, s), 3.90 (s, 3H}; 3.59-3.90 (2H, m); [{3.38 (s), 3.35 (s) 3H}, isomer A and isomer B]; 3.31 (1H, s); 2.22 (3H, s); [{1.59 (s), 1.58 (s) 3H}, isomer A and isomer B].

The following oxime of the general formula (1) were prepared using similar procedures to those described in Example 7, Stages 3 to 5 starting from (3-ethynyl-8-methyl-quinolin-6-yloxy)-methylsulfanyl-acetic acid and 2-amino-3-methoxy-2-methyl-propan-1-ol hydrochloride:

Compound No. 66: 2-(3-Ethynyl-8-methyl-quinolin-6-yloxy)-N-(2-methoxy-imino-1-methoxymethyl-1-methyl-ethyl)-2-methylsulfanyl-acetamide $^1$H NMR (CDCl$_3$) δ ppm: 8.83 (1H, d); 8.15 (1H, d); [{7.68 (s, br), 7.58 (s, br) 1H}, isomer A and isomer B]; [{7.68 (s, br), 7.58 (s, br) 1H}, isomer A and isomer B]; [{7.46 (s), 7.41 (s) 1H}, isomer A and isomer B]; 7.31 (1H, s, br); 7.04 (1H, s, br); 5.64 (1H, s), 3.87 (s, 3H}; 3.56-3.87 (2H, m); [{3.35 (s), 3.32 (s) 3H}, isomer A and isomer B]; 3.27 (1H, s); 2.76 (3H, s); 2.18 (3H, s); [{1.56 (s), 1.54 (s) 3H}, isomer A and isomer B].

The following oxime of the general formula (1) were prepared using similar procedures to those described in Example 7, Stages 3 to 5 starting from (3-iodo-quinolin-6-yloxy)-methylsulfanyl-acetic acid and 2-amino-3-methoxy-2-methyl-propan-1-ol hydrochloride:

Compound No. 67: 2-(3-Iodo-quinolin-6-yloxy)-N-[2-methoxy-1-(methoxyimino-methyl)-1-methyl-ethyl]-2-methylsulfanyl-acetamide 1H NMR (CDCl3) d ppm: 8.92 (1H, d); 8.44 (1H, s); 8.01 (1H, d); [{7.68 (s, br), 7.59 (s, br) 1H}, isomer A and isomer B]; [{7.46 (s), 7.41 (s) 1H}, isomer A and isomer B]; 7.43, (1H, m); 7.13 (1H, s, br); 5.64 (1H, s); 3.87 (s, 3H}; 3.55-3.87 (2H, m); [{3.35 (s), 3.32 (s) 3H}, isomer A and isomer B]; 2.18 (s, 3H); [{1.56 (s), 1.54 (s) 3H}, isomer A and isomer B].

The following oxime of the general formula (1) were prepared using similar procedures to those described in Example 7, Stages 3 to 5 starting from 2-(3-iodo-quinolin-6-yloxy)-butyric acid and 2-amino-3-methoxy-2-methyl-propan-1-ol hydrochloride:

Compound No. 68: 2-(3-Iodo-quinolin-6-yloxy)-N-(2-methoxyimino-1-methoxymethyl-1-methyl-ethyl]-butyramide $^1$H NMR (CDCl$_3$) δ ppm: 8.88 (1H, d); 8.38 (1H, d); 7.95 (1H, d); 7.22-7.42 (3H, m); 6.95 (1H, s, br); 4.56 (1H, s, br); [{3.76 (d), 3.74 (d) 3H}, isomer A and isomer B]; 3.49-3.67 (2H, m); [{3.26 (s), 3.20 (s) 3H}, isomer A and isomer B]; 1.98-2.07 (2H, m); [{1.44 (s), 1.42 (s) 3H}, isomer A and isomer B]; 1.06, (3H, t).

EXAMPLE 9

This Example illustrates the preparation of 2-(3-Ethynyl-quinolin-6-yloxy)-N-[1-(methoxyimino-methyl)-1-methyl-prop-2-ynyl]-2-methylsulfanyl-acetamide (Compound No. 69) according to Scheme 13 (Steps 1-6 of Scheme 13 equivalent to Stages 2-7 below).

Stage 1: Preparation of 2-Amino-3-(tert-butyl-diphenyl-silanyloxy)-2-methyl-propan-1-ol Sodium hydride (55% in dispersion in oil) (1.141 g) was added portion wise to a solution of 2-Amino-2-methyl-propane-1,3-diol (2.50 g) in dry THF (35 ml) at 0° C. The reaction mixture was stirred at R.T. for 55'. tert-Butyldiphenylsilyl chloride (6.54 g) in dry THF (10 ml) were added dropwise at 0° C. and the reaction mixture was stirred for 17 hrs at R.T. The reaction mixture was quenched with water (18 ml) and then, extracted thrice with ethyl ether. The two layers were separated. The organic layer was washed once with water and then, dried over sodium sulphate, filtered and concentrated under reduced pressure to yield 8.94 g of 2-Amino-3-(tert-butyl-diphenyl-silanyloxy)-2-methyl-propan-1-ol as a crude product (containing minor impurities) which was used in the next step without any further purification.

$^1$H NMR (CDCl$_3$) δ ppm: 7.68-7.62 (4H, m); 7.47-7.37 (6H); 3.52 (2H, dd); 3.39 (2H, dd); 1.09 (9H, s); 1.02 (3H, s).

Stage 2: Preparation of N-[1-(tert-Butyl-diphenyl-silanyloxymethyl)-2-hydroxy-1-methyl-ethyl]-2-(3-ethynyl-quinolin-6-yloxy)-2-methylsulfanyl-acetamide To a solution of (3-Ethynyl-quinolin-6-yloxy)-methylsulfanyl-acetic acid (1.525 g) and Triethylamine (2.72 ml) in dry acetonitrile (15 ml) at R.T. were added successively a solution of 1-hydroxy-7-azabenzotriazole (0.911 g) and 0-(1H Benzotriazol-1-yl)-N,N,N',N'-tetramethyluronium tetrafluoroborate (2.15 g) in dry acetonitrile (15 ml) and a solution of crude 2-Amino-3-(tert-butyl-diphenyl-silanyloxy)-2-methyl-propan-1-ol (2.30 g) in dry acetonitrile (23 ml). The reaction mixture was stirred at R.T. for 16 hrs and then, poured onto a mixture of sat. NaHCO$_3$, ethyl acetate and brine. The two layers were separated and the aqueous layer was extracted thrice with ethyl acetate. The organic layers were combined, washed with sat. NaHCO$_3$ (1×) and with brine(1×) and then, dried over sodium sulphate. After filtration and concentration under reduced pressure 4.69 g of a crude mixture were isolated as a dark orange oil. The crude mixture was purified by flash chromatography on silica gel (hexane/ethyl acetate) to give 2.07 g of N-[1-(tert-Butyl-diphenyl-silanyloxymethyl)-2-hydroxy-1-methyl-ethyl]-2-(3-ethynyl-quinolin-6-yloxy)-2-methylsulfanyl-acetamide in mixture with (3-Ethynyl-quinolin-6-yloxy)-methylsulfanyl-acetic acid 3-(tert-butyl-diphenyl-silanyloxy)-2-[2-(3-ethynyl-quinolin-6-yloxy)-2-methylsulfanyl-acetylamino]-2-methyl-propyl ester resulting from the homo coupling process. This residue was dissolved in 40 ml of THF/H$_2$O (1/1) and treated with 56 mg of LiOH monohydrate at R.T. for 1 h 20. The reaction mixture was further stirred in the presence of additional LiOH monohydrate till full consumption of the homo coupling product. The crude mixture was extracted (pH=11) thrice with ethyl acetate. The organic layers were combined, washed with water (1×) and with brine (1×) and then, dried over sodium sulphate. After filtration and concentration under reduced pressure, crude N-[1-(tert-Butyl-diphenyl-silanyloxymethyl)-2-hydroxy-1-methyl-ethyl]-2-(3-ethynyl-quinolin-6-yloxy)-2-methylsulfanyl-acetamide (1.94 g) was obtained as a yellow oil and used in the next step without any further purification.

$^1$H NMR (CDCl$_3$) δ ppm: 8.88 (1H, d); 8.19-8.16 (1H, m), 8.00 (1H, t); 7.66-7.52 (5H, m); 7.48-7.26 (7H, m); 7.21-7.18 (1H, m); [{5.69 (s), 5.66 (s) 1H}, isomer A and isomer B]; 4.32-4.11 (1H, dm); 3.78-3.52 (4H, m); 3.30 (1H, s); [{2.21 (s), 2.19 (s) 3H}, isomer A and isomer B]; [{1.49 (s), 1.34 (s) 3H}, isomer A and isomer B]; [{1.11 (s), 1.08 (s) 9H}, isomer A and isomer B].

Stage 3: Preparation of N-[1-(tert-Butyl-diphenyl-silanyloxymethyl)-1-methyl-2-oxo-ethyl]-2-(3-ethynyl-quinolin-6-yloxy)-2-methylsulfanyl-acetamide N-[1-(tert-Butyl-diphenyl-silanyloxymethyl)-2-hydroxy-1-methyl-ethyl]-2-(3-ethynyl-quinolin-6-yloxy)-2-methylsulfanyl-acetamide (1.90 g) from Stage 2 above in dichloromethane (55 ml) was treated with Dess-Martin periodinane (1.615 g). The reaction mixture was stirred at R.T. for 1 h 30 and then, quenched with sat. aqueous $NaHCO_3$ and sat. aqueous sodium thiosulphate. The reaction mixture was vigorously stirred at rt. for 50 minutes after which time the two phases were separated. The organic layer was washed thrice with sat. aqueous. $NaHCO_3$. After separation, the organic phase was dried over sodium sulphate, filtered and evaporated to yield 1.694 g of N-[1-(tert-Butyl-diphenyl-silanyloxymethyl)-1-methyl-2-oxo-ethyl]-2-(3-ethynyl-quinolin-6-yloxy)-2-methylsulfanyl-acetamide as a crude product along with minor impurities. The crude mixture was used in the next step without any further purification.

$^1$H NMR ($CDCl_3$) δ ppm: [{9.51 (s), 9.49 (s) 1H}, isomer A and isomer B]; 8.88 (1H, d); 8.19 (1H, d); 8.02 (1H, d); 7.66-7.54 (5H, m); 7.48-7.30 (7H, m); 7.26-7.21 (1H, dd); [{5.70 (s), 5.66 (s) 1H}, isomer A and isomer B]; 4.01-3.88 (2H, m); 3.30 (1H, s); [{2.22 (s), 2.20 (s) 3H}, isomer A and isomer B]; [{1.50 (s), 1.48 (s) 3H}, isomer A and isomer B]; [{1.02 (s), 0.99 (s) 9H}, isomer A and isomer B].

Stage 4: Preparation of N-[1-(tert-Butyl-diphenyl-silanyloxymethyl)-1-methyl-prop-2-ynyl]-2-(3-ethynyl-quinolin-6-yloxy)-2-methylsulfanyl-acetamide A solution of dimethyl-1-diazo-2-oxopropylphosphonate (0.86 g) in dry methanol (20 ml) was added at R.T. to a solution of crude N-[1-(tert-Butyl-diphenyl-silanyloxymethyl)-1-methyl-2-oxo-ethyl]-2-(3-ethynyl-quinolin-6-yloxy)-2-methylsulfanyl-acetamide in dry methanol (40 ml). The reaction medium was cooled down to 0° C. and Potassium carbonate (0.773 g) was added portion wise along with additional dry methanol (10 ml). The reaction mixture was allowed to warm up to R.T., further stirred for 16 hrs and then poured onto a mixture of ethyl acetate and brine. The two layers were separated and the aqueous layer was extracted thrice with ethyl acetate. The organic layers were combined, washed once with brine and then dried over sodium sulphate. After filtration and concentration under reduced pressure 1.84 g of crude mixture were isolated as a dark orange oil. The residue was purified by flash chromatography on silica gel (hexane/ethyl acetate) to give 1.523 g of N-[1-(tert-butyl-diphenyl-silanyloxymethyl)-1-methyl-prop-2-ynyl]-2-(3-ethynyl-quinolin-6-yloxy)-2-methylsulfanyl-acetamide as a yellow oil.

$^1$H NMR ($CDCl_3$) δ ppm: 8.88 (1H, d); 8.19 (1H, d); 8.01 (1H, dd); 7.70-7.62 (4H, m); 7.46-7.30 (8H, m); 7.21-7.19, (1H, m); [{5.69 (s), 5.66 (s) 1H}, isomer A and isomer B]; 3.93-3.72 (2H, dm); 3.30 (1H, s); 2.39 (1H, d); [{2.23 (s), 2.21 (s) 3H}, isomer A and isomer B]; 1.71 (3H, d); [{1.10 (s), 1.08 (s) 9H}, isomer A and isomer B].

Stage 5: Preparation of 2-(3-Ethynyl-quinolin-6-yloxy)-N-(1-hydroxymethyl-1-methylprop-2-ynyl)-2-methylsulfanyl-acetamide A solution of tetrabutylammonium fluoride (1 M) in THF was added dropwise to a solution of N-[1-(tert-butyl-diphenyl-silanyloxymethyl)-1-methyl-prop-2-ynyl]-2-(3-ethynyl-quinolin-6-yloxy)-2-methylsulfanyl-acetamide (1.49 g) at 0° C. The reaction mixture was allowed to warm up to room temperature, further stirred for 1 h 20 and then, poured onto a mixture of ethyl acetate and brine. The two layers were separated and the aqueous layer was extracted thrice with ethyl acetate. The organic layers were combined, washed once with brine and then dried over sodium sulphate. After filtration and concentration under reduced pressure 2.47 g of crude mixture were isolated as a yellow oil. The residue was purified by flash chromatography on silica gel (hexane/ethyl acetate) to give 0.646 g of 2-(3-Ethynyl-quinolin-6-yloxy)-N-(1-hydroxymethyl-1-methylprop-2-ynyl)-2-methylsulfanyl acetamide as a white solid (m.p.=150-150° C.).

Stage 6: Preparation of 2-(3-ethynyl-quinolin-6-yloxy)-N-(1-formyl-1-methyl-prop-2-ynyl)-2-methylsulfanyl acetamide 2-(3-Ethynyl-quinolin-6-yloxy)-N-(1-hydroxymethyl-1-methylprop-2-ynyl)-2-methylsulfanyl acetamide (0.513 g) in dichloromethane (25 ml) was treated with Dess-Martin periodinane (0.737 g). The reaction mixture was stirred at room temperature for 2 hrs and then, quenched with sat. aqueous $NaHCO_3$ and sat. aqueous sodium thiosulphate. The reaction mixture was vigorously stirred at rt. for 40 minutes after which time the two phases were separated. The organic layer was washed thrice with sat. aqueous. $NaHCO_3$. After separation, the organic phase was dried over sodium sulphate, filtered and evaporated to yield 0.523 g of 2-(3-Ethynyl-quinolin-6-yloxy)-N-(1-formyl-1-methyl-prop-2-ynyl)-2-methylsulfanyl acetamide as a crude product along with minor impurities. The crude mixture was used in the next step without any further purification.

$^1$H NMR ($CDCl_3$) δ ppm: 9.40 (1H, s); 8.86 (1H, d); 8.22 (1H, d); 8.07 (1H, d); 7.52-7.49 (1H, m); [{7.49 (s br), 7.44 (s br) 1H}, isomer A and isomer B]; 7.26 (1H, m); [{5.74 (s), 5.72 (s) 1H}, isomer A and isomer B]; 3.29 (1H, s); 2.54 (1H, s); [{2.23 (s), 2.21 (s) 3H}, isomer A and isomer B]; 1.79 (3H, s).

Stage 7: Preparation of 2-(3-Ethynyl-quinolin-6-yloxy)-N-[1-(methoxyimino-methyl)-1-methyl-prop-2-ynyl]-2-methylsulfanyl-acetamide Crude 2-(3-ethynyl-quinolin-6-yloxy)-N-(1-formyl-1-methyl-prop-2-ynyl)-2-methylsulfanyl acetamide (0.125 g) obtained as described in Stage 6 above, pyridine (0.034 ml) and O-methyl hydroxylamine hydrochloride (0.036 g) in dry methanol (6 ml) were stirred at R.T. for 6 hrs. The reaction mixture was diluted with ethyl acetate and poured onto saturated $NaHCO_3$. The two phases were separated and the aqueous layer was extracted thrice with ethyl acetate. The organic layers were combined, dried over sodium sulphate, filtered and evaporated. The residue was co-evaporated with toluene and then, purified by flash chromatography (hexane/ethyl acetate 4:3 to 1:1) to give 0.106 g of 2-(3-ethynyl-quinolin-6-yloxy)-N-[1-(methoxyimino-methyl)-1-methyl-prop-2-ynyl]-2-methylsulfanyl-acetamide as a colorless oil.

(Compound No. 69) $^1$H NMR ($CDCl_3$) δ ppm: 8.84 (1H, d); 8.22 (1H, d); 8.06 (1H, d); [{7.88 (s br), 7.80 (s br) 1H}, isomer A and isomer B]; 7.50 (1H, s), 7.45 (1H, dd); 7.21-7.24 (1H, m); [{5.72 (s), 5.70 (s) 1H}, isomer A and isomer B]; [{3.95 (s), 3.92 (s) 3H}, isomer A and isomer B]; 3.29 (1H, s); 2.54 (1H, d); 2.21 (3H, s); [{1.90 (s), 1.87 (s) 3H}, isomer A and isomer B].

EXAMPLE 10

Example 10 provides further characterising NMR data and/or melting points for compounds that are in part listed in the Tables cited above and have been prepared using procedures similar to those described in Examples 1-9 unless specified otherwise. The $^1$H NMR signals reported are those that characterize the major diasteroisomer, unless otherwise stated.

Thus, the following quinolin-6-yloxy-methoxy-acetic acid-derived oximes of the general formula (1) were prepared using procedures similar to those described for the corresponding quinolin-6-yloxy-methylsulfanyl-acetic acid derivatives described in Examples 1 and/or 3.

Compound No. 70: 2-(3-Bromo-quinolin-6-yloxy)-2-methoxy-N-(2-methoxyimino-1,1-dimethyl-ethyl)-acetamide $^1$H NMR (CDCl$_3$) δ ppm: 8.80 (1H, d); 8.22 (1H, d); 8.02 (1H, d); 7.51 (1H, dd); 7.48 (1H, br); 7.40 (1H, s); 7.38 (1H, d); 5.43 (1H, s); 3.88 (3H, s); 3.52 (3H, s); 1.57 (3H, s); 1.54 (3H, s).

Compound No. 71: 2-(3-Bromo-8-methyl-quinolin-6-yloxy)-2-methoxy-N-(2-methoxyimino-1,1-dimethyl-ethyl)-acetamide: mp: 130-132° C.

Compound No. 72: 2-(3-Iodo-quinolin-6-yloxy)-2-methoxy-N-(2-methoxyimino-1,1-dimethyl-ethyl)-acetamide: mp: 101-103° C.

Compound No. 73: 2-(3-Iodo-8-methyl-quinolin-6-yloxy)-2-methoxy-N-(2-methoxyimino-1,1-dimethyl-ethyl)-acetamide: mp: 126-128° C.

Compound No. 74: 2-Methoxy-N-(2-methoxyimino-1,1-dimethyl-ethyl)-2-(3-trimethylsilanylethynyl-quinolin-6-yloxy)-acetamide $^1$H NMR (CDCl$_3$) δ ppm: 8.81 (1H, d); 8.18 (1H, d); 8.03 (1H, d); 7.49-7.51 (2H, m); 7.40 (1H, s); 7.38-7.41 (1H, m); 5.43 (1H, s); 3.88 (3H, s); 3.52 (3H, s); 1.52 (3H, s); 1.42 (3H, s); 0.30 (9H, s).

Compound No. 75: 2-Methoxy-N-(2-methoxyimino-1,1-dimethyl-ethyl)-2-(8-methyl-3-trimethylsilanylethynyl-quinolin-6-yloxy)-acetamide $^1$H NMR (CDCl$_3$) δ ppm: 8.31 (1H, d); 8.12 (1H, d); 7.48 (1H, s br); 7.40 (1H, s); 7.34-7.37 (1H, m); 7.21 (1H, d); 5.43 (1H, s); 3.88 (3H, s); 3.52 (3H, s); 2.57 (3H, s); 1.57 (3H, s); 1.52 (3H, s); 0.30 (9H, s).

Compound No. 76: 2-(3-Ethynyl-quinolin-6-yloxy)-2-methoxy-N-(2-methoxyimino-1,1-dimethyl-ethyl)-acetamide $^1$H NMR (CDCl$_3$) δ ppm: 8.82 (1H, d); 8.18 (1H, d); 8.03 (1H, d); 7.51-7.53 (2H, m); 7.42 (1H, d); 7.40 (1H, s); 5.43 (1H, s); 3.88 (3H, s); 3.52 (3H, s); 3.28 (1H, s); 1.57 (3H, s); 1.52 (3H, s).

Compound No. 77: 2-(3-Ethynyl-8-methyl-quinolin-6-yloxy)-2-methoxy-N-(2-methoxyimino-1,1-dimethyl-ethyl)-acetamide: mp: 138-140° C.

EXAMPLE 11

This Example illustrates the preparation of 2-(3-ethynyl-quinolin-6-yloxy)-N-[1-(methoxyimino-methyl)-cyclobutyl]-2-methylsulfanyl-acetamide (Compound No. 78):

Stage 1: Preparation of 2-(3-ethynyl-quinolin-6-yloxy)-N-(1-hydroxymethyl-cyclobutyl)-2-methylsulfanyl-acetamide To a solution of (3-ethynyl-quinolin-6-yloxy)-methylsulfanyl-acetic acid (1.10 g) in CH$_3$CN (40 ml) was added Et$_3$N (2.25 ml), AHOBT (0.06 g), TBTU (1.50 g) and (1-amino-cyclobutyl)-methanol (0.06 g) at room temperature, under nitrogen atmosphere. The mixture was stirred at the same temperature during 1 hour, then poured into sat aq NH$_4$Cl and extracted with ethyl acetate (2×20 ml). The organic phase was separated and washed with aq Na$_2$S$_2$O$_3$ and sat. aq. NaCl then dried over anhydrous sodium sulphate, filtered and evaporated under vacuum. Purification by flash chromatography (ethyl acetate/cyclohexane, 2/1) gave 2-(3-ethynyl-quinolin-6-yloxy)-N-(1-hydroxymethyl-cyclobutyl)-2-methylsulfanyl-acetamide (0.70 g) as a yellow oil.

$^1$H NMR (CDCl$_3$) δ ppm: 8.80 (1H, d); 8.15 (1H, d); 8.00 (1H, d); 7.41 (1H, dd); 7.18 (1H, d); 7.04 (1H, s broad); 5.63 (1H, s); 3.83 (2H, s); 3.28 (1H, s); 2.27-2.21 (2H, m); 2.18 (2H, m), 1.99-1.79 (2H, m).

Stage 2: Preparation of 2-(3-Ethynyl-quinolin-6-yloxy)-N-(1-formyl-cyclobutyl)-2-methylsulfanyl-acetamide To a solution of 2-(3-Ethynyl-quinolin-6-yloxy)-N-(1-hydroxymethyl-cyclobutyl)-2-methylsulfanyl-acetamide (310 mg) in CH$_2$Cl$_2$ (30 ml) was added solid Dess Martin periodinane (480 mg) at room temperature, under nitrogen atmosphere. The mixture was stirred at the same temperature during 1 hour, then poured into sat aq NaHCO$_3$ and extracted with CH$_2$Cl$_2$ (2×15 ml). The organic phase was separated and washed with aq Na$_2$S$_2$O$_3$ and sat. aq. NaCl then dried over anhydrous sodium sulphate, filtered and evaporated under vacuum. The crude compound (250 mg) as yellow oil, was used for the next step without purification.

$^1$H NMR (CDCl$_3$) δ ppm: 9.69 (1H, s); 8.84 (1H, d); 8.20 (1H, d); 8.05 (1H, d); 7.47 (1H, dd); 7.42 (1H, s broad); 7.26 (1H, d); 5.72 (1H, s); 3.29 (1H, s); 2.73-2.64 (2H, m); 2.57-2.49 (2H, m); 2.20 (3H, s); 2.16-1.97 (2H, m).

Stage 3. Preparation of Compound No.: 2-(3-Ethynyl-quinolin-6-yloxy)-N-[1-(methoxyimino-methyl)-cyclobutyl]-2-methylsulfanyl-acetamide To a solution of 2-(3-Ethynyl-quinolin-6-yloxy)-N-(1-formyl-cyclobutyl)-2-methylsulfanyl-acetamide (125 mg) in ethanol (10 ml) was added sodium acetate (50 mg) and O-methyl hydroxylamine hydrochloride (44 mg), at room temperature. The mixture was heated to 65° C. during 1 hour. After cooling to room temperature the mixture was poured into water and extracted with ethyl acetate (2×10 ml). The organic phase was washed with sat. aq NaCl solution, dried over anhydrous sodium sulphate, filtered and evaporated under vacuum. Purification by flash chromatography (ethyl acetate/cyclohexane, 1/1) gave 2-(3-ethynyl-quinolin-6-yloxy)-N-[1-(methoxyimino-methyl)-cyclobutyl]-2-methylsulfanyl-acetamide (110 mg) as a yellow oil.

Compound No. 78: $^1$H NMR (CDCl$_3$) δ ppm: 8.84 (1H, d); 8.20 (1H, d); 8.05 (1H, d); 7.70 (1H, s); 7.45 (1H, dd); 7.34 (1H, s broad); 7.22 (1H, d); 5.66 (1H, s); 3.85 (3H, s); 3.28 (1H, s); 2.79-2.71 (2H, m); 2.45-2.35 (2H, m); 2.20 (3H, s); 2.06-1.86 (2H, m)

The following N-(1-formyl-cyclobutyl)-2-(3-iodo-quinolin-6-yloxy)-2-methylsulfanyl-acetamide derived oximes of the general formula (1) were prepared using similar procedure to that described in Example 11, Stage 3 starting from the corresponding substituted quinolinyl acetamides:

Compound No. 79: 2-(3-Iodo-quinolin-6-yloxy)-N-[1-(methoxyimino-methyl)-cyclobutyl]-2-methylsulfanyl-acetamide $^1$H NMR (CDCl$_3$) δ ppm: 8.92 (1H, d); 8.45 (1H, d); 8.00 (1H, d); 7.69 (1H, s); 7.43 (1H, dd); 7.35 (1H, s broad); 7.14 (1H, d); 5.65 (1H, s); 3.84 (3H, s); 2.78-2.70 (2H, m); 2.44-2.35 (2H, m); 2.19 (3H, s); 2.05-1.80 (2H, m). Mp: 140-149° C.

Compound No. 80: 2-(3-Ethynyl-quinolin-6-yloxy)-N-[1-(hydroxyimino-methyl)-cyclobutyl]-2-methylsulfanyl-acetamide $^1$H NMR (CDCl$_3$) δ ppm: 9.73 (1H, s broad); 8.79 (1H, d); 8.17 (1H, d); 7.99 (1H, d); 7.80 (1H, s); 7.53 (1H, s broad); 7.33 (1H, dd); 7.18 (1H, d); 5.65 (1H, s); 3.28 (1H, s); 2.93-2.81 (2H, m); 2.44-2.30 (2H, m); 2.15 (3H, s); 2.10-1.83 (2H, m). Mp: 165-166°.

EXAMPLE 12

This Example illustrates the preparation of 2-(4-chloro-benzo[b]thiophen-6-yloxy)-N-(2-methoxyimino-1,1-dimethyl-ethyl)-2-methylsulfanyl-acetamide (Compound No. 81):

Stage 1: Preparation of 4-chloro-benzo[b]thiophen-6-ol

Step 1: Dimethyl-thiocarbamic acid O-(3-chloro-5-methoxy-phenyl) ester (10.4 g, 0.042 mol) was suspended in KOH (11.8 g, 0.21 mol) in 80 mL of EtOH/Water (3:1) and the reaction mixture was heated to reflux for 2 h. The reaction was then cooled and concentrated to about 50 mL, diluted with EtOAc and the mixture was pored into ice cold HCl. The organic layer was then separated and washed with water, brine, dried and concentrated in vacuo to afford 8 g 3-chloro-5-methoxy-benzenethiol, MS m/z 174 (M$^+$), that was used as such in Step 2.

Step 2: 3-chloro-5-methoxy-benzenethiol from step 1

(8 g, 0.045 mol) was dissolved under stirring in a solution of sodium ethoxide in ethanol (prepared from 2 g of Na and 50 mL of absolute ethanol). Bromoacetaldehyde diethyl acetal (9 g, 0.045 mol) was then added and the mixture was refluxed for 2 h. Most of the ethanol was removed and the residue was diluted with water and extracted in ethyl acetate. The organic layer was washed with water, brine, dried and concentrated in vacuo to afford 10 g of, MS m/z 290 (M$^+$), which was used as such in step 3.

Step 3: A solution of 1-chloro-3-(2,2-diethoxy-ethylsulfanyl)-5-methoxy-benzene from step 5

(5 g, 0.017 mol) in dichloromethane (100 mL) was added dropwise to a solution of BF$_3$.Et$_2$O (2.2 mL, 0.017 mol) in dry dichloromethane (200 mL) at room temperature under nitrogen. The reaction was then stirred at RT for 2 h and quenched with aqueous NaHCO$_3$ solution. The organic layer was separated and the aqueous layer was extracted with dichloromethane. The combined organic extract was washed with water, brine, dried and concentrated. The residue was purified by flash chromatography (silica gel: hexane) to afford 4-chloro-6-methoxy-benzo[b]thiophene, MS m/z 198 (M$^+$).

Step 4: The deprotection of 4-chloro-6-methoxy-benzo[b]thiophene from step 3

(2.7 g, 0.013 mol) was carried out using BBr$_3$. After stirring the reaction mixture for 1 h at −78° C. and then overnight at RT, the solution was cooled to 0° C. and quenched by addition of water. The dichloromethane layer was separated and the aqueous layer was extracted in dichloromethane. The combined extracts were washed with water, sodium bicarbonate, brine and dried over anhydrous sodium sulphate and after removal of the solvent in vacuo, the resulting 4-chloro-benzo[b]thiophen-6-ol product was purified by column (silical gel, hexane:ethyl acetate/10:1).

$^1$H NMR (CDCl$_3$) δ ppm: 7.35 (1H, dd); 7.26 (1H, d); 7.21 (1H, dd); 6.70 (1H, d); MS m/z 184 (M$^+$).

Stage 2: Preparation 2-(4-chloro-benzo[b]thiophen-6-yloxy)-N-(2-methoxyimino-1,1-dimethyl-ethyl)-2-methylsulfanyl-acetamide 2-(4-chloro-benzo[b]thiophen-6-yloxy)-N-(2-methoxyimino-1,1-dimethyl-ethyl)-2-methylsulfanyl-acetamide was prepared from 4-chloro-benzo[b]thiophen-6-ol in a manner similar to that described in Example 1, Stage 1 (steps 1-2) and Stage 2, (Step 1) where 2-amino-2-methyl-propionaldehyde O-methyl-oxime from step 4 of Example 2 is used instead of 2-amino-2-methyl-1-propanol in the step 1 of Stage 2 of Example 1.

Compound No. 81: 2-(4-Chloro-benzo[b]thiophen-6-yloxy)-N-(2-methoxyimino-1,1-dimethyl-ethyl)-2-methylsulfanyl-acetamide 1H NMR (CDCl3) δ ppm: 7.54 (1H, s br); 7.41 (4H, s br); 7.14 (1H, d); 5.52 (1H, s); 3.88 (3H, s); 2.18 (3H, s); 1.59 (3H, s); 1.57 (3H, s); mp 120-122° C.

EXAMPLE 13

This Example illustrates the preparation of N-(2-Methoxyimino-1,1-dimethyl-ethyl)-3-(4-methyl-benzo[b]thiophen-6-yl)-2-methylsulfanyl-propionamide (Compound No. 82)

Stage 1: Preparation of 4-methyl-benzo[b]thiophen-6-ol

Step 1

To a cold (−78° C.) solution of 3-bromo-5-methoxy toluene (7 g, 0.035 mol) in dry THF (80 ml) under inert atmosphere, butyl lithium solution (1.6M solution in hexane; 32.8 mL, 0.05 mol) was added dropwise and the mixture was stirred for 1 h at same temperature. Dimethyl disulphide (4.6 ml, 0.05 mol) was then added dropwise and the reaction mixture was allowed to attain room temperature over a period of 2 h and stirred overnight at RT. The reaction mixture was quenched with ammonium chloride and extracted in diethyl ether. The combined organic extracts were washed with water and brine and dried. The solvent was evaporated in vacuo to yield 6.5 g of product, 1-isobutylsulfanyl-3-methoxy-5-methyl-benzene MS m/z 168 (M+).

Step 2

To a stirred solution of 3-methyl-5-methoxy thioanisole (6.5 g, 0.04 mol) in HMPA (100 ml), kept under N2 at 100° C., small pieces of sodium (2.29 g, 0.09 mmol) were added and the mixture was further stirred at 100° C. for 3 h. The reaction mass was allowed to come to room temperature and bromoacetaldehyde diethyl acetal (7 ml, 0.04 mol) was then added to this mixture and stirred overnight at room temperature. The reaction mixture was quenched with methanol and poured in cold water, extracted in ethyl acetate. The combined organic extracts were washed with water, brine and dried. The solvent was evaporated in vacuo to give 7 g of product (m/z 270 (M+)) that was used as such in the following step 3.

Step 3

A solution of product from step 2 (3 g, 0.01 mol) in dichloromethane (25 ml) was added drop wise to a solution of BF3.Et2O (1.2 mL, 0.01 mol) in dry dichloromethane (220 mL) at RT under nitrogen. The reaction was then stirred at RT for 3 h and quenched with aqueous $NaHCO_3$ solution. The organic layer was separated and the aqueous layer was extracted with dichloromethane. The combined organic extract was washed with water, brine, dried and concentrated. The residue was purified by flash chromatography (silica gel: hexane) to afford 6-methoxy-4-methylbenzo[b]thiophene, 0.55 g. MS m/z 178 (M+).

Step 4: 6-methoxy-4-methylbenzo[b]thiophene obtained in step 3

(0.550 g, 3 mmol) and pyridine hydrochloride (5 g, 40 mmol) was heated under nitrogen atmosphere at 200° C. for 3 h. The reaction mixture was then cooled, diluted with water and extracted in ethyl acetate. The combined organic extracts were washed with 2N HCl and brine and dried. The solvent was evaporated in vacuo to yield 0.5 g of 4-methyl-benzo[b]thiophen-6-ol used as such in Stage 2 below.

$^1$H NMR (CDCl3) δ ppm: 7.28 (1H, dd); 7.24 (1H, d); 7.15 (1H, d); 6.73 (1H, s br); 2.56 (3H, s); MS m/z 164 (M+).

Stage 2: Preparation of N-(2-Methoxyimino-1,1-dimethyl-ethyl)-3-(4-methyl-benzo[b]thiophen-6-yl)-2-methylsulfanyl-propionamide N-(2-methoxyimino-1,1-dimethyl-ethyl)-3-(4-methyl-benzo[b]thiophen-6-yl)-2-methylsulfanyl-propionamide was prepared from 4-methyl-benzo[b]thiophen-6-ol in a manner similar to that described in Example 1, Stage 1 (steps 1-2) and Stage 2, (Step 1) where 2-amino-2-methyl-propionaldehyde O-methyl-oxime from step 4 of Example 2 is used instead of 2-amino-2-methyl-1-propanol in the step 1 of Stage 2 of Example 1.

Compound No. 82: N-(2-Methoxyimino-1,1-dimethyl-ethyl)-3-(4-methyl-benzo[b]thiophen-6-yl)-2-methylsulfanyl-propionamide 1H NMR (CDCl$_3$) δ ppm: 8.10 (1H, s br); 7.61 (1H, d); 7.52 (1H, s); 7.44 (1H, d); 7.42 (1H, d); 5.80 (1H, s); 3.72 (3H, s); 2.54 (3H, s); 2.12 (3H, s); 1.41 (3H, s); 1.40 (3H, s).

EXAMPLE 14

This Example illustrates the preparation of 2-(7-Chlorobenzo[b]thiophen-5-yloxy)-N-(2-methoxyimino-1,1-dimethyl-ethyl)-2-methylsulfanyl-acetamide (Compound No. 83)

Stage 1: Preparation of 7-chloro-benzo[b]thiophene-5-ol

Step 1

To a solution of 2,3-dichloro-5-nitrobenzaldehyde (10 g, 0.045 mol) and methyl mercaptoacetate (6.6 mL, 0.06 mol) in DMF (200 mL) was added KOH (6 g) in 50 mL water. After stirring for 2 h, the reaction mixture was poured in ice cold water and the mixture was extracted in ethyl acetate. The organic layer was washed with water and dried. The evaporation of the solvent gave crude product which was purified by repetitive washing with hexane to yield 7-chloro-5-nitrobenzo[b]thiophene-2-carboxylic acid methyl ester, 12.3 g.

Step 2

To the solution of ester from step 2 (10.5 g, 0.038 mol) in methanol (30 mL), aqueous solution of NaOH (2.6 g in 10 mL of water) was added and the reaction mixture was refluxed for 4 h. Most of the methanol was removed and the mixture was diluted with water (25 mL) and washed with ether. The aqueous layer was then acidified with dil. HCl to afford solid which was filtered and washed with cold water and dried to give 7-chloro-5-nitro-benzo[b]thiophene-2-carboxylic acid, 8.7 g.

Step 3

To the suspension of acid (12.9 g, 0.05 mol) from step 2 in quinoline (200 ml) was added copper powder (5.2 g, 0.08 mol) and the mixture was heated at 200° C. for 2 h. The reaction mixture was cooled and extracted in ether. The ethereal layer was washed with 50% HCl, brine and dried over sodium sulphate and concentrated to yield 7-chloro-5-nitrobenzo[b]thiophene, 6.2 g which was used as such in Step 4, MS m/z 213 (M+).

Step 4

To the refluxing solution of 7-chloro-5-nitrobenzo[b]thiophen obtained in step 4 (4.4 g, 20 mmol) in 5% acetic acid (300 ml) and ethyl acetate (300 ml) was added portion wise iron powder (6 g, 100 mmol) and the mixture was refluxed for 4 h. The reaction mixture was cooled, filtered through celite and washed with ethyl acetate. The layers were separated and the aqueous layer was extracted in ethyl acetate. The combined organic extracts were washed with water, dried and concentrated. The residue was purified by column chromatography (silica gel, hexane:ethyl acetate/4:1) to give 7-chloro-benzo[b]thiophen-5-ylamine, 2 g. MS m/z 183 (M+).

Step 5

A dispersion of 7-chloro-benzo[b]thiophen-5-ylamine (2.3 g, 0.012 mol) in dil. sulphuric acid (14 ml conc. H2SO4 in 400 ml water) was heated to obtain the clear solution and it was cooled to 0° C. A cold solution of NaNO2 (0.9 g in 5 mL of water, 0.013 mol) was added dropwise and the mixture was stirred at same temperature for 1 h and then warmed to 10° C. over 30 min. Excess nitrite was then quenched with urea. The reaction mixture was then added to dil. sulphuric acid (8 mL conc. Sulphuric acid in 115 mL water) maintained at 90° C. and the mixture was further refluxed for 1 h. The reaction mixture was filtered hot and the filtrate was stirred overnight at room temperature. The mixture was extracted with ethyl acetate and the combined organic extracts were washed with water, brine, dried and concentrated. The residue was purified by column chromatography (silica gel, hexane:ethyl acetate/9:1) to give 0.4 g of 7-chloro-benzo[b]thiophene-5-ol.

$^1$H NMR (CDCl3) d ppm: 7.49 (1H, d); 7.23 (1H, d); 7.16 (1H, d); 6.97 (1H, d); MS m/z 184 (M+).

Stage 2: Preparation of 2-(7-chloro-benzo[b]thiophen-5-yloxy)-N-(2-methoxyimino-1,1-dimethyl-ethyl)-2-methylsulfanyl-acetamide 2-(7-Chloro-benzo[b]thiophen-5-yloxy)-N-(2-methoxyimino-1,1-dimethyl-ethyl)-2-methylsulfanyl-acetamide was prepared from 7-chloro-benzo[b]thiophene-5-ol from Stage 1, Step 5 above in a manner similar to that described in Example 1, Stage 1 (steps 1-2) and Stage 2, (Step 1) where 2-amino-2-methyl-propionaldehyde O-methyl-oxime from step 4 of Example 2 is used instead of 2-amino-2-methyl-1-propanol in the step 1 of Stage 2 of Example 1.

Compound No. 83: 2-(7-Chloro-benzo[b]thiophen-5-yloxy)-N-(2-methoxyimino-1,1-dimethyl-ethyl)-2-methylsulfanyl-acetamide 1H NMR (CDCl3) δ ppm: 7.56 (1H, s br); 7.54 (1H, d); 7.41 (1H, s); 7.33 (1H, d); 7.32 (1H, d); 7.14 (1H, d); 5.54 (1H, s); 3.87 (3H, s); 2.18 (3H, s); 1.59 (3H, s); 1.57 (3H, s).

EXAMPLE 15

This Example illustrates the preparation of N-(2-Methoxyimino-1,1-dimethyl-ethyl)-2-(7-methyl-benzo[b]thiophen-5-yloxy)-2-methylsulfanyl-acetamide (Compound No. 84).

Stage 1: Preparation of 7-methyl-benzo[b]thiophen-5-ol

Step 1

To the cold (−78° C.) solution of 2-bromo-5-methoxy toluene (8 g, 0.04 mol) in dry THF (80 mL) under inert atmosphere, butyl lithium solution (1.6M solution in hexane; 36.8 mL, 0.058 mol) was added dropwise and the mixture was stirred for 1 h at same temperature. Dimethyl disulphide (7.7 mL, 0.08 mol) was then added dropwise and the reaction mixture was allowed to warm to room temperature over a period of 2 h. The reaction mixture was quenched with sat. ammonium chloride solution and extracted in diethyl ether. The combined organic extracts were washed with water and brine and dried. The solvent was evaporated in vacuo to yield 6.5 g of 2-methyl-4-methoxy thioanisole, which was used as such in Step 2 MS m/z 168 (M+).

Step 2

To a stirred solution of 2-methyl-4-methoxy thioanisole (8.0 g, 0.04 mol) in HMPA (130 mL), kept under $N_2$ at 100° C., small pieces of sodium (2.9 g, 0.12 mol) were added and the mixture was further stirred at 100° C. for 4 h. The reaction mass was allowed to come to room temperature and bromoacetaldehyde diethyl acetal (8 mL, 0.05 mmol) was then added to this mixture and stirred for 2 h. The reaction mixture was quenched with methanol and poured in cold water and extracted in ether. The combined organic extracts were washed with water and brine and dried. The solvent was evaporated in vacuo and the residue was purified by flash column chromatography (silica gel; hexane:ethyl acetate/9:1) to yield 8.5 g of 1-(2,2-diethoxy-ethylsulfanyl)-4-methoxy-2-methyl-benzene. MS m/z 270 (M+).

Step 3

To the hot (130° C.) solution of polyphosphoric acid (20 mL) in chlorobenzene (50 mL) was added dropwise a solution of 1-(2,2-diethoxy-ethylsulfanyl)-4-methoxy-2-methyl-benzene from step 2 (6.8 g, 0.025 mol) in chlorobenzene (25 mL) over a period of 2 h and stirred for 2 h at same temperature. The reaction mixture was cooled to room temperature and stirred for 12 h. The mixture was then cooled and diluted with water and the layers were separated. The aqueous layer was extracted in ethyl acetate. The combined organic layers were washed with water, dried and concentrated. The crude material was purified by chromatography (silica gel: hexane:ethyl acetate/4:1) to provide 2 g of 7-methyl-5-methoxy benzothiophene. MS m/z 178 (M+).

Step 4

To a solution of 7-methyl-5-methoxy benzothiophene from step 3 (2 g, 11 mmol) in dry dichloromethane (60 mL) at −78° C. was added boron tribromide (1.3 mL in 10 mL dichloromethane, 13 mmol) over 20 minutes. The reaction mixture was stirred for 1 h at −78° C. and then stirred 4 at RT. The solution was cooled to 0° C. quenched by cautious addition of water. The dichloromethane layer was separated and the aqueous layer was extracted in dichloromethane. The combined extracts were washed with water, sodium bicarbonate, brine and dried over anhydrous sodium sulphate and concentrated. The residue was purified by column chromatography (silica gel:hexane:ethyl acetate/4:1) to give 1.4 g of product, 7-methyl-5-hydroxy benzothiophene which was used as such in next step described below (Stage 2).

$^1$H NMR (CDCl$_3$) δ ppm: 7.42 (1H, d); 7.23 (1H, d); 7.10 (1H, d); 6.75 (1H, d); 2.52 (3H, s); MS m/z 164 (M+).

Stage 2: Preparation of N-(2-Methoxyamino-1,1-dimethyl-ethyl)-2-(7-methyl-benzo[b]thiophen-5-yloxy)-2-methylsulfanyl-acetamide N-(2-Methoxyimino-1,1-dimethyl-ethyl)-2-(7-methyl-benzo[b]thiophen-5-yloxy)-2-methylsulfanyl-acetamide was prepared from 7-methyl-5-hydroxy benzothiophene from Stage 1, Step 5 above in a manner similar to that described in Example 1, Stage 1 (steps 1-2) and Stage 2, (Step 1) where 2-amino-2-methyl-propionaldehyde O-methyl-oxime from step 4 of Example 2 is used instead of 2-amino-2-methyl-1-propanol in the step 1 of Stage 2 of Example 1.

Compound No. 84: N-(2-methoxyimino-1,1-dimethyl-ethyl)-2-(7-methyl-benzo[b]thiophen-5-yloxy)-2-methylsulfanyl-acetamide $^1$H NMR (CDCl$_3$) δ ppm: 7.55 (1H, s br); 7.47 (1H, d); 7.43 (1H, s); 7.29 (1H, d); 7.28 (1H, d); 6.91 (1H, s br); 5.54 (1H, s); 3.87 (3H, s); 2.56 (3H, s); 2.18 (3H, s); 1.59 (3H, s); 1.57 (3H, s); mp 115-117° C.

EXAMPLE 16

This Example illustrates the preparation of 2-(7-Bromo-4-methyl-naphthalen-2-yl oxy)-N-(2-methoxyimino-1,1-dimethyl-ethyl)-2-methylsulfanyl-acetamide (Compound No. 85)

Stage 1: Preparation of 7-bromo-4-methyl-naphthalen-2-ol

Step 1

To the cold (−10° C.) solution of 7-methoxy-5-methyl-3,4-dihydro-2H-naphthalen-1-one (8.3 g, 0.04 mol) in methanol (20 mL), the solution of bromine (2.3 mL, 0.04 mol) in methanol (10 mL) was added dropwise and the mixture was stirred for 2 h while allowing the temperature to rise to room temperature. Methanol was evaporated in vacuo and the mixture was diluted with ethyl acetate and washed with aqueous sodium thiosulphate solution followed by saturated sodium bicarbonate, brine and dried. Evaporation of the solvent gave 2-bromo-7-methoxy-5-methyl-3,4-dihydro-2H-naphthalen-1-one as an off-white solid, 10 g, which was used as such in step 2. MS m/z 271 (M+2).

Step 2

To the ice-cold solution of 2-bromo-7-methoxy-5-methyl-3,4-dihydro-2H-naphthalen-1-one (10 g, 0.04 mol) obtained in Step 1 in methanol (100 mL) was added sodium borohydride (2.0 g, 0.05 mol) and the mixture was stirred for 2 h at room temperature. The reaction mixture was cooled and quenched with acetone and concentrated. The mixture was diluted with water and extracted in diethyl ether. The organic layer was washed with brine, dried and concentrated to yield the 2-bromo-7-methoxy-5-methyl-1,2,3,4-tetrahydro-naphthalen-1-ol, 8.0 g, which was used as such in Step 3.

Step 3

To the refluxing solution of naphthalen-1-ol (8.0 g, 0.03 mol) obtained in Step 3 in toluene (30 mL), cat. PTSA (400 mg) was added and the mixture was stirred at reflux for 4 h. Toluene was evaporated and the mixture was diluted with water and extracted in diethyl ether. The organic layer was washed with sodium bicarbonate, brine, dried and evaporated. The crude material was purified by chromatography (silica gel:hexane:ethyl acetate/10:1) to provide 3-bromo-6-methoxy-8-methyl-1,2-dihydro-naphthalene, 8.0 g, which was used as such in Step 4.

Step 4

To the solution of 3-bromo-6-methoxy-8-methyl-1,2-dihydro-naphthalene (8.0 g, 0.03 mol) from Step 3 in 1,4-dioxane (40 ml), DDQ (7.9 g, 0.03 mol) was added and the mixture was refluxed for 2 h. The solvent was removed and the crude product was purified by chromatography (silica gel:hexane:ethyl acetate/20:1) to provide 6-bromo-3-methoxy-1-methyl-naphthalene, 3.7 g.

Step 5

The suspension of 6-bromo-3-methoxy-1-methyl-naphthalene (3.7 g, 0.015 mol), from Step 4, in 38% HBr-acetic acid (20 mL) was refluxed for 16 h. The mixture was then extracted in ethyl acetate and the extract was basified with 10% sodium hydroxide solution and the layers were separated. The aqueous layer was acidified with dil. HCl and extracted with ethyl acetate. The organic layer was washed with brine, dried and concentrated to give 7-bromo-4-methyl-naphthalen-2-ol, 1.9 g which was used as such in next step.
$^1$H NMR (CDCl$_3$) δ ppm: 7.8 (1H, d); 7.75 (1H, d); 7.41 (1H, dd); 6.95 (1H, s); 6.90 (1H, s); 2.63 (3H, s); MS m/z 238 (M+2).

Stage 2: Preparation of 2-(7-bromo-4-methyl-naphthalen-2-yloxy)-N-(2-methoxyimino-1,1-dimethyl-ethyl)-2-methylsulfanyl-acetamide 2-(7-bromo-4-methyl-naphthalen-2-yloxy)-N-(2-methoxyimino-1,1-dimethyl-ethyl)-2-methylsulfanyl-acetamide was prepared from 7-bromo-4-methyl-naphthalen-2-ol from Stage 1, Step 5 above in a manner similar to that described in Example 1, Stage 1 (steps 1-2) and Stage 2, (Step 1) where 2-amino-2-methyl-propionaldehyde O-methyl-oxime from step 4 of Example 2 is used instead of 2-amino-2-methyl-1-propanol in the step 1 of Stage 2 of Example 1.

Compound No. 85: 2-(7-bromo-4-methyl-naphthalen-2-yloxy)-N-(2-methoxyimino-1,1-dimethyl-ethyl)-2-methylsulfanyl-acetamide $^1$H NMR (CDCl$_3$) δ ppm: 7.91 (1H, s); 7.78 (1H, d); 7.56 (1H, s br); 7.53 (1H, d); 7.49 (1H, d); 7.41 (1H, s); 7.08 (1H, s); 7.06 (1H, s); 5.62 (1H, s); 3.87 (3H, s); 2.65 (1H, s); 2.18 (3H, s); 1.59 (3H, s); 1.56 (3H, s); mp 104-107° C.

EXAMPLE 17

This Example illustrates the preparation of 2-(benzothiazol-5-yloxy)-N-(2-methoxyimino-1,1-dimethyl-ethyl)-2-methylsulfanyl-acetamide (Compound No. 86)

Step 1

2-(benzothiazol-5-yloxy)-N-(2-methoxyimino-1,1-dimethyl-ethyl)-2-methylsulfanyl-acetamide was prepared from benzothiazol-5-ol in a manner similar to that described in Example 1, Stage 1 (steps 1-2) and Stage 2, (Step 1) where 2-amino-2-methyl-propionaldehyde O-methyl-oxime from step 4 of Example 2 is used instead of 2-amino-2-methyl-1-propanol in the step 1 of Stage 2 of Example 1.

Compound No. 86: $^1$H NMR (CDCl$_3$) δ ppm: 9.02 (1H, s); 7.89 (1H, d); 7.77 (1H, d); 7.62 (1H, s); 7.42 (1H, s); 7.20 (1H, dd); 5.61 (1H, s); 3.87 (3H, s); 2.18 (3H, s); 1.60 (3H, s); 1.58 (3H, s)

EXAMPLE 18

This Example illustrates the preparation of N-(2-methoxy-imino-1,1-dimethyl-ethyl)-2-(7-methyl-benzothiazol-5-yloxy)-2-methylsulfanyl-acetamide (Compound No. 87)

Stage 1: Preparation of 7-methyl-benzothiazol-5-ol

Step 1: 5-amino-7-methyl benzothiazole (6 g, 36 mmol) was dissolved in sulphuric acid (38 ml con. sulphuric acid in 550 mL water) by heating the suspension for 2 h and the resulting solution was cooled to 0° C. with ice. A solution of sodium nitrite (3.1 g, 45 mmol) in water (10 mL) was then added and the mixture was stirred at same temperature for 1 h and then warmed to 15° C. over 30 min. Excess nitrite was quenched with urea (1 g). The solution was then added rapidly to refluxing dil. sulphuric acid (22 ml) sulphuric acid (10 ml of water) and refluxed continued for another 1 h. The mixture was filtered and the filtrate was stirred overnight and extracted in ethyl acetate. The combined organic extracts were washed with water, brine and dried. The solvent was evaporated in vacuo to yield 1 g of 5-hydroxy-7-methyl benzothiazole, which was used as such in next step.

$^1$H NMR (CDCl$_3$) δ ppm: 9.0 (1H, s); 7.47 (1H, d); 6.88 (1H, d); 2.54 (3H, s); MS m/z 166 (M+1).

Stage 2: Preparation of N-(2-methoxyimino-1,1-dimethyl-ethyl)-2-(7-methyl-benzothiazol-5-yloxy)-2-methylsulfanyl-acetamide N-(2-methoxyimino-1,1-dimethyl-ethyl)-2-(7-methyl-benzothiazol-5-yloxy)-2-methylsulfanyl-acetamide was prepared from 5-hydroxy-7-methyl benzothiazole from Stage 1, Step 1 above in a manner similar to that described in Example 1, Stage 1 (steps 1-2) and Stage 2, (Step 1) where 2-amino-2-methyl-propionaldehyde O-methyl-oxime from step 4 of Example 2 is used instead of 2-amino-2-methyl-1-propanol in the step 1 of Stage 2 of Example 1.

Compound No. 87: N-(2-methoxyimino-1,1-dimethyl-ethyl)-2-(7-methyl-benzothiazol-5-yloxy)-2-methylsulfanyl-acetamide $^1$H NMR (CDCl$_3$) δ ppm: 9.00 (1H, s); 7.61 (1H, d); 7.42 (1H, s); 7.01 (1H, s); 5.59 (1H, s); 3.87 (3H, s); 2.59 (3H, s); 2.18 (3H, s); 1.60 (3H, s); 1.58 (3H, s); mp 148-150° C.

EXAMPLE 19

This Example illustrates the preparation of 2-(benzooxazol-5-yloxy)-N-(2-methoxyimino-1,1-dimethyl-ethyl)-2-methylsulfanyl-acetamide Compound No. 88

Step 1

2-(Benzooxazol-5-yloxy)-N-(2-methoxyimino-1,1-dimethyl-ethyl)-2-methyl sulfanyl-acetamide was prepared from benzooxazol-5-oll in a manner similar to that described in Example 1, Stage 1 (steps 1-2) and Stage 2, (Step 1) where 2-amino-2-methyl-propionaldehyde O-methyl-oxime from step 4 of Example 2 is used instead of 2-amino-2-methyl-1-propanol in the step 1 of Stage 2 of Example 1.

Compound No. 88: $^1$H NMR (CDCl$_3$) δ ppm: 8.10 (1H, s); 7.59 (1H, s br); 7.56 (1H, s br); 7.53 (1H, d); 7.44 (1H, d); 7.42 (1H, s); 7.11 (1H, dd); 5.52 (1H, s); 3.87 (3H, s); 2.17 (1H, s); 1.60 (3H, s); 1.58 (3H, s); mp 95-96° C.

EXAMPLE 20

Example 20 provides additional characterising NMR data and/or melting points for further prepared compounds that are in part listed in the Tables cited above and have been prepared using procedures similar to those described in Examples 1-19 unless specified otherwise. Unless stated otherwise, the $^1$H NMR signals reported are those that characterize the major diasteroisomer.

Compound No. 89: N-(2-Methoxyimino-1,1-dimethyl-ethyl)-2-(4-methyl-benzothiazol-6-yloxy)-2-methylsulfanyl-acetamide $^1$H NMR (CDCl$_3$) δ ppm: 8.87 (1H, s); 7.54 (1H, s, br); 7.41 (1H, s); 7.38 (1H, d); 7.03 (1H, d); 5.54 (1H, s), 3.86 (3H, s); 2.75 (3H, s); 2.17 (3H, s); 1.58 (3H, s); 1.56 (3H, s).

Compound No. 90: 2-(3,8-Dichloro-quinolin-6-yloxy)-N-(2-methoxyimino-1,1-dimethyl-ethyl)-2-methylsulfanyl-acetamide: mp: 158-161° C.

Compound No. 91: N-(2-Methoxyimino-1,1-dimethyl-ethyl)-2-(8-methyl-quinazolin-6-yloxy)-2-methylsulfanyl-acetamide: mp: 109-112° C.

Compound No. 92: 2-(3-iodo-quinolin-6-yloxy)-N-(3-methoxyimino-1,1-dimethyl-propyl)-2-methylsulfanyl-acetamide $^1$H NMR (CDCl$_3$) δ ppm: 8.88 (1H, d); 8.39 (1H, d); 7.95 (1H, d); 7.39 (1H, m); [{7.30 (t), 6.66 (t) 1H}, isomer A and isomer B]; 7.07 (1H, d); [{6.77 (s, br), 6.54 (s, br) 1H}, isomer A and isomer B]; [{5.50 (s), 5.47 (s) 1H}, isomer A and isomer B]; [{3.82 (s), 3.74 (s) 3H}, isomer A and isomer B]; [{3.38-3.43 (m), 2.57 (d, d) 2H}, isomer A and isomer B]; [{2.13 (s), 2.12 (s) 3H}, isomer A and isomer B]; 1.38 (6H, s). MP 117-118° C.

Compound No. 93: 2-(3-Bromo-quinolin-6-yloxy)-N-(2-methoxyimino-ethyl)-2-methylsulfanyl-acetamide $^1$H NMR (CDCl$_3$) δ ppm: 8.79 (1H, d); 8.15 (1H, d); 8.06 (1H, d); 7.43 (1H, m); 7.38 (1H, m); 7.18 (1H, m); 7.09 (1H, m, br); 5.69 (1H, d); 4.06 (2H, m); 3.77 (3H, a); 3.24 (1H, s); 2.13 (3H, d).

Compound No. 94: 2-(3-Bromo-quinolin-6-yloxy)-N-(2-methoxyimino-1-methyl-ethyl)-2-methylsulfanyl-acetamide $^1$H NMR (CDCl$_3$) δ ppm: 8.50 (1H, d); 8.21 (1H, d); 8.07 (1H, d); [{7.50 (m), 7.46 (m) 1H}, isomer A and isomer B]; [{7.41 (d), 7.40 (d) 1H}, isomer A and isomer B]; 7.25, (1H, s, br); [{5.76 (s), 5.74 (s) 1H}, isomer A and isomer B]; [{4.82 (m), 4.75 (m) 1H}, isomer A and isomer B]; [{3.91 (d), 3.78 (d) 3H}, isomer A and isomer B]; 3.32 (1H, s); 2.18 (3H, d); [{1.42 (d), 1.38 (d) 3H}, isomer A and isomer B];

Compound No. 95: 2-(3-Ethynyl-quinolin-6-yloxy)-N-(3-methoxyimino-1,1-dimethyl-propyl)-2-methyl-sulfanyl-acetamide $^1$H NMR (CDCl$_3$) δ ppm: 8.85 (1H, d); 8.21 (1H, d); 8.07 (1H, d); 7.47 (1H, m); 7.38 (1H, m); 6.65 (1H, s, br); 5.61 (1H, d); 3.81 (3H, d); 3.31 (1H, d); 2.66 (2H, dd); 2.20 (3H, d); 1.46 (6H, d).

Compound No. 96: N-[1,1-Dimethyl-3-(tetrahydro-pyran-2-yloxyimino)-propyl]-2-(3-iodo-8-methyl-quinolin-6-yloxy)-2-methylsulfanyl-acetamide $^1$H NMR (CDCl$_3$) δ ppm: 8.95 (1H, d); 8.44 (1H, d); 7.52 (1H, m); 7.33 (1H, s, br); 6.99 (1H, s, br); [{6.66 (s, br), 6.59 (s, br) 1H}, isomer A and isomer B]; 5.59 (1H, s); 5.21 (1H, s, br); 3.80-3.92 (1H, m), 3.50-3.65 (1H, m); 2.77 (3H, s); 2.68-2.77 (2H, m); 2.20 (3H, s); 1.40-1.86 (6H, m); 1.40-1.48 (6H, m). MP 105-106° C.

Compound No. 97: N-(3-Butoxyimino-1,1-dimethyl-propyl)-2-(3-iodo-8-methyl-quinolin-6-yloxy)-2-methylsulfanyl-acetamide $^1$H NMR (CDCl$_3$) δ ppm: 8.96 (1H, d); 8.43 (1H, d); [{7.40 (t), 6.72 (t) 1H}, isomer A and isomer B]; 7.32 (1H, s br); 6.98 (1H, d); [{6.76 (s, br), 6.66 (s, br) 1H}, isomer A and isomer B]; [{5.58 (s), 5.55 (s) 1H}, isomer A and isomer B]; 4.10 (t), 4.02 (t) 2H}, isomer A and isomer B]; [{2.82 (t), 2.65 (d) 2H}, isomer A and isomer B]; 2.77 (3H, s); [{2.21 (s), 2.19 (s) 3H}, isomer A and isomer B]; 1.57-1.67 (2H, m); 1.47 (6H, s); 1.31-1.41 (2H, m); 0.88-0.95 (3H, m).

Compound No. 98: N-(3-Benzyloxyimino-1,1-dimethyl-propyl)-2-(3-iodo-8-methyl-quinolin-6-yloxy)-2-methylsulfanyl-acetamide $^1$H NMR (CDCl$_3$) δ ppm: 8.96 (1H, d); 8.42 (1H, d); [{7.48 (t), 6.77 (t) 1H}, isomer A and isomer B]; 7.32-7.36 (6H, m); [{6.97 (d), 6.95 (d) 1H}, isomer A and isomer B]; [{6.71 (s, br), 6.61 (s, br) 1H}, isomer A and isomer B]; [{5.56 (s), 5.53 (s) 1H}, isomer A and isomer B]; [{5.15 (s), 5.07 (s) 2H}, isomer A and isomer B]; [{2.85-2.96 (m), 2.70 (d) 2H}, isomer A and isomer B]; 2.76 (3H, s); 2.19 (3H, s); [{1.48 (s), 1.45 (s) 6H}, isomer A and isomer B].

Compound No. 99: N-(3-Allyloxyimino-1,1-dimethyl-propyl)-2-(3-iodo-8-methyl-quinolin-6-yloxy)-2-methylsulfanyl-acetamide $^1$H NMR (CDCl$_3$) δ ppm: 8.95 (1H, d); 8.42 (1H, d); [{7.44 (t), 6.73 (t) 1H}, isomer A and isomer B]; 7.31 (1H, s); 6.98 (1H, d); [{6.78 (s, br), 6.62 (s, br) 1H}, isomer A and isomer B]; 5.89-6.04 (1H, m); [{5.58 (s), 5.55 (s) 1H}, isomer A and isomer B]; 5.17-5.32 (2H, m); [{4.60 (d), 4.52 (d) 2H}, isomer A and isomer B]; [{2.80-2.92 (m), 2.68 (d) 2H}, isomer A and isomer B]; 2.76 (3H, s); [{2.21 (s), 2.20 (s) 3H}, isomer A and isomer B]; [{1.48 (s), 1.47 (s) 6H}, isomer A and isomer B].

Compound No. 100: N-(3-tert-Butoxyimino-1,1-dimethyl-propyl)-2-(3-iodo-8-methyl-quinolin-6-yloxy)-2-methylsulfanyl-acetamide $^1$H NMR (CDCl$_3$) δ ppm: 8.96 (1H, d); 8.43 (1H, d); [{7.38 (t), 6.71 (t) 1H}, isomer A and isomer B]; 7.32 (1H, s, br); 6.98 (1H, s, br); 6.60 (1H, s, br); [{5.58 (s), 5.54 (s) 1H}, isomer A and isomer B]; [{2.81-2.85 (m), 2.64-2.66 (m) 2H}, isomer A and isomer B]; 2.77 (3H, s); [{2.22 (s), 2.19 (s) 3H}, isomer A and isomer B]; 1.48 (6H, s); [{1.30 (s), 1.27 (s) 9H}, isomer A and isomer B]. MP 130-131° C.

Compound No. 101: N-(3-Hydroxyimino-1,1-dimethyl-propyl)-2-(3-iodo-8-methyl-quinolin-6-yloxy)-2-methylsulfanyl-acetamide $^1$H NMR (CDCl$_3$) δ ppm: 8.99 (1H, s, br); 8.49 (1H, s, br); [{7.45 (t), 6.85 (t) 1H}, isomer A and isomer B]; 7.32 (1H, s, br); 7.00 (1H, s, br); [{6.97 (s, br), 6.59 (s, br) 1H}, isomer A and isomer B]; [{5.59 (s), 5.58 (s) 1H}, isomer A and isomer B]; [{2.86 (t), 2.72 (d) 2H}, isomer A and isomer B]; 2.79 (3H, s); [{2.21 (s), 2.21 (s) 3H}, isomer A and isomer B]; [{1.53 (d), 1.47 (s) 6H}, isomer A and isomer B]. MP 68-69° C.

Compound No. 102: 2-(3-Iodo-8-methyl-quinolin-6-yloxy)-N-(3-methoxy-methoxyimino-1,1-dimethyl-propyl)-2-methylsulfanyl-acetamide $^1$H NMR (CDCl$_3$) δ ppm: 8.97 (1H, d); 8.45 (1H, d); 7.51 (1H, t) Isomer A; 6.83 (1H, t) Isomer B; 7.34 (1H, s br) Isomer A; 7.33 (1H, s br) Isomer B; 6.99 (1H, d); 6.64 (1H, s, br) Isomer B; 6.59 (1H, s, br) Isomer A; 5.59 (1H, s) Isomer A; 5.57 (1H, s) Isomer B; 5.13 (2H, d) Isomer B; 5.03 (1H, d) Isomer A; 3.45 (3H, s) Isomer B; 3.40 (3H, s) Isomer A; 2.90-3.01 (2H, m); 2.78 (3H, s) Isomer B; 2.74 (3H, s) Isomer A; 2.22 (3H, d); 1.49 (6H, s).

Compound No. 103: 2-(3-Iodo-8-methyl-quinolin-6-yloxy)-N-(3-methoxyacetoxyimino-1,1-dimethyl-propyl)-2-methylsulfanyl-acetamide $^1$H NMR (CDCl$_3$) δ ppm: 8.97 (1H, d); 8.45 (1H, d); 7.74 (1H, t); 7.34 (1H, d) 7.00 (1H, d); 6.53 (1H, s br); 5.60 (1H, s); 4.11 (2H, s); 3.47 (3H, s); 2.95 (2H, t); 2.78 (3H, s); 2.21 (3H, s); 1.50 (3H, s); 1.47 (3H, s). MP 95-96° C.

Compound No. 104: 2-(3-Bromo-quinolin-6-yloxy)-N-(3-methoxyimino-1,1-dimethyl-butyl)-2-methyl-sulfanyl-acetamide $^1$H NMR (CDCl$_3$) δ ppm: 8.79 (1H, d); 8.23 (1H, d); 8.02 (1H, d); [{7.77 (s, br), 7.34 (s, br) 1H}, isomer A and isomer B]; 7.48 (1H, m); 7.18 (1H, d); [{5.57 (s), 5.48 (s) 1H}, isomer A and isomer B]; [{3.85 (s), 3.81 (s) 3H}, isomer A and isomer B]; 2.42-2.51 (2H, m); [{2.19 (s), 2.15 (s) 3H}, isomer A and isomer B]; [{1.92 (s), 1.87 (s) 3H}, isomer A and isomer B]; [{1.49 (s), 1.47 (s) 6H}, isomer A and isomer B].

Compound No. 105: 2-(3-Iodo-8-methyl-quinolin-6-yloxy)-N-(3-methoxyimino-1-methyl-propyl)-2-methylsulfanyl-acetamide $^1$H NMR (CDCl$_3$) δ ppm: 8.92 (1H, d); 8.41 (1H, d); [{7.39 (t), 6.68 (t) 1H}, isomer A and isomer B]; 7.30 (1H, m); 6.95 (1H, m); 6.75 (1H, m); 5.62-5.65 (1H, m); 4.27-4.34 (1H, m); 3.69-3.91 (3H); 2.74 (3H, s); 2.34-2.50 (2H, m); 2-14-2.17 (3H, m); 1.19-1.31 (3H, m). MP 95-96° C.

Compound No. 106: 2-(8-Chloro-3-iodo-quinolin-6-yloxy)-N-(2-methoxyimino-1,1-dimethyl-ethyl)-2-methylsulfanyl-acetamide $^1$H NMR (CDCl$_3$) δ ppm: 9.03 (1H, d); 8.47 (1H, d); 7.61 (1H, d); 7.55 (1H, s, br); 7.38 (1H, s); 7.08 (1H, d); 5.61 (1H, s), 3.87 (3H, s); 2.16 (3H, s); 1.59 (3H, s); 1.56 (3H, s). MP 191-192° C.

Compound No. 107: 2-(3-Bromo-8-methoxy-quinolin-6-yloxy)-N-(2-methoxyimino-1,1-dimethyl-ethyl)-2-methylsulfanyl-acetamide $^1$H NMR (CDCl$_3$) δ ppm: 8.77 (1H, d); 8.18 (1H, d); 7.52 (1H, s, br); 7.39 (1H, s); 6.80 (1H, d); 6.72 (1H, d); 5.62 (1H, s), 4.06 (3H, s); 3.85 (3H, s); 2.20 (3H, s); 1.58 (3H, s); 1.56 (3H, s).

Compound No. 108: 2-(3-Bromo-1-oxy-quinolin-6-yloxy)-N-(2-methoxyimino-1,1-dimethyl-ethyl)-2-methylsulfanyl-acetamide $^1$H NMR (CDCl$_3$) δ ppm: 8.61 (1H, d); 8.51 (1H, d); 7.80 (1H, s); 7.58 (1H, s, br); 7.42 (1H, m); 7.38 (1H, s); 7.20 (1H, d); 5.64 (1H, s), 3.86 (3H, s); 2.18 (3H, s); 1.59 (3H, s); 1.56 (3H, s).

Compound No. 109: N-(2-Benzyloxyimino-1,1-dimethyl-ethyl)-2-(3-bromo-quinolin-6-yloxy)-2-methylsulfanyl-acetamide $^1$H NMR (CDCl$_3$) δ ppm: 8.82 (1H, d); 8.23 (1H, d); 8.03 (1H, d); 7.58 (1H, s br); 7.47 (1H, s); 7.30-7.36 (6H, m); 7.15 (1H, d); 5.62 (1H, s); 5.10 (2H, s); 2.15 (3H, s); 1.61 (3H, s); 1.58 (3H, s).

Compound No. 110: N-(2-Benzyloxyimino-1,1-dimethyl-ethyl)-2-(3-bromo-8-methyl-quinolin-6-yloxy)-2-methylsulfanyl-acetamide $^1$H NMR (CDCl$_3$) δ ppm: 8.82 (1H, d); 8.20 (1H, d); 7.59 (1H, s br); 7.48 (1H, s); 7.29-7.38 (6H, m); 7.00 (1H, d); 5.61 (1H, s); 5.10 (2H, s); 2.77 (3H, s); 2.15 (3H, s); 1.58 (3H, s); 1.61 (3H, s).

Compound No. 111: 2-(3-Bromo-quinolin-6-yloxy)-N-{2-[(E or Z)-methoxyimino]-1,1-dimethyl-propyl}-2-methylsulfanyl-acetamide $^1$H NMR (CDCl$_3$) δ ppm: 8.81 (1H, d); 8.36 (1H s br); 8.24 (1H, d); 8.03 (1H, d); 7.45-7.48 (1H, d, d); 7.17 (1H, s); 5.63 (1H, s); 3.92 (3H, s); 2.20 (3H, s); 1.85 (3H, s); 1.63 (3H, s); 1.58 (3H, s).

Compound No. 112: 2-(3-Ethynyl-8-methyl-quinolin-6-yloxy)-N-(2-methoxyimino-1,1-dimethyl-ethyl)-2-methylsulfanyl-acetamide $^1$H NMR (CDCl$_3$) δ ppm: 8.86 (1H, d); 8.17 (1H, d); 7.56 (1H, s br); 7.41 (1H, s); 7.33 (1H, dd); 7.05 (1H, d); 5.63 (1H, s); 3.88 (3H, s); 3.28 (1H, s); 2.78 (3H, s); 2.20 (3H, s); 1.60 (3H, s); 1.57 (3H, s).

Compound No. 113 N-(2-Ethoxyimino-1,1-dimethyl-ethyl)-2-(3-Ethynyl-8-methyl-quinolin-6-yloxy)-2-methylsulfanyl-acetamide $^1$H NMR (CDCl$_3$) δ ppm: 8.86 (1H, d); 8.17 (1H, d); 7.56 (1H, s br); 7.40 (1H, s); 7.32 (1H, dd); 7.05 (1H, d); 5.63 (1H, s); 4.10-4.15 (2H, q); 3.28 (1H, s); 2.78 (3H, s); 2.20 (3H, s); 1.60 (3H, s); 1.57 (3H, s) 1.28 (3H, t).

Compound No. 114: N-(2-Allyloxyimino-1,1-dimethyl-ethyl)-2-(3-Ethynyl-8-methyl-quinolin-6-yloxy)-2-methylsulfanyl-acetamide $^1$H NMR (CDCl$_3$) δ ppm: 8.86 (1H, d); 8.17 (1H, d); 7.60 (1H, s br); 7.45 (1H, s); 7.32 (1H, dd); 7.05 (1H, d); 5.94-6.04 (1H, m); 5.63 (1H, s); 5.22-5.35 (2H, m); 4.57 (2H, d, d); 3.28 (1H, s); 2.78 (3H, s); 2.19 (3H, s); 1.61 (3H, s); 1.58 (3H, s).

Compound No. 115: 2-(8-Chloro-3-ethynyl-quinolin-6-yloxy)-N-(2-methoxyimino-1,1-dimethyl-ethyl)-2-methylsulfanyl-acetamide $^1$H NMR (CDCl$_3$) δ ppm: 8.95 (1H, d); 8.22 (1H, d); 7.64 (1H, d); 7.57 (1H, s br); 7.40 (1H, s); 7.17, (1H, d); 5.64 (1H, s); 3.89 (3H, s); 3.34 (1H, s); 2.20 (3H, s); 1.60 (3H, s); 1.58 (3H, s).

Compound No. 116: 2-(8-Chloro-3-ethynyl-quinolin-6-yloxy)-N-(2-ethoxyimino-1,1-dimethyl-ethyl)-2-methylsulfanyl-acetamide $^1$H NMR (CDCl$_3$) δ ppm: 8.95 (1H, d); 8.22 (1H, d); 7.65 (1H, s br); 7.63 (1H, d); 7.39 (1H, s); 7.16, (1H, d); 5.63 (1H, s); 4.11-4.16 (2H, q); 3.34 (1H, s); 2.20 (3H, s); 1.60 (3H, s); 1.58 (3H, s); 1.29 (3H, t).

Compound No. 117: N-(2-Allyloxyimino-1,1-dimethyl-ethyl)-2-(8-chloro-3-ethynyl-quinolin-6-yloxy)-2-methylsulfanyl-acetamide $^1$H NMR (CDCl$_3$) δ ppm: 8.95 (1H, d); 8.22 (1H, d); 7.63 (1H, d); 7.44 (1H, s); 7.16, (1H, d); 5.95-6.05 (1H, m); 5.63 (1H, s); 5.25-5.36 (2H, m); 4.59 (2H, d); 3.34 (1H, s); 2.19 (3H, s); 1.61 (3H, s); 1.58 (3H, s).

Compound No. 118: N-(2-Ethoxyimino-1,1-dimethyl-ethyl)-2-(3-ethynyl-quinolin-6-yloxy)-2-methylsulfanyl-acetamide $^1$H NMR (CDCl$_3$) δ ppm: 8.85 (1H, d); 8.21 (1H, d); 8.07 (1H, d); 7.67 (1H, s br); 7.44-7.47 (1H, d, d); 7.40 (1H, s); 7.22, (1H, d); 5.65 (1H, s); 4.13 (2H, q); 3.29 (1H, s); 2.20 (3H, s); 1.61 (3H, s); 1.58 (3H, s); 1.28 (3H, t).

Compound No. 119: N-(2-Ethoxyimino-1,1-dimethyl-ethyl)-2-(3-ethynyl-quinolin-6-yloxy)-2-methylsulfanyl-acetamide $^1$H NMR (CDCl$_3$) δ ppm: 8.85 (1H, s); 8.20 (1H, s); 8.07 (1H, d); 7.67 (1H, s br); 7.44-7.47 (1H, d, d); 7.40 (1H, s) Isomer A, 6.70 (1H, s) Isomer B; 7.22, (1H, d); 5.65 (1H, s) Isomer A, 5.61 (1H, s) Isomer B; 4.00-4.15 (2H, m) Isomer A and Isomer B; 3.29 (1H, s); 2.20 (3H, s); 1.58-1.65 (6H, m); 1.19 (3H, t).

Compound No. 120: N-(2-Allyloxyimino-1,1-dimethyl-ethyl)-2-(3-ethynyl-quinolin-6-yloxy)-2-methylsulfanyl-acetamide $^1$H NMR (CDCl$_3$) δ ppm: 8.85 (1H, d); 8.21 (1H, d); 8.07 (1H, d); 7.62 (1H, s br); 7.44-7.47 (1H, d, d); 7.22, (1H, d); 5.94-6.03 (1H, m); 5.64 (1H, s); 5.22-5.34 (2H, m); 4.57 (2H, d); 3.29 (1H, s); 2.19 (3H, s); 1.61 (3H, s); 1.58 (3H, s).

Compound No. 121: 2-(3-Bromo-quinolin-6-yloxy)-N-{2-[(E or Z)-methoxyimino]-1,1-dimethyl-3-phenyl-propyl}-2-methylsulfanyl-acetamide $^1$H NMR (CDCl$_3$) δ ppm: 8.82 (1H, d); 8.24 (2H, m); 8.07 (1H, d); 7.44-7.47 (1H, d, d); 7.24-7.27 (1H, m); 7.13-7.20, (4H, m); 5.60 (1H, s); 3.95 (3H, s); 3.72-3.81 (2H, m); 2.19 (3H, s); 1.58 (3H, s); 1.55 (3H, s).

Compound No. 122: 2-(3-Bromo-quinolin-6-yloxy)-N-{2-[(E or Z)-ethoxyimino]-1,1-dimethyl-3-phenyl-propyl}-2-methylsulfanyl-acetamide ¹H NMR (CDCl₃) δ ppm: 8.82 (1H, d); 8.31 (1H s br); 8.24 (1H, d); 8.06 (1H, d); 7.43-7.46 (1H, d, d); 7.26 (1H, m); 7.15-7.23, (4H, m); 5.60 (1H, s); 4.15-4.23 (2H, m); 3.73-3.82 (2H, m); 2.19 (3H, s); 1.58 (3H, s); 1.56 (3H, s); 1.28 (3H, t).

Compound No. 123: N-{2-[(E or Z)-Allyloxyimino]-1,1-dimethyl-3-phenyl-propyl}-2-(3-bromo-quinolin-6-yloxy-2-methylsulfanyl-acetamide ¹H NMR (CDCl₃) δ ppm: 8.82 (1H, d); 8.23 (1H s br); 8.23 (1H, d); 8.06 (1H, d); 7.43-7.46 (1H, d, d); 7.15-7.26, (5H, m); 5.93-6.03 (1H, m); 5.58 (1H, s); 5.18-5.28 (2H, m); 4.64 (2H, d); 3.75-3.84 (2H, m); 2.19 (3H, s); 1.59 (3H, s); 1.56 (3H, s).

Compound No. 124: 2-(3-Bromo-quinolin-6-yloxy)-N-{2-[(E or Z)-methoxyimino]-1,1-dimethyl-3-thiophen-3-yl-propyl}-2-methylsulfanyl-acetamide ¹H NMR (CDCl₃) δ ppm: 8.82 (1H, d); 8.23 (1H, d); 8.20 (1H s br); 8.06 (1H, d); 7.44-7.47 (1H, d, d); 7.16-7.22, (2H, m); 6.91-6.96 (2H, m); 5.61 (1H, s); 3.96 (3H, s); 3.66-3.74 (2H, m); 2.19 (3H, s); 1.60 (3H, s); 1.57 (3H, s).

Compound No. 125: 2-(3-Bromo-quinolin-6-yloxy)-N-{2-[(E or Z)-ethoxyimino]-1,1-dimethyl-3-thiophen-3-yl-propyl}-2-methylsulfanyl-acetamide ¹H NMR (CDCl₃) δ ppm: 8.82 (1H, d); 8.27 (1H s br); 8.23 (1H, d); 8.03-8.06 (1H, d); 7.43-7.46 (1H, d, d); 7.21 (1H, m); 7.17 (1H, d); 6.93-6.98 (2H, m); 5.61 (1H, s); 4.16-4.24 (2H, m); 3.66-3.75 (2H, m); 2.19 (3H, s); 1.60 (3H, s); 1.57 (3H, s); 1.32 (3H, t).

Compound No. 126: N-{2-[(E or Z)-Allyloxyimino]-1,1-dimethyl-3-thiophen-3-yl-propyl}-2-(3-bromo-quinolin-6-yloxy)-2-methylsulfanyl-acetamide ¹H NMR (CDCl₃) δ ppm: 8.82 (1H, d); 8.23 (1H, d); 8.18 (1H s br); 8.03-8.06 (1H, d); 7.43-7.46 (1H, d, d); 7.21 (1H, m); 7.17 (1H, d); 6.94-6.99 (2H, m); 5.95-6.04 (1H, m); 5.59 (1H, s); 5.20-5.31 (2H, m); 4.65 (2H, d); 3.69-3.77 (2H, m); 2.18 (3H, s); 1.60 (3H, s); 1.58 (3H, s).

Compound No. 127: 2-(3-Bromo-quinolin-6-yloxy)-N-{2-[(E or Z)-methoxyimino]-1,1-dimethyl-3-pyridin-2-yl-propyl}-2-methylsulfanyl-acetamide ¹H NMR (CDCl₃) δ ppm: 9.37 (1H, s); 8.79 (1H, d); 8.48 (1H, d); 8.20 (1H, d); 7.93 (1H, d); 7.60-7.64, (1H, m); 7.22-7.30 (2H, m); 7.13-7.22 (2H, m); 5.59 (1H, s); 3.68-3.83 (5H, m); 2.25 (3H, s); 1.70 (3H, s); 1.64 (3H, s).

Compound No. 128: 2-(3-Bromo-quinolin-6-yloxy)-N-{2-[(E or Z)-ethoxyimino]-1,1-dimethyl-3-pyridin-2-yl-propyl}-2-methylsulfanyl-acetamide ¹H NMR (CDCl₃) δ ppm: 9.39 (1H, s); 8.79 (1H, d); 8.48 (1H, d); 8.20 (1H, d); 7.93 (1H, d); 7.59-7.63, (1H, m); 7.23-7.30 (2H, m); 7.13-7.15 (2H, m); 5.60 (1H, s); 3.99-4.08 (2H, q); 3.68-3.83 (2H, m); 2.25 (3H, s); 1.71 (3H, s); 1.64 (3H, s); 1.11 (3H, t).

Compound No. 129: N-{2-[(E or Z)-Allyloxyimino]-1,1-dimethyl-3-pyridin-2-yl-propyl}-2-(3-bromo-quinolin-6-yloxy)-2-methylsulfanyl-acetamide ¹H NMR (CDCl₃) δ ppm: 9.40 (1H, s); 8.79 (1H, d); 8.48 (1H, d); 8.20 (1H, d); 7.93 (1H, d); 7.59-7.64, (1H, m); 7.24-7.29 (2H, m); 7.13-7.16 (2H, m); 5.74-5.84 (1H, m); 5.59 (1H, s); 5.05-5.10 (2H, m); 4.47 (2H, d); 3.69-3.85 (2H, m); 2.25 (3H, s); 1.71 (3H, s); 1.64 (3H, s).

Compound No. 130: 2-(3-Bromo-quinolin-6-yloxy)-N-{2-[(E or Z)-methoxyimino]-1,1-dimethyl-2-phenyl-ethyl}-2-methylsulfanyl-acetamide ¹H NMR (CDCl₃) δ ppm: 8.83 (1H, d); 8.29 (1H, s br); 8.25 (1H, d); 8.05 (1H, d); 7.40-7.49 (4H, m); 7.18, (1H, d); 7.12-7.15 (2H, m); 5.66 (1H, s); 3.85 (3H, s); 2.21 (3H, s); 1.65 (3H, s); 1.62 (3H, s);

Compound No. 131: 2-(3-Ethynyl-quinolin-6-yloxy)-N-(2-methoxyimino-1,1-dimethyl-ethyl)-butyramide ¹H NMR (CDCl₃) δ ppm: 8.82 (1H, d); 8.15 (1H, d); 8.04 (1H, d); 7.45 (1H, d, d); 7.30 (1H, s); 7.20 (1H, s br); 7.05 (1H, d); 4.59 (1H, m); 3.76 (3H, s); 3.28 (1H, s); 2.06, (2H, m); 1.49 (3H, s); 1.44 (3H, s) 1.08 (3H, t).

Compound No. 132: 2-(3-Ethynyl-8-methyl-quinolin-6-yloxy)-N-(2-methoxyimino-1,1-dimethyl-ethyl)-butyramide ¹H NMR (CDCl₃) δ ppm: 8.83 (1H, d); 8.12 (1H, d); 7.31 (2H, m); 7.18 (1H, s br); 6.88 (1H, d); 4.58 (1H, m); 3.77 (3H, s); 3.27 (1H, s); 2.77 (3H, s); 2.02, (2H, m); 1.49 (3H, s); 1.43 (3H, s); 1.07 (3H, t).

Compound No. 133: 2-(3-Bromo-8-ethyl-quinolin-6-yloxy)-N-(2-methoxyimino-1,1-dimethyl-ethyl)-2-methylsulfanyl-acetamide ¹H NMR (CDCl₃) δ ppm: 8.80 (1H, d); 8.21 (1H, d); 7.62 (1H, s br); 7.41 (1H, s); 7.32 (1H, d); 7.0 (1H, d); 5.63 (1H, s); 3.88 (3H, s); 3.24 (2H, q); 2.20 (3H, s); 1.61 (3H, s); 1.58 (3H, s); 1.37 (3H, t).

Compound No. 134: 2-(3-Ethynyl-7-fluoro-quinolin-6-yloxy)-N-(2-methoxyimino-1,1-dimethyl-ethyl)-butyramide ¹H NMR (CDCl₃) δ ppm: 8.84 (1H, d); 8.15 (1H, d); 7.77 (1H, d); 7.37 (1H, s br); 7.30 (1H, s); 7.12 (1H, d); 4.66 (1H, t); 3.80, 3.28 (4H, m); 2.10 (2H, m); 1.51 (3H, s); 1.46 (3H, s); 1.09 (3H, t).

Compound No. 135: N-2-Ethoxyimino-1,1-dimethyl-ethyl)-2-(3-ethynyl-8-methyl-quinolin-6-yloxy)-butyramide ¹H NMR (CDCl₃) δ ppm: 8.82 (1H, d); 8.11 (1H, d); 7.27-7.31 (3H, m); 6.88 (1H, d); 4.57 (1H, m); 3.90-4.05 (2H, m); 3.27 (1H, s); 2.76 (3H, s); 1.97-2.10 (2H, m); 1.50 (3H, s); 1.43 (3H, s); 1.17 (3H, t); 1.08 (3H, t). MP 105-107° C.

Compound No. 136: 2-(3-Ethynyl-8-methyl-quinolin-6-yloxy)-N-(2-isobutoxyimino-1,1-dimethyl-ethyl)-butyramide $^1$H NMR (CDCl$_3$) δ ppm: 8.88 (1H, d); 8.19 (1H, d); 7.21-7.33 (3H, m); 6.91 (1H, d); 4.57 (1H, m); 3.66-3.74 (2H, m); 3.30 (1H, s); 2.81 (3H, s); 1.97-2.10 (2H, m); 1.81-1.90 (1H, m); 1.50 (3H, s); 1.44 (3H, s); 1.08 (3H, t); 0.85-0.87 (6H, m).

Compound No. 137: N-(2-tert-Butoxyimino-1,1-dimethyl-ethyl)-2-(3-ethynyl-8-methyl-quinolin-6-yloxy)-butyramide $^1$H NMR (CDCl$_3$) δ ppm: 8.85 (1H, d); 8.15 (1H, d); 7.52 (1H, s); 7.33 (1H, d); 7.18 (1H, s); 6.88 (1H, d); 4.57 (1H, m); 3.28 (1H, s); 2.77 (3H, s); 2.01-2.08 (2H, m); 1.52 (3H, s); 1.43 (3H, s); 1.16 (9H, s); 1.08 (3H, t). MP 130-132° C.

Compound No. 138: N-(2-Allyloxyimino-1,1-dimethyl-ethyl)-2-(3-ethynyl-8-methyl-quinolin-6-yloxy)-butyramide $^1$H NMR (CDCl$_3$) δ ppm: 8.88 (1H, d); 8.20 (1H, d); 7.34 (2H, m); 7.21 (1H, s); 6.90 (1H, d); 5.84-5.93 (1H, m); 5.12-5.26 (2H, m); 4.57 (1H, m); 4.44 (2H, m); 3.30 (1H, s); 2.82 (3H, s); 1.97-2.10 (2H, m); 1.50 (3H, s); 1.44 (3H, s); 1.07 (3H, t). MP 81-84° C.

Compound No. 139: 2-(3-Ethynyl-8-methyl-quinolin-6-yloxy)-N-(2-hydroxyimino-1,1-dimethyl-ethyl)-butyramide $^1$H NMR (DMSO-d$_6$) δ ppm: 10.55 (1H, s); 8.76 (1H, d); 8.34 (1H, d); 8.09 (1H, s); 7.39 (1H, s); 7.37 (1H, d); 7.08 (1H, d); 4.65 (1H, t); 4.50 (1H, s); 2.66 (3H, s); 1.87 (2H, m); 1.37 (3H, s); 1.36 (3H, s); 0.97 (3H, t). MP 134-135° C.

Compound No. 140: 2-(3-Bromo-quinolin-6-yloxy)-N-(2-cyanomethoxyimino-1,1-dimethyl-ethyl)-2-methylsulfanyl-acetamide $^1$H NMR (CDCl$_3$) δ ppm: 8.81 (1H,); 8.25 (1H, d); 8.05 (1H, d); 7.64 (1H, s); 7.50, (1H, dd); 7.25 (1H, s); 7.21 (1H, d); 5.64 (1H, s); 4.68 (2H, s); 2.18 (3H, s); 1.61 (3H, s); 1.60 (3H, s).

Compound No. 141: 2-(3-Bromo-quinolin-6-yloxy)-N-(2-but-2-ynyloxyimino-1,1-dimethyl-ethyl)-2-methylsulfanyl-acetamide $^1$H NMR (CDCl$_3$) δ ppm: 8.74 (1H, d); 8.20 (1H, d); 7.98 (1H, d); 7.62 (1H, s, br); 7.45 (1H, dd); 7.39 (1H, s); 7.13 (1H, d); 5.57 (1H, s); 4.58 (2H, q); 2.12 (3H, s); 1.79 (3H, t); 1.55 (3H, s); 1.52 (3H, s).

Compound No. 142: 2-(3-Bromo-quinolin-6-yloxy)-N-[2-(2-fluoro-ethoxyimino)-1,1-dimethyl-ethyl]-2-methylsulfanyl-acetamide $^1$H NMR (CDCl$_3$) δ ppm: 8.82 (1H, d); 8.25 (1H, d); 8.07 (1H, d); 7.51 (1H, s); 7.43-7.47, (2H, m); 7.18 (1H, d); 5.64 (1H, s); 4.70 (1H, m); 4.58 (1H, m); 4.34 (1H, m); 4.28 (1H, m); 2.19 (3H, s); 1.61 (3H, s); 1.59 (3H, s).

Compound No. 143: 2-(3-Bromo-quinolin-6-yloxy)-N-[1,1-dimethyl-2-(tetrahydro-furan-2-ylmethoxyimino)-ethyl]-2-methylsulfanyl-acetamide $^1$H NMR (CDCl$_3$) δ ppm: 8.81 (1H, d); 8.26 (1H, d); 8.07 (1H, d); 7.59 (1H, s, br); 7.45, (2H, m); 7.18 (1H, d); 5.62 (1H, s); 4.01-4.19 (3H, m); 3.74-3.91 (2H, m); 2.17 (3H, s); 1.85-2.03 (3H, m); 1.60-1.67 (1H, m); 1.59 (3H, s); 1.56 (3H, s).

Compound No. 144: 2-(3-Bromo-quinolin-6-yloxy)-N-(2-methoxyimino-1,1-dimethyl-ethyl)-butyramide $^1$H NMR (CDCl$_3$) δ ppm: 8.80 (1H, d); 8.22 (1H, d); 8.06 (1H, d); 7.47 (1H, dd); 7.32, (1H, s); 7.20 (1H, s, br); 7.03 (1H, d); 4.60 (1H, m); 3.78 (3H, s); 2.0-2.13 (2H, m); 1.51 (3H, s); 1.46 (3H, s); 1.10 (3H, t). MP 90-93° C.

Compound No. 145: 2-(3-Bromo-8-methyl-quinolin-6-yloxy)-N-(2-methoxyimino-1,1-dimethyl-ethyl)-butyramide $^1$H NMR (CDCl$_3$) δ ppm: 8.81 (1H, d); 8.18 (1H, d); 7.33 (2H, s, br); 7.18 (1H, s, br); 6.87 (1H, d); 4.59 (1H, m); 3.79 (3H, s); 2.78 (3H, s); 1.99-2.11 (2H, m); 1.51 (3H, s); 1.46 (3H, s); 1.09 (3H, t). MP 87-89° C.

Compound No. 146: 2-(3-Bromo-8-chloro-quinolin-6-yloxy)-N-(2-methoxyimino-1,1-dimethyl-ethyl)-butyramide $^1$H NMR (CDCl$_3$) δ ppm: 8.92 (1H, d); 8.24 (1H, d); 7.64 (1H, d); 7.30 (1H, s); 7.21 (1H, s, br); 6.97 (1H, d); 4.59 (1H, m); 3.80 (3H, s); 2.01-2.13 (2H, m); 1.52 (3H, s); 1.46 (3H, s); 1.10 (3H, t). MP 104-110° C.

Compound No. 147: 2-(3-Ethynyl-quinolin-6-yloxy)-N-(2-hydroxyimino-1,1-dimethyl-ethyl)-butyramide $^1$H NMR (DMSO-d$_6$) δ ppm: 10.56 (1H, s); 8.75 (1H, d); 8.40 (1H, d); 8.13 (1H, s); 7.95 (1H, d); 7.50 (1H, m); 7.40 (1H, s); 7.26 (1H, d); 4.70 (1H, t); 4.52 (1H, s); 1.86-1.94 (2H, m); 1.37 (6H, s); 0.99 (3H, t). MP 59-61° C.

Compound No. 148: N-(2-Ethoxyimino-1,1-dimethyl-ethyl)-2-(3-ethynyl-quinolin-6-yloxy)-butyramide $^1$H NMR (DMSO-d$_6$) δ ppm: 8.75 (1H, d); 8.39 (1H, d); 8.20 (1H, s); 7.95 (1H, d); 7.49 (1H, m); 7.46 (1H, s); 7.25 (1H, d); 4.68 (1H, t); 4.52 (1H, s); 3.90 (2H, q); 1.90 (2H, m); 1.36 (6H, s); 1.09 (3H, t); 1.00 (3H, t). MP 84-85° C.

Compound No. 149: N-(2-Allyloxyimino-1,1-dimethyl-ethyl)-2-(3-ethynyl-quinolin-6-yloxy)-butyramide $^1$H NMR (DMSO-d$_6$) δ ppm: 8.75 (1H, d); 8.39 (1H, d); 8.22 (1H, s); 7.95 (1H, d); 7.52 (1H, s); 7.49 (1H, m); 7.25 (1H, d); 5.82-5.92 (1H, m); 5.11-5.23 (2H, m); 4.68 (1H, t); 4.52 (1H, s); 4.40 (2H, m); 1.90 (2H, m); 1.36 (6H, s); 1.00 (3H, t). MP 84-86° C.

Compound No. 150: 2-(3-Bromo-quinolin-6-yloxy)-N-(2-hydroxyimino-1,1-dimethyl-ethyl)-butyramide $^1$H NMR (DMSO-d$_6$) δ ppm: 10.55 (1H, s); 8.79 (1H, d); 8.58 (1H, d); 8.12 (1H, s); 7.97 (1H, d); 7.50 (1H, m); 7.40 (1H, s); 7.24 (1H, d); 4.67 (1H, t); 1.89 (2H, m); 1.37 (6H, s); 0.99 (3H, t).) MP 156-157° C.

Compound No. 151: 2-(3-Bromo-quinolin-6-yloxy)-N-[2-(2-fluoro-ethoxyimino)-1,1-dimethyl-ethyl]-butyramide MP $^1$H NMR (CDCl$_3$) δ ppm: 8.81 (1H, d); 8.22 (1H, d); 8.06 (1H, d); 7.43-7.46 (2H, m); 7.09 (1H, s, br); 7.02 (1H, d); 4.52-4.65 (2H, m); 4.44-4.53 (1H, m); 4.11-4.27 (2H, m); 2.01-2.12 (2H, m); 1.52 (3H, s); 1.47 (3H, s); 1.10 (3H, t). 108-112° C.

Compound No. 152: N-(2-Hydroxyimino-1,1-dimethyl-ethyl)-2-(3-iodo-quinolin-6-yloxy)-butyramide $^1$H NMR (DMSO-d$_6$) δ ppm: 10.56 (1H, s); 8.88 (1H, d); 8.70 (1H, d); 8.10 (1H, s); 7.91 (1H, d); 7.48 (1H, m); 7.40 (1H, d); 7.20 (1H, d); 4.66 (1H, t); 1.89 (2H, m); 1.37 (6H, s); 0.98 (3H, t) mp 157-160° C.

Compound No. 153: N-(2-Hydroxyimino-1,1-dimethyl-ethyl)-2-(3-iodo-quinolin-6-yloxy)-2-methyl-sulfanyl-acetamide $^1$H NMR (DMSO-d$_6$) δ ppm: 10.65 (1H, s); 8.92 (1H, d); 8.76 (1H, d); 8.17 (1H, s); 7.95 (1H, m); 7.58 (1H, m); 7.46 (1H, d); 7.38 (1H, s); 5.94 (1H, s); 2.14 (3H, s); 1.43 (6H, s). MP 194-196° C.

Compound No. 154: 2-(3-Bromo-7-fluoro-quinolin-6-yloxy)-N-(2-methoxyimino-1,1-dimethyl-ethyl)-butyramide $^1$H NMR (CDCl$_3$) δ ppm: 8.80 (1H, d); 8.18 (1H, d); 7.74 (1H, d); 7.36 (1H, s, br); 7.31 (1H, s); 7.08 (1H, d); 4.65 (1H, t); 3.80 (3H, s); 2.05-2.14 (2H, m); 1.51 (3H, s); 1.46 (3H, s); 1.09 (3H, t).

Compound No. 155: N-[2-(2-Fluoro-ethoxyimino)-1,1-dimethyl-ethyl]-2-(3-iodo-quinolin-6-yloxy)-butyramide $^1$H NMR (CDCl$_3$) δ ppm: 8.95 (1H, s); 8.51 (1H, s); 8.10 (1H, d); 7.49 (1H, d); 7.42 (1H, s); 7.08 (1H, s); 7.01 (1H, s); 4.45-4.67 (3H, m); 4.15-4.25 (2H, m); 2.0-2.12 (2H, m); 1.51 (3H, s); 1.48 (3H, s); 1.09 (3H, t). MP 83-84° C.

EXAMPLE 21

This Example illustrates the fungicidal properties of compounds of formula (I).

Compounds were tested as aqueous suspensions against a set of our standard screening pathosystems. Preventative tests were performed with 1 or 2 day preventive application, i.e. plants were treated with the compounds 1-2 days prior to artificial inoculation with fungal spores whereas for curative tests the inoculation with fungal spore was done 1 or 2 days before application. Application was done at 500 l/ha in an application device providing coverage of upper and lower leaf sides (turntable, air supported spraying from 2 nozzles).

A single evaluation of disease control was done 4 to 20 days after inoculation, depending on the pathosystem.

Compounds were tested as aqueous suspensions against a set of standard screening pathosystems as exemplified below.

Foliar application was done at 500 l/ha in an application device providing coverage of upper and lower leaf sides (turntable, air supported spraying from 2 nozzles). Preventative tests were performed with 1 or 2 day preventive application, i.e. plants were treated with the compounds 1-2 days prior to artificial inoculation with fungal spores whereas for curative tests the inoculation with fungal spore was done 1 or 2 days before application. A single evaluation of disease control was done 4 to 20 days after inoculation, depending on the pathosystem.

Leaf Disc Tests:

Leaf disks of various plant species (diameter 14 mm) are cut from plants grown in the greenhouse. The cut leaf disks are placed in multiwell plates (24-well format) onto water agar. Immediately after cutting the leaf disks are sprayed with a test solution.

Compounds to be tested are prepared as DMSO solutions (max. 10 mg/ml). Just before spraying the solutions are diluted to the appropriate concentrations with 0.025% Tween20. After drying, the leaf disks are inoculated with a spore suspension of the appropriate pathogenic fungus.

After an incubation time of 3-7 days after inoculation at defined conditions (temp, rH, light, etc.) according to the respective test system, the activity of the test compound is assessed as antifungal activity.

Liquid Culture Tests:

Mycelia fragments or conidia suspensions of a fungus, prepared either freshly from liquid cultures of the fungus or from cryogenic storage, are directly mixed into nutrient broth. DMSO solutions of the test compound (max. 10 mg/ml) is diluted with 0.025% Tween20 by factor 50 and 10 µl of this solution is pipetted into a microtiter plate (96-well format) and the nutrient broth containing the fungal spores/mycelia fragments is then added to give an end concentration of the tested compound. The test plates are incubated at 24° C. and 96% rH in the dark. The inhibition of fungal growth is determined photometrically after 2-6 days and antifungal activity is calculated.

Plant Tests:

*Alternaria solani*/tomato/preventive (*Alternaria* on tomato): 4 weeks old tomato plants cv. Roter Gnom were treated with the formulated test compound in a spray chamber. Two days after application tomato plants were inoculated by spraying a spore suspension on the test plants. After an incubation period of 4 days at 22/18° C. and 95% r.h. in a greenhouse the percentage leaf area covered by disease was assessed.

*Botrytis cinerea*/tomato/preventive (*Botrytis* on tomato): 4 weeks old tomato plants cv. Roter Gnom were treated with the formulated test compound in a spray chamber. Two days after application tomato plants were inoculated by spraying a spore suspension on the test plants. After an incubation period of 3 days at 20° C. and 95% r.h. in a greenhouse the percentage leaf area covered by disease was assessed.

*Botrytis cinerea*/grape/preventive (*Botrytis* on grape): 5 weeks old grape seedlings cv. Gutedel were treated with the formulated test compound in a spray chamber. Two days after application grape plants were inoculated by spraying a spore suspension on the test plants. After an incubation period of 3 days at 20° C. and 95% r.h. in a greenhouse the percentage leaf area covered by disease was assessed.

*Blumeria* (*Erysiphe*) *graminis*/barley/preventive (Powdery mildew on barley): 1-week-old barley plants cv. Regina were treated with the formulated test compound in a spray chamber. Two days after application barley plants were inoculated by shaking powdery mildew infected plants above the test plants. After an incubation period of 6 days at 20° C./18° C. (day/night) and 60% r.h. in a greenhouse the percentage leaf area covered by disease was assessed.

*Blumeria (Erysiphe) graminis*/wheat/preventive (Powdery mildew on wheat): 1 week old wheat plants cv. *Arina* were treated with the formulated test compound in a spray chamber. Two days after application wheat plants were inoculated by spreading mildew spores over the test plants in an inoculation chamber. After an incubation period of 6 days at 20° C./18° C. (day/night) and 60% r.h. in a greenhouse the percentage leaf area covered by disease was assessed.

*Blumeria (Erysiphe) graminis*/wheat/curative (Powdery mildew on wheat): Two days before application 1-week-old wheat plants cv. *Arina* were inoculated by spreading mildew spores over the test plants in an inoculation chamber. The inoculated plants were treated with the formulated test compound in a spray chamber. After an incubation period of 6 days at 20° C./18° C. (day/night) and 60% r.h. in a greenhouse the percentage leaf area covered by disease was assessed.

*Glomerella lagenarium (Colletotrichum lagenarium)*/cucumber/preventive: 1 week old cucumber plants cv. Wisconsin were treated with the formulated test compound in a spray chamber. One day after application wheat plants were inoculated by spraying a spore suspension (1×105 spores/ml) on the test plants. After an incubation period of 30 h in darkness at 23° C. and 100% r.h. plants were kept for 6 days 23° C./21° C. (day/night) and 70% r.h. in a greenhouse. The percentage leaf area covered by disease was assessed 7 days after inoculation.

*Phytophthora infestans*/tomato/preventive (late blight on tomato): 3 weeks old tomato plants cv. Roter Gnom were treated with the formulated test compound in a spray chamber. Two days after application the plants were inoculated by spraying a sporangia suspension on the test plants. After an incubation period of 4 days at 18° C. and 100% r.h. in a growth chamber the percentage leaf area covered by disease was assessed.

*Phytophthora infestans*/tomato/curative (late blight on tomato): One day before application 3-week-old tomato plants cv. Roter Gnom were inoculated by spraying a sporangia suspension on the test plants. The inoculated plants were treated with the formulated test compound in a spray chamber. After an incubation period of 4 days at 18° C. and 100% r.h. in a growth chamber the percentage leaf area covered by disease was assessed.

*Phytophthora infestans*/tomato/long lasting (late blight on tomato): 3 weeks old tomato plants cv. Roter Gnom were treated with the formulated test compound in a spray chamber. 6 days after application the plants were inoculated by spraying a sporangia suspension on the test plants. After an incubation period of 4 days at 18° C. and 100% r. h. in a growth chamber the percentage leaf area covered by disease was assessed.

*Phytophthora infestans*/potato/preventive (late blight on potato): 2 weeks old potato plants cv. Bintje were treated with the formulated test compound in a spray chamber. Two days after application the plants were inoculated by spraying a sporangia suspension on the test plants. After an incubation period of 4 days at 18° C. and 100% r. h. in a growth chamber the percentage leaf area covered by disease was assessed.

*Phytophthora infestans*/potato/curative (late blight on potato): One day before application 2 weeks old potato plants cv. Bintje were inoculated by spraying a sporangia suspension on the test plants. The inoculated plants were treated with the formulated test compound in a spray chamber. After an incubation period of 4 days at 18° C. and 100% r.h. in a growth chamber the percentage leaf area covered by disease was assessed.

*Phytophthora infestans*/potato/long lasting (late blight on potato): 2 weeks old potato plants cv. Bintje were treated with the formulated test compound in a spray chamber.

6 days after application the plants were inoculated by spraying a sporangia suspension on the test plants. After an incubation period of 4 days at 18° C. and 100% r.h. in a growth chamber the percentage leaf area covered by disease was assessed.

*Plasmopara viticola*/grape/preventive (Grape downy mildew): 5 weeks old grape seedlings cv. Gutedel were treated with the formulated test compound in a spray chamber. One day after application grape plants were inoculated by spraying a sporangia suspension on the lower leaf side of the test plants. After an incubation period of 6 days at 22° C. and 100% r.h. in a greenhouse the percentage leaf area covered by disease was assessed.

*Plasmopara viticola*/grape/curative (Grape downy mildew): One day before application 5-week-old grape seedlings cv. Gutedel were inoculated by spraying a sporangia suspension on the lower leaf side of the test plants. The inoculated grape plants were treated with the formulated test compound in a spray chamber. After an incubation period of 6 days at 22° C. and 100% r.h. in a greenhouse the percentage leaf area covered by disease was assessed.

*Plasmopara viticola*/grape/long lasting (Grape downy mildew): 5 weeks old grape seedlings cv. Gutedel were treated with the formulated test compound in a spray chamber. 6 days after application grape plants were inoculated by spraying a sporangia suspension on the lower leaf side of the test plants. After an incubation period of 6 days at 22° C. and 100% r.h. in a greenhouse the percentage leaf area covered by disease was assessed.

*Podosphaera leucotricha*/apple/preventive (Powdery mildew on apple): 5 weeks old apple seedlings cv. McIntosh were treated with the formulated test compound in a spray chamber. One day after application apple plants were inoculated by shaking plants infected with apple powdery mildew above the test plants. After an incubation period of 7 days at 22° C. and 60% r.h. under a light regime of 14/10 h (light/dark) the percentage leaf area covered by disease was assessed.

*Puccinia recondita*/wheat/preventive (Brown rust on wheat): 1 week old wheat plants cv. *Arina* were treated with the formulated test compound in a spray chamber. One day after application wheat plants were inoculated by spraying a spore suspension (1×105 uredospores/ml) on the test plants. After an incubation period of 1 day at 20° C. and 95% r.h. plants were kept for 10 days 20° C./18° C. (day/night) and 60% r.h. in a greenhouse. The percentage leaf area covered by disease was assessed 11 days after inoculation.

*Puccinia recondita*/wheat/curative (Brown rust on wheat): Two days before application 1-week-old wheat plants cv. *Arina* were inoculated by spraying a spore suspension (1×105 uredospores/ml) on the test plants. After an incubation period of 1 day at 20° C. and 95% r.h. and for 1 day at 20° C. and 60% r.h. in a greenhouse, the inoculated plants were treated with the formulated test compound in a spray chamber. After an additional incubation period of 8 days at 20° C./18° C. (day/night) and 60% r.h. in a greenhouse the percentage leaf area covered by disease was assessed.

*Puccinia recondita*/wheat/long lasting (Brown rust on wheat): 1 week old wheat plants cv. *Arina* were treated with the formulated test compound in a spray chamber.

8 days after application wheat plants were inoculated by spraying a spore suspension (1×105 uredospores/ml) on the test plants. After an incubation period of 1 day at 20° C. and 95% r.h. plants were kept for 10 days at 20° C. and 60% r.h. in a greenhouse. The percentage leaf area covered by disease was assessed 11 days after inoculation.

*Magnaporthe grisea* (*Pyricularia oryzae*)/rice/preventive (Rice Blast): 3 weeks old rice plants cv. Koshihikari were treated with the formulated test compound in a spray chamber. Two days after application rice plants were inoculated by spraying a spore suspension (1×105 conidia/ml) on the test plants. After an incubation period of 6 days at 25° C. and 95% r.h. the percentage leaf area covered by disease was assessed.

*Mycosphaerella arachidis* (*Cercospora arachidicola*)/peanut/preventive: 3 week old peanut plants cv. Georgia Green were treated with the formulated test compound in a spray chamber. One day after application plants were inoculated by spraying a spore suspension (350 000 spores/ml) on the lower leaf surface. After an incubation period of 4 days under plastic hood at 23° C. and 100% r.h. plants were kept at 23° C./20° C. (day/night) and 70% r.h. in a greenhouse. The percentage leaf area covered by disease was assessed 11-12 days after inoculation.

*Mycosphaerella arachidis* (*Cercospora arachidicola*)/peanut/curative: 3 week old peanut plants cv. Georgia Green were inoculated by spraying a spore suspension (350 000 spores/ml) on the lower leaf surface. After an incubation period of 1 day at 23° C. and 100% r.h. the inoculated plants were treated with the formulated test compound in a spray chamber. After an incubation period of 3 days under plastic hood at 23° C. and 100% r.h. plants were kept at 23° C./20° C. (day/night) and 70% r.h. in a greenhouse. The percentage leaf area covered by disease was assessed 11-12 days after inoculation.

*Pyrenophora teres* (*Helminthosporium teres*)/barley/preventive (Net blotch on barley): 1-week-old barley plants cv. Regina were treated with the formulated test compound in a spray chamber. Two days after application barley plants were inoculated by spraying a spore suspension (2.6×104 conidia/ml) on the test plants. After an incubation period of 4 days at 20° C. and 95% r.h. the percentage leaf area covered by disease was assessed.

*Septoria tritici*/wheat/preventive (*Septoria* leaf spot on wheat): 2 week old wheat plants cv. Riband were treated with the formulated test compound in a spray chamber. One day after application wheat plants were inoculated by spraying a spore suspension (106 conidia/ml) on the test plants. After an incubation period of 1 day at 22° C./21° C. and 95% r.h. plants were kept at 22° C./21° C. and 70% r.h. in a greenhouse. The percentage leaf area covered by disease was assessed 16-18 days after inoculation.

*Uncinula necator*/grape/preventive (Powdery mildew on grape): 5 weeks old grape seedlings cv. Gutedel were treated with the formulated test compound in a spray chamber. One day after application grape plants were inoculated by shaking plants infected with grape powdery mildew above the test plants. After an incubation period of 7 days at 24/22° C. and 70% r.h. under a light regime of 14/10 h (light/dark) the percentage leaf area covered by disease was assessed.

*Venturia inaequalis*/apple/preventive (Scab on apple): 3 weeks old apple seedlings cv. McIntosh were treated with the formulated test compound in a spray chamber. One day after application apple plants were inoculated by spraying a spore suspension (3.5×105 conidia/ml) on the test plants. After an incubation period of 4 days at 20° C. and 95% r.h. the plants are placed at 20° C./19° C. and 60% r.h. in a greenhouse. 11 days after inoculation the percentage leaf area covered by disease was assessed. *Venturia inaequalis*/apple/curative (Scab on apple): Two days before application 3 weeks old apple seedlings cv. McIntosh were inoculated by spraying a spore suspension (3.5×105 conidia/ml) on the test plants. After an incubation period of 2 days at 20° C. and 95% r.h. the plants were treated with the formulated test compound in a spray chamber. The apple plants were kept at 20° C./19° C. and 60% r.h. in a greenhouse. 11 days after inoculation the percentage leaf area covered by disease was assessed.

Screening Methods Soil Drench Application:

*Blumeria* (*Erysiphe*) *graminis*/wheat/soil drench (Powdery mildew on wheat):

Each pot (soil volume: 40 ml) with 1 week old wheat plants cv. *Arina* were poured with 4 ml compound solution. 4 days after application wheat plants were inoculated by spreading mildew spores over the test plants in an inoculation chamber. After an incubation period of 6 days at 200° C./18° C. (day/night) and 60% r.h. in a greenhouse the percentage leaf area covered by disease was assessed.

*Phytophthora infestans*/tomato/soil drench (late blight on tomato): Each pot (soil volume: 40 ml) with 3 weeks old tomato plants cv. Roter Gnom were poured with 4 ml compound solution. 4 days after application the plants were inoculated by spraying a sporangia suspension on the test plants. After an incubation period of 4 days at 18° C. and 100% r.h. in a growth chamber the percentage leaf area covered by disease was assessed.

*Phytophthora infestans*/potato/soil drench (late blight on potato): Each pot (soil volume: 40 ml) with 2 weeks old potato plants cv. Bintje were poured with 4 ml compound solution. 4 days after application the plants were inoculated by spraying a sporangia suspension on the test plants. After an incubation period of 4 days at 18° C. and 100% r.h. in a growth chamber the percentage leaf area covered by disease was assessed.

*Plasmopara viticola*/grape/soil drench (Grape downy mildew): Each pot (soil volume; 40 ml) with 5 weeks old grape seedlings cv. Gutedel were poured with 4 ml compound solution. 3 days after application grape plants were inoculated by spraying a sporangia suspension on the lower leaf side of the test plants. After an incubation period of 6 days at 22° C. and 100% r.h. in a greenhouse the percentage leaf area covered by disease was assessed.

*Puccinia recondita*/wheat/soil drench (Brown rust on wheat): Each pot (soil volume; 40 ml) with 1 week old wheat plants cv. *Arina* were poured with 4 ml compound solution. 3 days after application wheat plants were inoculated by spraying a spore suspension (1×105 uredospores/ml) on the test plants. After an incubation period of 1 day at 20° C. and 95% r.h. plants were kept for 10 days 20° C./18° C. (day/night) and 60% r.h. in a greenhouse. The percentage leaf area covered by disease was assessed 11 days after inoculation.

*Magnaporthe grisea* (*Pyricularia oryzae*)/rice/soil drench (Rice Blast): Each pot (soil volume: 40 ml) with 3 weeks old rice plants cv. Koshihikari were poured with 4 ml compound solution. 4 days after application rice plants were inoculated by spraying a spore suspension (1×105 conidia/ml) on the test plants. After an incubation period of 6 days at 25° C. and 95% r.h. the percentage leaf area covered by disease was assessed.

Screening Methods Seed Treatment Application:

*Pythium ultimum*/cotton (damping-off on cotton): A defined amount of mycelium of *P. ultimum* is mixed with a previously sterilized soil. After application of the formulated seed treatment onto cotton seeds (cv. Sure Grow 747) the seeds are sown 2 cm deep into the infected soil. The trial is incubated at 18° C. until seedlings do emerge. From this time on the trial is kept at 22° C. and 14 h light period. The evaluation is made by assessing the emergence and the number of plants that wilt and die. The following compounds gave at least 15% control of *Pythium ultimum* on cotton seeds: 15, 38, 50, 59, 61, 76, 131.

*Plasmopara halstedii*/sunflower (downy mildew of sunflower): After application of the formulated seed treatments sunflower seeds are sown 1.5 cm deep into sterile soil. The trial is kept at 22° C. with a 14 h light period. After 2 days a spore suspension ($1 \times 10^5$ zoospores/mil) of *Plasmopara halstedii* is pipetted onto the soil surface close to the germinating seeds. After 16 days the trial is incubated under high humidity and the number of infected plants is assessed 2 days later.

With methods described below, the compounds were tested in a leaf disk assay. The test compounds were dissolved in DMSO and diluted into water to 200 ppm. In the case of the test on *Pythium ultimum*, they were dissolved in DMSO and diluted into water to 20 ppm.

*Erysiphe graminis* f.sp. *tritici* (wheat powdery mildew): Wheat leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Puccinia recondita* f.sp. *tritici* (wheat brown rust): Wheat leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed nine days after inoculation as preventive fungicidal activity.

*Septoria nodorum* (wheat glume blotch): Wheat leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Pyrenophora teres* (barley net blotch): Barley leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Pyricularia otyzae* (rice blast): Rice leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Botrytis cinerea* (grey mould): Bean leaf disks were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Phytophthora infestans* (late blight of potato on tomato): Tomato leaf disks were placed on water agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Plasmopara viticola* (downy mildew of grapevine): Grapevine leaf disks were placed on agar in a 24-well plate and sprayed a solution of the test compound. After allowing to dry completely, for between 12 and 24 hours, the leaf disks were inoculated with a spore suspension of the fungus. After appropriate incubation the activity of a compound was assessed seven days after inoculation as preventive fungicidal activity.

*Septoria tritici* (leaf blotch): Conidia of the fungus from cryogenic storage were directly mixed into nutrient broth (PDB potato dextrose broth). After placing a (DMSO) solution of the test compounds into a microtiter plate (96-well format) the nutrient broth containing the fungal spores was added. The test plates were incubated at 24 C and the inhibition of growth was determined photometrically after 72 hrs.

*Fusarium culmorum* (root rot): Conidia of the fungus from cryogenic storage were directly mixed into nutrient broth (PDB potato dextrose broth). After placing a (DMSO) solution of the test compounds into a microtiter plate (96-well format) the nutrient broth containing the fungal spores was added. The test plates were incubated at 24 C and the inhibition of growth was determined photometrically after 48 hrs.

*Pythium ultimum* (Damping off): Mycelial fragments of the fungus, prepared from a fresh liquid culture, were mixed into potato dextrose broth. A solution of the test compound in dimethyl sulphoxide was diluted with water to 20 ppm then placed into a 96-well microtiter plate and the nutrient broth containing the fungal spores was added. The test plate was incubated at 24° C. and the inhibition of growth was determined photometrically after 48 hours.

The following compounds from the above Examples gave at least 60% control of the following fungal infection on the indicated pathogens at 200 ppm:

*Plasmopara viticola*, 1, 2, 3, 4, 5, 8, 13, 14, 15, 17, 18, 19, 23, 28, 29, 31, 32, 33, 36, 37, 38, 40, 41, 42, 44, 45, 46, 47, 49, 50, 51, 52, 53, 54, 55, 56, 57, 58, 59, 61, 62, 63, 64, 65, 66, 68, 69, 70, 71, 72, 73, 74, 75, 76, 77, 78, 79, 80, 81, 82, 83, 84, 89, 90, 91, 92, 93, 94, 95, 96, 98, 99, 101, 102, 103, 104, 106, 108, 109, 111, 112, 113, 114, 115, 116, 117, 118, 119, 120, 121, 122, 125, 126, 127, 130, 131, 132, 133, 134, 135, 138, 139, 140, 141, 142, 143, 144, 145, 146, 147, 148, 151, 152, 153, 154, 155;

*Phytophthora infestans*, compounds 1, 2, 3, 4, 5, 8, 13, 14, 15, 16, 17, 19, 23, 26, 27, 29, 31, 32, 37, 38, 41, 42, 45, 46, 49, 52, 53, 54, 55, 56, 57, 58, 59, 60, 61, 62, 63, 64, 65, 66, 68, 69, 70, 72, 74, 75, 76, 77, 78, 79, 80, 89, 91, 92, 93, 94, 95, 101, 104, 108, 109, 111, 112, 113, 114, 115, 116, 117, 118, 119, 120, 130, 131, 132, 134, 138, 139, 140, 141, 142, 143, 144, 145, 146, 147, 148, 150, 151, 152, 153, 154, 155; *Etysiphe graminis* f.sp. *tritici*, compounds 1, 2, 3, 4, 5, 7, 13, 15, 16, 17, 19, 23, 26, 29, 31, 32, 36, 37, 38, 41, 44, 45, 46, 48, 49, 51, 53, 54, 55, 56, 57, 58, 59, 61, 62, 63, 64, 65, 66, 68, 69, 70, 71, 72, 73, 74, 75, 76, 77, 79, 80, 85, 89, 90, 92, 93, 94, 95, 101, 102, 103, 104, 105, 108, 114, 115, 117, 118, 119, 120, 130, 131, 132, 134, 135, 137, 138, 139, 140, 141, 142, 143, 144, 145, 146, 147, 148, 149, 151, 152, 153, 154, 155; *Botrytis cinerea*, compounds 1, 13, 33, 39, 40, 55, 56, 58, 59, 60, 61, 62, 64, 65, 66, 68, 69, 71, 72, 73, 74, 75, 76, 81, 83, 84, 85, 87, 89, 90, 91, 95, 96, 97, 99, 106, 108, 121, 122, 123, 129, 145, 149; *Pyricularia oryzae*, compounds 2, 15, 16, 27, 31, 45, 116, 117, 118, 119, 120; *Puccinia recondite* f.sp. *tritici*, compounds 5, 32, 55, 56, 57, 59, 61, 62, 64, 65, 66, 69, 72, 73, 76, 77, 78, 79, 80, 93, 94, 95, 111, 117, 118, 119, 120, 134, 135, 138, 139, 141, 142, 144, 146, 147, 148, 149, 155; *Septoria nodorum*, compounds 2, 5, 17, 23, 26, 29, 34, 38, 42, 45, 46, 48, 55, 56, 57, 58, 59, 61, 62, 63, 64, 65, 66, 68, 69, 72, 73, 75, 76, 77, 78, 79, 80, 93, 94, 95, 103, 111, 112, 113, 114, 115, 116, 117, 118, 119, 120, 124, 130, 131, 132, 134, 135, 138, 139, 145, 146, 147, 148, 154, 155; *Septoria tritici*, compounds 1, 2, 3, 4, 5, 7, 8, 9, 12, 13, 15, 17, 18, 19, 22, 24, 25, 26, 27, 28, 30, 33, 34, 35, 36, 37, 38, 39, 40, 41, 43, 44, 45, 46, 47, 48, 49, 50, 51, 53, 54, 56, 57, 58, 59, 60, 61, 62, 63, 64, 65, 66, 68, 69, 70, 71, 72, 73, 74, 76, 77, 78, 79, 80, 81, 82, 83, 84, 85, 89, 90, 92, 93, 94, 95, 96, 97, 98, 99, 100, 101, 102, 103, 105, 106, 108, 109, 110, 111, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 151, 152, 153, 154, 155; *Fusarium culmorum*, compounds 2, 23, 26, 29, 31, 32, 48, 52, 53, 54, 55, 57, 59, 61, 64, 65, 66, 69, 71, 72, 73, 76, 77, 78, 79, 80, 93, 94, 95, 105, 111, 112, 113, 114, 115, 134, 139, 141, 142, 144, 146, 147, 148, 149, 153, 155;

The following compounds from the above Examples gave at least 60% control of the following fungal infection at 20 ppm: *Pythium ultimum*, 1, 4, 8, 12, 13, 14, 15, 16, 17, 19, 23, 29, 31, 32, 35, 41, 44, 51, 52, 53, 54, 55, 56, 57, 58, 60, 61, 62, 64, 65, 66, 69, 70, 72, 73, 74, 76, 77, 78, 79, 80, 82, 87, 88, 90, 91, 92, 94, 95, 96, 101, 102, 105, 108, 111, 112, 113, 115, 116, 117, 118, 119, 120, 127, 128, 130, 131, 132, 134, 135, 138, 139, 140, 141, 142, 143, 146, 147, 148, 149, 150, 151, 152, 153.

The invention claimed is:

1. A compound of the general formula (1)

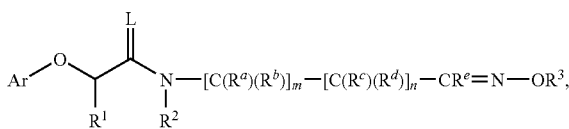

wherein
Ar is a radical of the formula

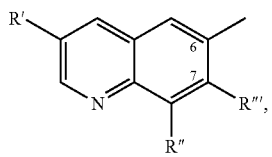

wherein
R' is hydrogen, halogen, $C_{1-4}$alkyl, $C_{2-4}$alkenyl, $C_{2-4}$alkynyl, trialkylsilylethynyl or 3-hydroxy-3-methyl-but-1-yn-1-yl, and
R" and R"', independently of each other, are hydrogen, $C_{1-3}$alkyl or halogen, or
Ar is a radical of the formula

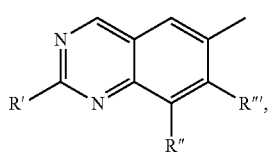

wherein
R' is hydrogen, halogen, $C_{1-4}$alkyl or $C_{2-4}$alkynyl, and
R" and R"', independently of each other, are hydrogen, methyl, ethyl or halogen,
L is O or S;
$R^1$ is $C_{1-4}$ alkyl, halo$C_{1-4}$alkyl or $C_{3-4}$cycloalkyl, or $C_{1-4}$alkoxy, halo($C_{1-4}$)alkoxy or $C_{3-4}$cycloalkoxy, or $C_{1-4}$alkylthio, $C_{1-4}$alkylsulphinyl or $C_{1-4}$alkylsulphonyl, or halo($C_{1-4}$)alkylthio, halo($C_{1-4}$)alkylsulphinyl or halo($C_{1-4}$)alkylsulphonyl, or $C_{3-4}$cyclo-alkylthio, $C_{3-4}$cycloalkylsulphinyl or $C_{3-4}$cycloalkylsulphonyl;

$R^2$ is hydrogen, $C_{1-8}$alkyl, $C_{3-4}$cycloalkyl, $C_{2-8}$alkenyl, cyano($C_{1-4}$)alkyl, $C_{1-4}$alkoxy($C_{1-4}$)-alkyl, $C_{1-4}$alkoxy($C_{1-4}$)alkoxy($C_{1-4}$)alkyl or benzyloxy($C_{1-4}$alkyl, in which the phenyl ring of the benzyl moiety is optionally substituted with $C_{1-4}$alkoxy;

$R^a$ is hydrogen or methyl, and $R^b$ is hydrogen, methyl, cyano, ethynyl, methoxymethyl, allyloxymethyl or propargyloxymethyl, $R^c$ and $R^d$, independently of each other, are hydrogen, $C_{1-4}$ alkyl, halogen, cyano, hydroxy, $C_{1-4}$alkoxy or $C_{1-4}$alkoxycarbonyl, or $R^a$ together with $R^b$, or $R^c$ together with $R^d$ may join to form together with the carbon atoms to which they are attached a 3 to 6 membered carbocyclic or heterocyclic ring containing a heteroatom selected from sulfur, oxygen, nitrogen and $NR^o$, wherein $R^o$ is hydrogen or optionally substituted $C_{1-4}$alkyl, $R^e$ is hydrogen or $C_{1-4}$ alkyl, phenyl, benzyl, thienylmethyl or pyridylmethyl, $R^3$ is hydrogen, optionally substituted $C_{1-6}$alkyl, optionally substituted $C_{3-6}$cycloalkyl which optionally contains a heteratom selected from oxygen, sulphur or nitrogen, optionally substituted $C_{2-4}$alkenyl, optionally substituted $C_{2-6}$alkynyl, $C_{1-4}$alkoxy($C_{1-4}$)alkyl, $C_{3-5}$alkenyloxy($C_{1-4}$)alkyl, $C_{3-5}$alkynyloxy($C_{1-4}$)alkyl, optionally substituted aryl or optionally substituted heteroaryl, m is 1, n is 0, 1 or 2, and salts and N-oxides of the compounds of the formula (1), with the proviso that when Ar is a quinolin-6-yl group and $R^1$ is $C_{1-4}$alkylthio, $C_{1-4}$alkyl-sulphinyl or $C_{1-4}$alkylsulphonyl, or halo($C_{1-4}$)alkylthio, halo($C_{1-4}$)alkylsulphinyl or halo($C_{1-4}$)alkylsulphonyl, or $C_{3-4}$cycloalkylthio, $C_{3-4}$cyclo-alkylsulphinyl or $C_{3-4}$cycloalkylsulphonyl, then the position 7 of the quinolin-6-yl is unsubstituted.

2. A compound according to claim 1, wherein $R^1$ is $C_{1-4}$ alkyl, halo($C_{1-4}$)alkyl, $C_{1-4}$-alkoxy, halo($C_{1-4}$)alkoxy, $C_{1-4}$alkylthio or halo($C_{1-4}$)alkylthio.

3. A compound according to claim 1, wherein $R^2$ is hydrogen, $C_{1-8}$alkyl, $C_{3-8}$cycloalkyl, $C_{2-8}$alkenyl, cyano($C_{1-4}$) alkyl, $C_{1-4}$alkoxy($C_{1-4}$) alkyl, $C_{1-4}$alkoxy($C_{1-4}$)alkoxy($C_{1-4}$) alkyl.

4. A compound according to claim 1, wherein $R^3$ is hydrogen, optionally substituted $C_{1-4}$alkyl, optionally substituted $C_{3-6}$cycloalkyl which optionally contains an oxygen atom, optionally substituted $C_{2-4}$alkenyl, optionally substituted $C_{2-4}$alkynyl or $C_{1-3}$alkoxy($C_{1-3}$)-alkylcarbonyl.

5. A compound according to claim 1, wherein $R^e$ is hydrogen, n is 1, and $R^c$ and $R^d$ are hydrogen.

6. A compound according to claim 1, wherein n is 0.

7. A compound according to claim 1, wherein $R^e$ is hydrogen, and n is 0.

8. A fungicidal composition comprising a fungicidally effective amount of a compound of formula (1) according to claim 1, a suitable carrier or diluent therefore, and optionally a further fungicidal compound.

9. A method of combating or controlling phytopathogenic fungi which comprises applying a fungicidally effective amount of a compound of formula (1) according to claim 1 or a composition according to claim 8 to a plant, to a seed of a plant, to the locus of the plant or seed or to soil or any other plant growth medium.

* * * * *